(12) United States Patent
Hsieh et al.

(10) Patent No.: US 10,127,659 B2
(45) Date of Patent: Nov. 13, 2018

(54) DEEP LEARNING MEDICAL SYSTEMS AND METHODS FOR IMAGE ACQUISITION

(71) Applicant: General Electric Company, Schenectady, NY (US)

(72) Inventors: Jiang Hsieh, Waukesha, WI (US); Gopal Avinash, San Ramon, CA (US); Saad Sirohey, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 28 days.

(21) Appl. No.: 15/360,626

(22) Filed: Nov. 23, 2016

(65) Prior Publication Data

US 2018/0144466 A1 May 24, 2018

(51) Int. Cl.
*G06K 9/00* (2006.01)
*G06T 7/00* (2017.01)
*G06N 3/04* (2006.01)
*G06N 3/08* (2006.01)

(52) U.S. Cl.
CPC ............ *G06T 7/0012* (2013.01); *G06N 3/04* (2013.01); *G06N 3/08* (2013.01); *G06T 2207/10004* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

| 2014/0221832 | A1 | 8/2014 | El-Zehiry et al. |
| 2015/0254555 | A1 | 9/2015 | Williams, Jr. et al. |
| 2016/0034788 | A1* | 2/2016 | Lin ........................ G06T 7/0042 382/157 |

(Continued)

OTHER PUBLICATIONS

Greenspan et al., "Guest Editorial Deep Learning in Medical Imaging: Overview and Future Promise of an Exciting New Technique", IEEE Transactions on Medical Imaging, vol. 35, No. 5, May 2016, 7 pages.

(Continued)

*Primary Examiner* — Hadi Akhavannik
(74) *Attorney, Agent, or Firm* — Hanley, Flight and Zimmerman, LLC

(57) ABSTRACT

Methods and apparatus for improved deep learning for image acquisition are provided. An imaging system configuration apparatus includes a training learning device including a first processor to implement a first deep learning network (DLN) to learn a first set of imaging system configuration parameters based on a first set of inputs from a plurality of prior image acquisitions to configure at least one imaging system for image acquisition, the training learning device to receive and process feedback including operational data from the plurality of image acquisitions by the at least one imaging system. The example apparatus includes a deployed learning device including a second processor to implement a second DLN, the second DLN generated from the first DLN of the training learning device, the deployed learning device configured to provide a second imaging system configuration parameter to the imaging system in response to receiving a second input for image acquisition.

22 Claims, 44 Drawing Sheets

(56) References Cited

U.S. PATENT DOCUMENTS

| | | | |
|---|---|---|---|
| 2016/0171346 A1* | 6/2016 | Han | G06K 9/66 382/103 |
| 2016/0174902 A1* | 6/2016 | Georgescu | G06T 7/73 600/408 |
| 2016/0317127 A1 | 11/2016 | Dos Santos Mendonca et al. | |

OTHER PUBLICATIONS

Shin et al., "Deep Convolutional Neural Networks for Computer-Aided Detection: CNN Architectures, Dataset Characteristics and Transfer Learning", IEEE Transactions on Medical Imaging, vol. 35, No. 5, May 2016, 14 pages.
Setio et al., "Pulmonary Nodule Detection in CT Images: False Positive Reduction Using Multi-View Convolutional Networks", IEEE Transactions on Medical Imaging, vol. 35, No. 5, May 2016, 10 pages.
Eun Young Ko, Md, Phd, "S-Detect™ in Breast Ultrasound: Initial Experience", Samsung Medison, Dec. 17, 2014, 6 pages.
Tulder et al., "Combining Generative and Discriminative Representation Learning for Lung CT Analysis With Convolutional Restricted Boltzmann Machines", IEEE Transactions on Medical Imaging, vol. 35, No. 5, May 2016, 11 pages.
Anthimopoulos et al., "Lung Pattern Classification for Interstitial Lung Diseases Using a Deep Convolutional Neural Network", IEEE Transactions on Medical Imaging, vol. 35, No. 5, May 2016, 10 pages.
Dou et al, "Automatic Detection of Cerebral Microbleeds From MR Images via 3D Convolutional Neural Networks", IEEE Transactions on Medical Imaging, vol. 35, No. 5, May 2016, 14 pages.
Brosch et al. "Deep 3D Convolutional Encoder Networks With Shortcuts for Multiscale Feature Integration Applied to Multiple Sclerosis Lesion Segmentation", IEEE Transactions on Medical Imaging, vol. 35, No. 5, May 2016, 11 pages.
Golkov et al, "q-Space Deep Learning: Twelve-Fold Shorter and Model-Free Diffusion MRI Scans", IEEE Transactions on Medical Imaging, vol. 35, No. 5, May 2016, 8 pages.
Lecun et al., "Deep Learning", Review nature, vol. 521, May 28, 2015, 9 pages.
Roth et al., "Improving Computer-Aided Detection Using Convolutional Neural Networks and Random View Aggregation", IEEE Transactions on Medical Imaging, vol. 35, No. 5, May 2016, 12 pages.
Pavan et al,. "Predicting Alzheimer's disease: a neuroimaging study with 3D convolutional neural networks", Feb. 10, 2105, 9 pages.
Albarqouni et al.,"AggNet: Deep Learning From Crowds for Mitosis Detection in Breast Cancer Histology Images", IEEE Transactions on Medical Imaging, vol. 35, No. 5, May 2016, 9 pages.
Matthew Lai, "Deep Learning for Medical Image Segmentation", Apr. 29, 2015, 23 pages.
Moeskops et al.,"Automatic Segmentation of MR Brain Images With a Convolutional Neural Network", IEEE Transactions on Medical Imaging, vol. 35, No. 5, May 2016, 11 pages.
Brebisson et al, "Deep Neural Networks for Anatomical Brain Segmentation", IEEE Transactions on Medical Imaging, vol. 35, No. 5, May 2016, 9 pages.
Wang et al., "Deep Learning for Identifying Metastatic Breast Cancer", Jun. 18, 2016, 6 pages.
Miao et al., "A CNN Regression Approach for Real-Time 2D/3D Registration", IEEE Transactions on Medical Imaging, vol. 35, No. 5, May 2016, 12 pages.
Pereira et al., "Brain Tumor Segmentation Using Convolutional Neural Networks in MRI Images", IEEE Transactions on Medical Imaging, vol. 35, No. 5, May 2016, 12 pages.
Kallenberg et al., "Unsupervised Deep Learning Applied to Breast Density Segmentation and Mammographic Risk Scoring", IEEE Transactions on Medical Imaging, vol. 35, No. 5, May 2016, 10 pages.
Hou et al., "Blind Image Quality Assessment via Deep Learning", IEEE Transactions on Neural Networks and Learning Systems, vol. 26, No. 6, Jun. 2015, 12 pages.
Bianco et al., "On the Use of Deep Learning for Blind Image Quality Assessment", Feb. 18, 2016, 7 pages.
Tang et al., "Blind Image Quality Assessment using Semi-supervised Rectifier Networks", 8 pages.
Ghadiyaram et al.,"Blind Image Quality Assessment on Real Distorted Images using Deep Belief Nets", 5 pages.
Li et al., "No-reference imagequality assessment with shearlet transform and deep neural networks", retrieved from http://dx.doi.org/10.1016/j.neucom.2014.12.015, Dec. 15, 2014, 16 pages.
Hou et al., "Saliency-guided deep framework for image quality assessment", IEE 2014, 16 pages.
Kan et al., "Convolutional Neural Networks for No-Reference Image Quality Assessment", IEE 2014, 8 pages.
Tian et al., "Query-Dependent Aesthetic Model With Deep Learning for Photo Quality Assessment", IEEE Transactions on Multimedia, vol. 17, No. 11, Nov. 2015, 14 pages.
Lu et al., "RAPID: Rating Pictorial Aesthetics using Deep Learning", Nov. 3, 2014, 10 pages.
Kao et al.,"Visual Aesthetic Quality Assessment with Multi-task Deep Learning", CRIPAC & NLPR, Institute of Automation, Chinese Academy of Sciences, Apr. 18, 2016, 16 pages.
Zhou et al., "Computational Aesthetics of Photos Quality Assessment and Classification Based on Artificial Neural Network with Deep Learning Methods", International Journal of Signal Processing, Image Processing and Pattern Recognition vol. 8, No. 7 (2015), 10 pages.
Kiranyaz et al., "Convolutional Neural Networks for Patient-Specific ECG Classification", IEEE Transactions on Biomedical Engineering (vol. 63, Issue: 3, Mar. 2016), 4 pages.
Yang et al., "A novel method of diagnosing premature ventricular contraction based on sparse auto encoder and softmax regression", Rio-Medical Materials and Engineering 26 (2015) S1549-S1558, 10 pages.
Hasan et al., "A Continuous Learning Framework for Activity Recognition Using Deep Hybrid Feature Models", IEEE Transactions on Multimedia, vol. 17, No. 11, Nov. 2015, 14 pages.
Yan et al., "Multi-Instance Deep Learning: Discover Discriminative Local Anatomies for Body part Recognition", IEEE Transactions on Medical Imaging, vol. 35, No. 5, May 2016, 12 Pages.
Yan et al., "Bodypart Recognition Using Multi-stage Deep Learning", IEEE Transactions on Medical Imaging, vol. 35, No. 5, May 2016, 13 Pages.
Zhao et al., "Segmenting Brain Tissues from Chinese Visible Human Dataset by Deep-Learned Features with Stacked Autoencoder", Hindawi Publishing Corporation, BioMed Research International, vol. 2016, Article ID 5284586, 13 pages.
Avendi et al., "A Combined Deep-Learning and Deformable-Model Approach to Fully Automatic Segmentation of the Left Ventricle in Cardiac MRI", Dec. 29, 2015, 34 pages.
Kiranyaz et al., "Real-Time Patient-Specific ECG Classification by 1D Convolutional Neural Networks", 7th IEEE Engineering in Medicine and Biology Society Conference (EMBC'15), 12 pages.
Ripoll et al., "Assessment of Electrocardiograms with Pretraining and Shallow Networks", Computing in Cardiology 2014; 41:1061-1064, 4 pages.
Sawada et al., "Transfer Learning Method using Multi-Prediction Deep Boltzmann Machines for a small scale dataset", 14th IAPR International Conference on Machine Vision Applications (MVA) May 18-22, 2015. Miraikan, Tokyo, Japan, 4 Pages.
Payan et al., "Predicting Alzheimer's disease: a neuroimaging study with 3D convolutional neural networks", Feb. 9, 2015, 9 pages.
Langkvist, "A review of unsupervised feature learning and deep learning for time-series modeling. Pattern Recognition Letters" (2014), 63 pages.
Zhen et al., "Towards Direct Medical Image Analysis without Segmentation", Oct. 21, 2015, 2 pages.
Ertosun et al., "Probabilistic Visual Search for Masses Within Mammography Images using Deep Learning", 2015 IEEE International Conference on Bioinformatics and Biomedicine (BTBM), 6 pages.

(56) References Cited

OTHER PUBLICATIONS

Wu et al., "Scalable High Performance Image Registration Framework by Unsupervised Deep Feature Representations Learning", IEEE Transactions on Biomedical Engineering (vol. 63, Issue: 7, Jul. 2016), 12 pages.

Ciresan et al., "Deep Neural Networks Segment Neuronal Membranes in Electron Microscopy Images", 2012, 9 Pages.

Jia et al., "A Novel Semi-supervised Deep Learning Framework for Affective State Recognition on EEG Signals", 2014 IEEE International Conference on Bioinformatics and Bioengineering (BIBE), 8 pages.

International Search Report and Written Opinion for International Application No. PCT/US2017/062588 dated Feb. 22, 2018. 12 pages.

\* cited by examiner

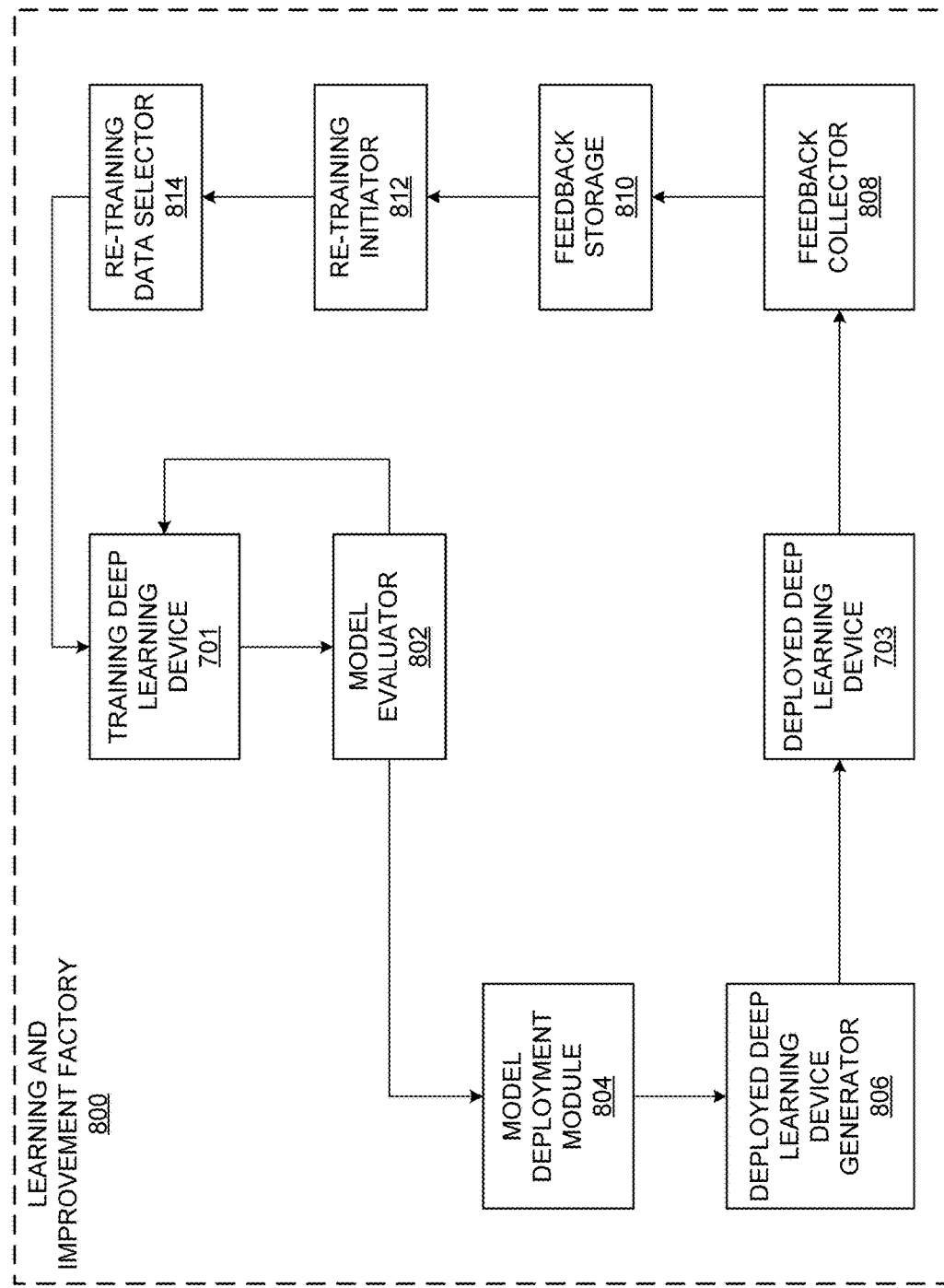

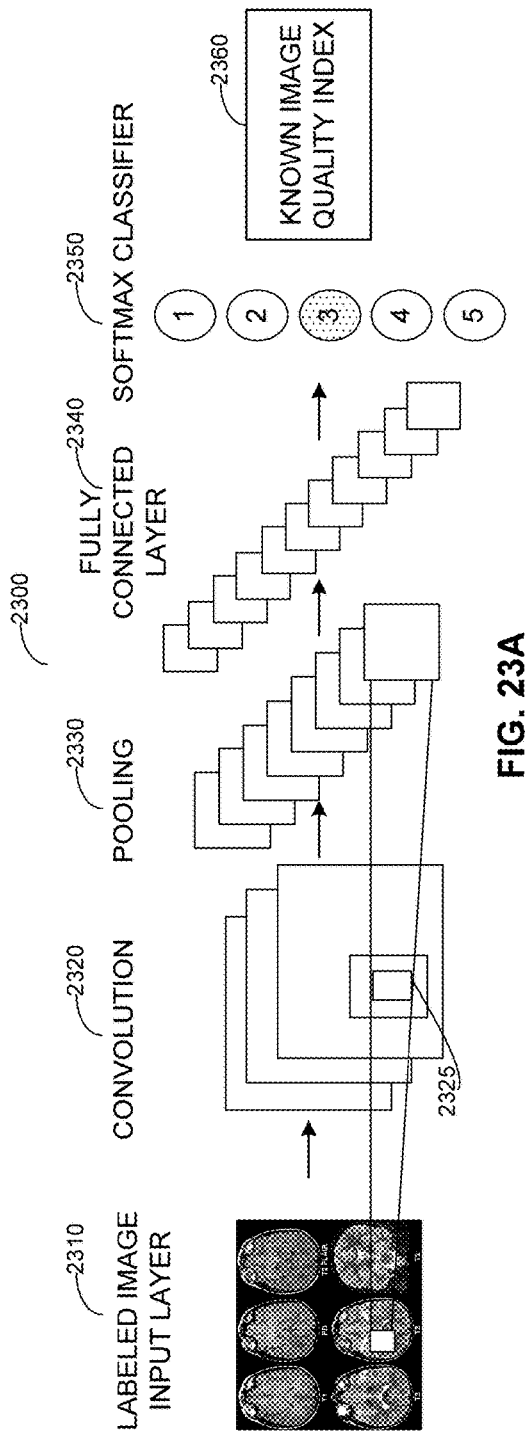
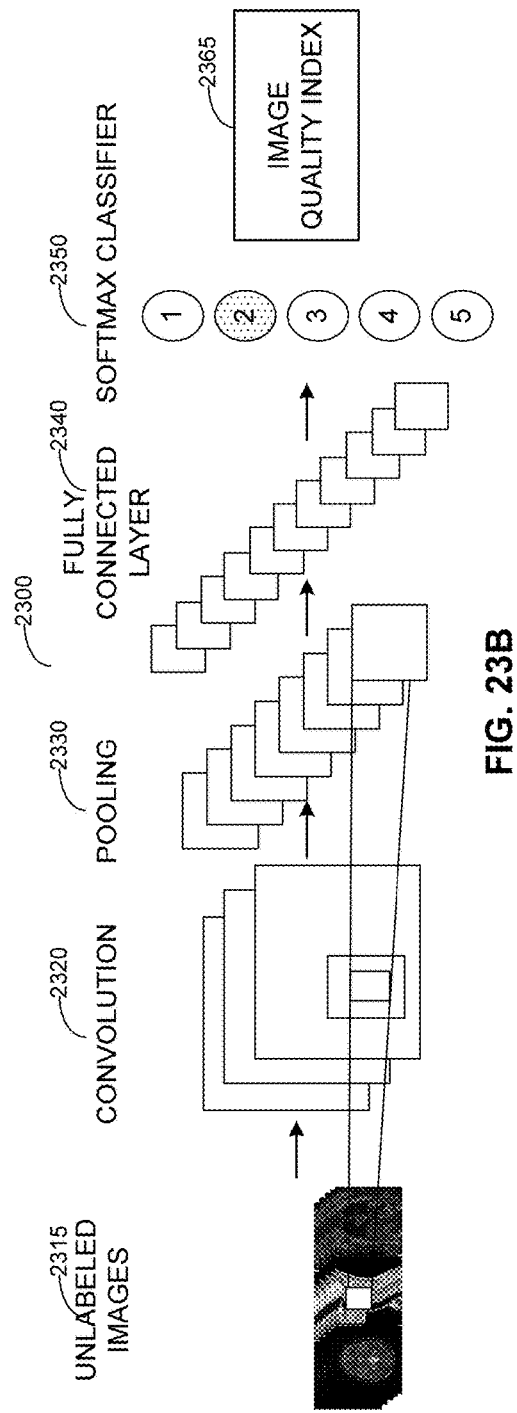
FIG. 23A
FIG. 23B

DEEP LEARNING MEDICAL SYSTEMS AND METHODS FOR IMAGE ACQUISITION

FIELD OF THE DISCLOSURE

This disclosure relates generally to improved medical systems and, more particularly, to improved deep learning medical systems and methods for image acquisition.

BACKGROUND

A variety of economy, technological, and administrative hurdles challenge healthcare facilities, such as hospitals, clinics, doctors' offices, etc., to provide quality care to patients. Economic drivers, less skilled staff, fewer staff, complicated equipment, and emerging accreditation for controlling and standardizing radiation exposure dose usage across a healthcare enterprise create difficulties for effective management and use of imaging and information systems for examination, diagnosis, and treatment of patients.

Healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance.

BRIEF SUMMARY

Certain examples provide an imaging system configuration apparatus including a training learning device including a first processor to implement a first deep learning network to learn a first set of imaging system configuration parameters based on a first set of inputs from a plurality of prior image acquisitions to configure at least one imaging system for image acquisition, the training learning device to receive and process feedback including operational data from the plurality of image acquisitions by the at least one imaging system. The example apparatus includes a deployed learning device including a second processor to implement a second deep learning network, the second deep learning network generated from the first deep learning network of the training learning device, the deployed learning device configured to provide a second imaging system configuration parameter to the imaging system in response to receiving a second input for image acquisition.

Certain examples provide a computer readable medium including instructions which, when executed, configure a machine to implement an imaging system configuration apparatus. The example apparatus includes a training learning device including a first processor to implement a first deep learning network to learn a first set of imaging system configuration parameters based on a first set of inputs from a plurality of prior image acquisitions to configure at least one imaging system for image acquisition, the training learning device to receive and process feedback including operational data from the plurality of image acquisitions by the at least one imaging system. The example apparatus includes a deployed learning device including a second processor to implement a second deep learning network, the second deep learning network generated from the first deep learning network of the training learning device, the deployed learning device configured to provide a second imaging system configuration parameter to the imaging system in response to receiving a second input for image acquisition.

Certain examples provide a method including training a first deep learning network at a training learning device to learn a first set of imaging system configuration parameters based on a first set of inputs from a plurality of prior image acquisitions to configure at least one imaging system for image acquisition, the training learning device to receive and process feedback including operational data from the plurality of image acquisitions by the at least one imaging system. The example method includes generating a second deep learning network at a deployed learning device using the first deep learning network. The example method includes deploying the deployed learning device with the second deep learning network to provide a second imaging system configuration parameter to the imaging system in response to receiving a second input for image acquisition. The example method includes receiving feedback from the imaging system, the feedback including operational data from the image acquisition by the imaging system. The example method includes updating the first deep learning network of the training learning device based on the received feedback.

BRIEF DESCRIPTION OF THE DRAWINGS

FIGS. 8A-8B illustrate example learning and improvement factories leveraging deep learning networks.

FIGS. 23A-23B illustrate example learning and testing/evaluation phases for an image quality deep learning network.

The figures are not scale. Wherever possible, the same reference numbers will be used throughout the drawings and accompanying written description to refer to the same or like parts.

DETAILED DESCRIPTION

Figure 1:
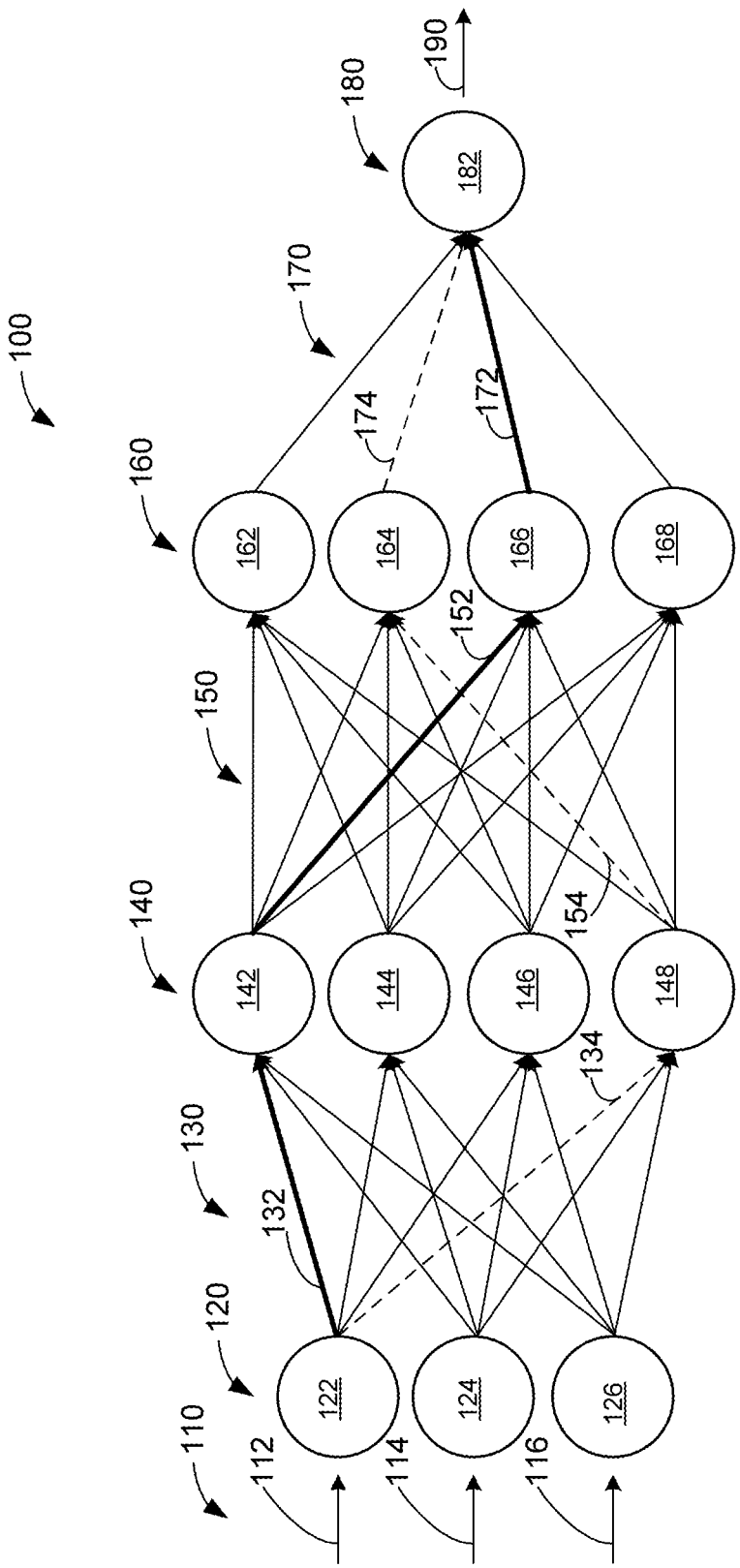
FIG. 1 is a representation of an example deep learning neural network.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements.

While certain examples are described below in the context of medical or healthcare systems, other examples can be implemented outside the medical environment. For example, certain examples can be applied to non-medical imaging such as non-destructive testing, explosive detection, etc.

I. Overview

Imaging devices (e.g., gamma camera, positron emission tomography (PET) scanner, computed tomography (CT) scanner, X-Ray machine, magnetic resonance (MR) imaging machine, ultrasound scanner, etc.) generate medical images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

Acquisition, processing, analysis, and storage of medical image data play an important role in diagnosis and treatment of patients in a healthcare environment. A medical imaging workflow and devices involved in the workflow can be configured, monitored, and updated throughout operation of the medical imaging workflow and devices. Machine learning can be used to help configure, monitor, and update the medical imaging workflow and devices.

Certain examples provide and/or facilitate improved imaging devices which improve diagnostic accuracy and/or coverage. Certain examples facilitate improved image acquisition and reconstruction to provide improved diagnostic accuracy. For example, image quality (IQ) metrics and automated validation can be facilitated using deep learning and/or other machine learning technologies.

Machine learning techniques, whether deep learning networks or other experiential/observational learning system, can be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network can be a training network (e.g., a training network model or device) that learns patterns based on a plurality of inputs and outputs. A deep learning network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "representation learning" is a field of methods for transforming raw data into a representation or feature that can be exploited in machine learning tasks. In supervised learning, features are learned via labeled input.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical images for the purpose of suggesting a possible diagnosis.

Deep Learning

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines using convolutional neural networks (CNNs) can be used for image analysis. Stages of CNN analysis can be used for facial recognition in natural images, computer-aided diagnosis (CAD), etc.

High quality medical image data can be acquired using one or more imaging modalities, such as x-ray, computed tomography (CT), molecular imaging and computed tomography (MICT), magnetic resonance imaging (MRI), etc. Medical image quality is often not affected by the machines producing the image but the patient. A patient moving during an MRI can create a blurry or distorted image that can prevent accurate diagnosis, for example.

Interpretation of medical images, regardless of quality, is only a recent development. Medical images are largely interpreted by physicians, but these interpretations can be subjective, affected by the condition of the physician's experience in the field and/or fatigue. Image analysis via machine learning can support a healthcare practitioner's workflow.

Deep learning machines can provide computer aided detection support to improve their image analysis with respect to image quality and classification, for example. However, issues facing deep learning machines applied to the medical field often lead to numerous false classifications. Deep learning machines must overcome small training datasets and require repetitive adjustments, for example.

Deep learning machines, with minimal training, can be used to determine the quality of a medical image, for example. Semi-supervised and unsupervised deep learning machines can be used to quantitatively measure qualitative aspects of images. For example, deep learning machines can be utilized after an image has been acquired to determine if the quality of the image is sufficient for diagnosis. Supervised deep learning machines can also be used for computer aided diagnosis. Supervised learning can help reduce susceptibility to false classification, for example.

Deep learning machines can utilize transfer learning when interacting with physicians to counteract the small dataset available in the supervised training. These deep learning machines can improve their computer aided diagnosis over time through training and transfer learning.

II. Description of Examples

Example Deep Learning Network Systems

FIG. 1 is a representation of an example deep learning neural network 100. The example neural network 100 includes layers 120, 140, 160, and 180. The layers 120 and 140 are connected with neural connections 130. The layers 140 and 160 are connected with neural connections 150. The layers 160 and 180 are connected with neural connections 170. Data flows forward via inputs 112, 114, 116 from the input layer 120 to the output layer 180 and to an output 190.

The layer 120 is an input layer that, in the example of FIG. 1, includes a plurality of nodes 122, 124, 126. The layers 140 and 160 are hidden layers and include, the example of FIG. 1, nodes 142, 144, 146, 148, 162, 164, 166, 168. The neural network 100 may include more or less hidden layers 140 and 160 than shown. The layer 180 is an output layer and includes, in the example of FIG. 1A, a node 182 with an output 190. Each input 112-116 corresponds to a node 122-126 of the input layer 120, and each node 122-126 of the input layer 120 has a connection 130 to each node 142-148 of the hidden layer 140. Each node 142-148 of the hidden layer 140 has a connection 150 to each node 162-168 of the hidden layer 160. Each node 162-168 of the hidden layer 160 has a connection 170 to the output layer 180. The output layer 180 has an output 190 to provide an output from the example neural network 100.

Of connections 130, 150, and 170 certain example connections 132, 152, 172 may be given added weight while other example connections 134, 154, 174 may be given less weight in the neural network 100. Input nodes 122-126 are activated through receipt of input data via inputs 112-116, for example. Nodes 142-148 and 162-168 of hidden layers 140 and 160 are activated through the forward flow of data through the network 100 via the connections 130 and 150, respectively. Node 182 of the output layer 180 is activated after data processed in hidden layers 140 and 160 is sent via connections 170. When the output node 182 of the output layer 180 is activated, the node 182 outputs an appropriate value based on processing accomplished in hidden layers 140 and 160 of the neural network 100.

Figure 2:
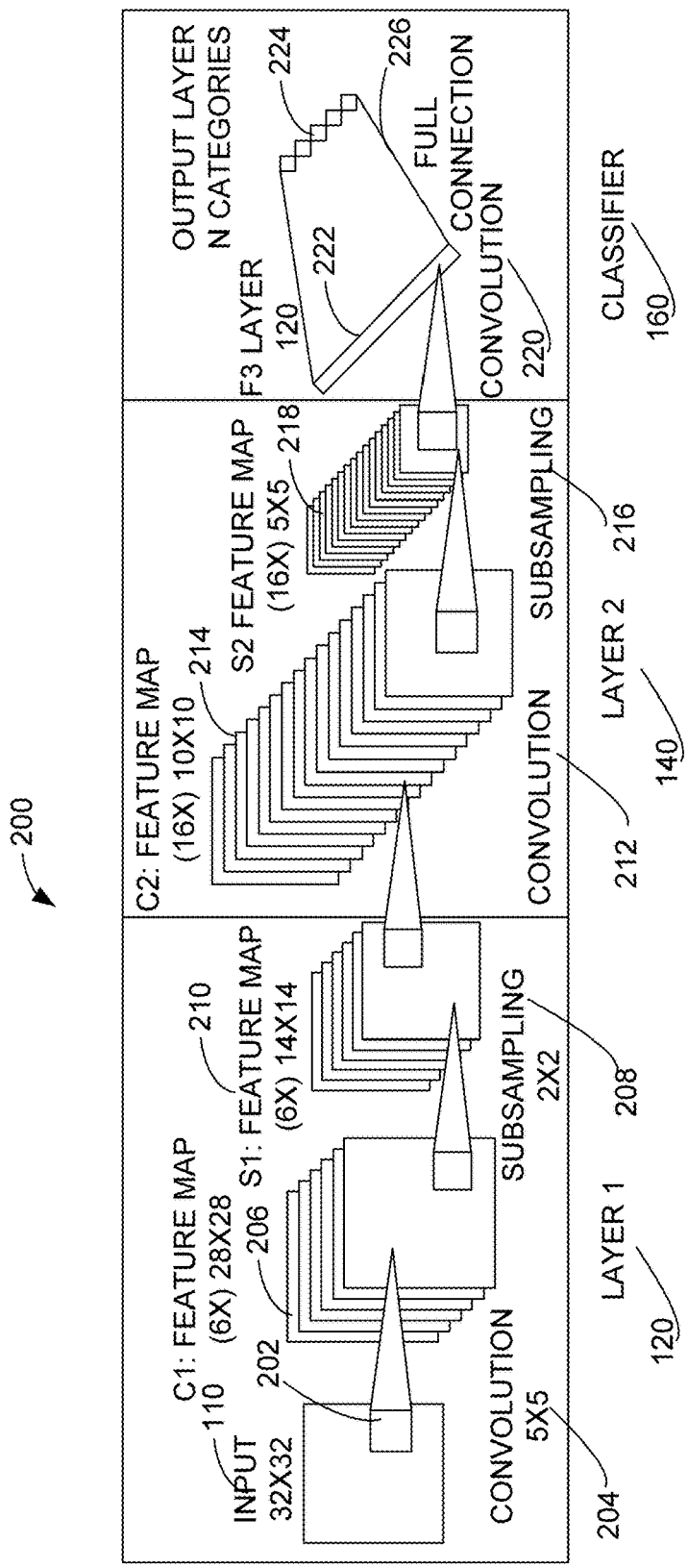
FIG. 2 illustrates a particular implementation of the example neural network as a convolutional neural network.

FIG. 2 illustrates a particular implementation of the example neural network 100 as a convolutional neural network 200. As shown in the example of FIG. 2, an input 110 is provided to the first layer 120 which processes and propagates the input 110 to the second layer 140. The input 110 is further processed in the second layer 140 and propagated to the third layer 160. The third layer 160 categorizes data to be provided to the output layer 180. More specifically, as shown in the example of FIG. 2, a convolution 204 (e.g., a 5×5 convolution, etc.) is applied to a portion or window (also referred to as a "receptive field") 202 of the input 110 (e.g., a 32×32 data input, etc.) in the first layer 120 to provide a feature map 206 (e.g., a (6×) 28×28 feature map, etc.). The convolution 204 maps the elements from the input 110 to the feature map 206. The first layer 120 also provides subsampling (e.g., 2×2 subsampling, etc.) to generate a reduced feature map 210 (e.g., a (6×) 14×14 feature map, etc.). The feature map 210 undergoes a convolution 212 and is propagated from the first layer 120 to the second layer 140, where the feature map 210 becomes an expanded feature map 214 (e.g., a (16×) 10×10 feature map, etc.). After subsampling 216 in the second layer 140, the feature map 214 becomes a reduced feature map 218 (e.g., a (16×) 4×5 feature map, etc.). The feature map 218 undergoes a convolution 220 and is propagated to the third layer 160, where the feature map 218 becomes a classification layer 222 forming an output layer of N categories 224 with connection 226 to the convoluted layer 222, for example.

Figure 3:
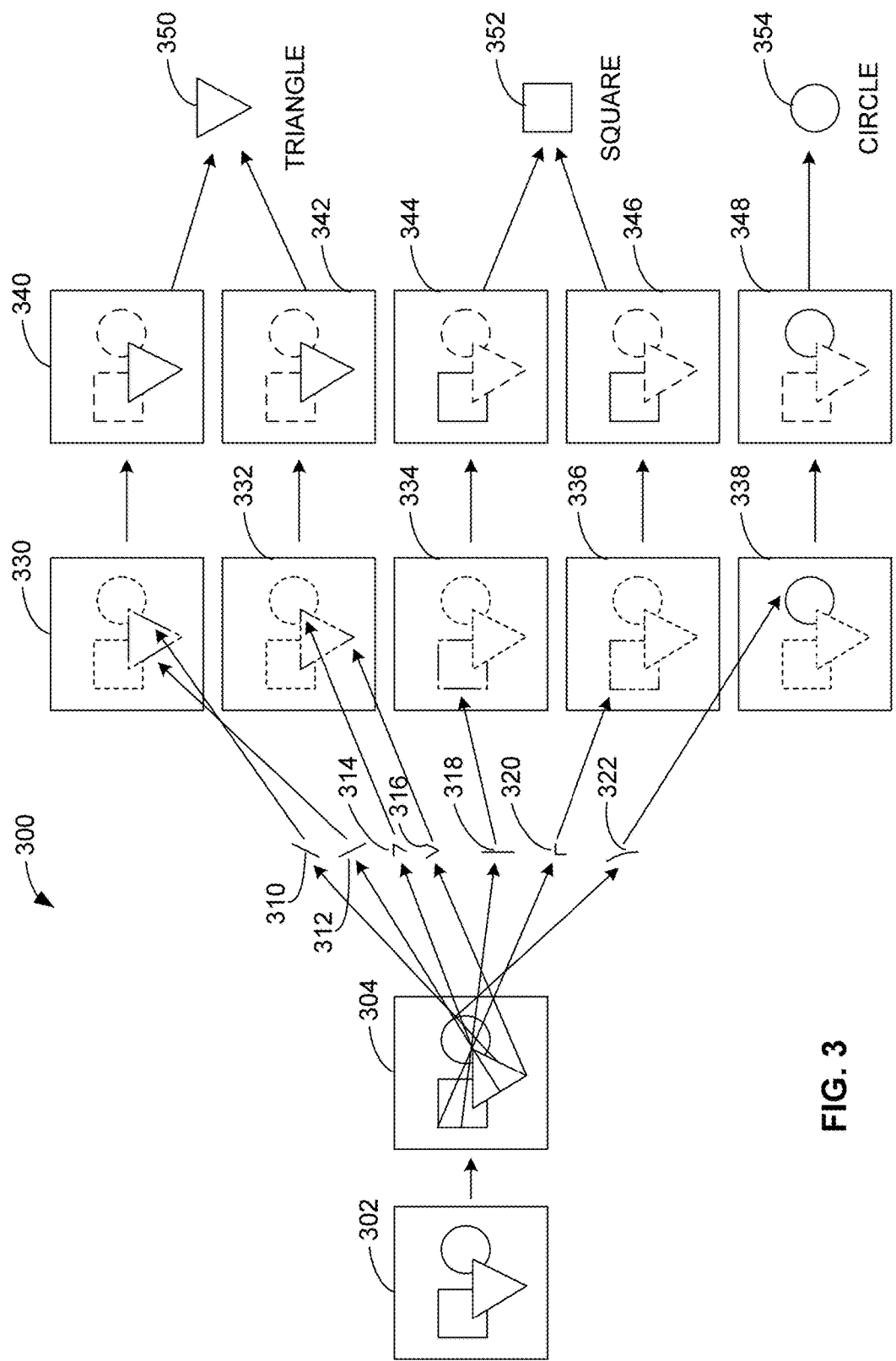
FIG. 3 is a representation of an example implementation of an image analysis convolutional neural network.

FIG. 3 is a representation of an example implementation of an image analysis convolutional neural network 300. The convolutional neural network 300 receives an input image 302 and abstracts the image in a convolution layer 304 to identify learned features 310-322. In a second convolution layer 330, the image is transformed into a plurality of images 330-338 in which the learned features 310-322 are each accentuated in a respective sub-image 330-338. The images 330-338 are further processed to focus on the features of interest 310-322 in images 340-348. The resulting images 340-348 are then processed through a pooling layer which reduces the size of the images 340-348 to isolate portions 350-354 of the images 340-348 including the features of interest 310-322. Outputs 350-354 of the convolutional neural network 300 receive values from the last non-output layer and classify the image based on the data received from the last non-output layer. In certain examples, the convolutional neural network 300 may contain many different variations of convolution layers, pooling layers, learned features, and outputs, etc.

Figure 4A:
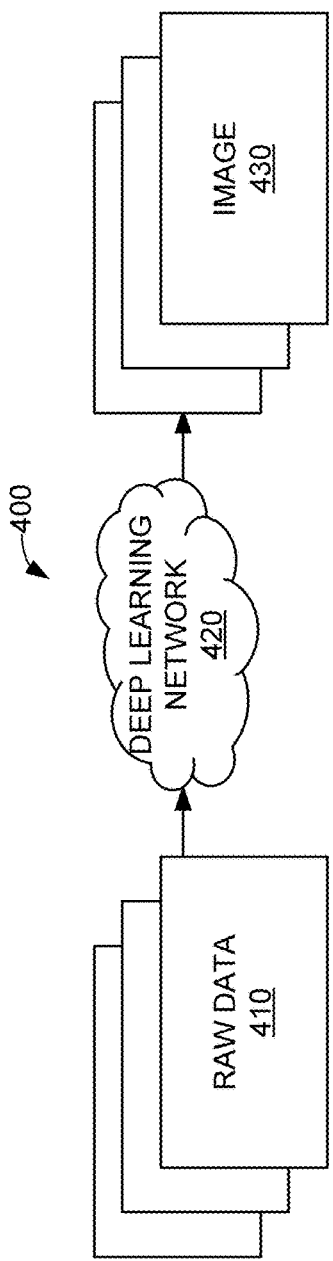
FIG. 4A illustrates an example configuration to apply a deep learning network to process and/or otherwise evaluate an image.

FIG. 4A illustrates an example configuration 400 to apply a deep learning network to process and/or otherwise evaluate an image. Deep learning can be applied to a variety of processes including image acquisition, image reconstruction, image analysis/diagnosis, etc. As shown in the example configuration 400 of FIG. 4A, raw data 410 (e.g., raw data 410 such as sonogram raw data, etc., obtained from an imaging scanner such as an x-ray, computed tomography, ultrasound, magnetic resonance, etc., scanner) is fed into a deep learning network 420. The deep learning network 420 processes the data 410 to correlate and/or otherwise combine the raw image data 420 into a resulting image 430 (e.g., a "good quality" image and/or other image providing sufficient quality for diagnosis, etc.). The deep learning network 420 includes nodes and connections (e.g., pathways) to associate raw data 410 with a finished image 430. The deep learning network 420 can be a training deep learning network that learns the connections and processes feedback to establish connections and identify patterns, for example. The deep learning network 420 can be a deployed deep learning network that is generated from a training network and leverages the connections and patterns established in the training network to take the input raw data 410 and generate the resulting image 430, for example.

Once the DLN 420 is trained and produces good images 630 from the raw image data 410, the network 420 can continue the "self-learning" process and refine its performance as it operates. For example, there is "redundancy" in the input data (raw data) 410 and redundancy in the network 420, and the redundancy can be exploited.

If weights assigned to nodes in the DLN 420 are examined, there are likely many connections and nodes with very low weights. The low weights indicate that these connections and nodes contribute little to the overall performance of the DLN 420. Thus, these connections and nodes are redundant. Such redundancy can be evaluated to reduce redundancy in the inputs (raw data) 410. Reducing input 410 redundancy can result in savings in scanner hardware, reduced demands on components, and also reduced exposure dose to the patient, for example.

In deployment, the configuration 400 forms a package 400 including an input definition 410, a trained network 420, and an output definition 430. The package 400 can be deployed and installed with respect to another system, such as an imaging system, analysis engine, etc.

Figure 4B:
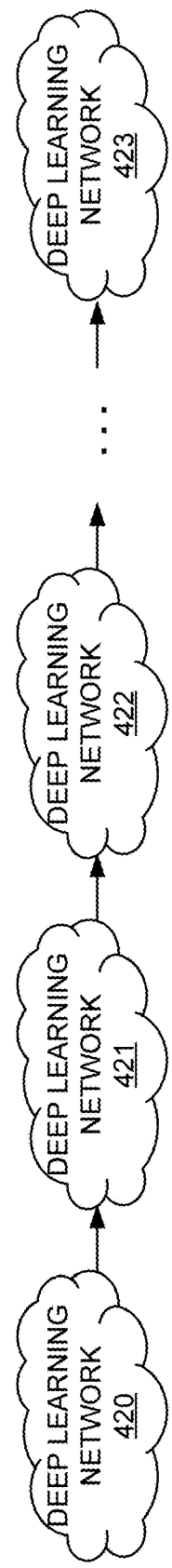
FIG. 4B illustrates a combination of a plurality of deep learning networks.

As shown in the example of FIG. 4B, the deep learning network 420 can be chained and/or otherwise combined with a plurality of deep learning networks 421-423 to form a larger learning network. The combination of networks 420-423 can be used to further refine responses to inputs and/or allocate networks 420-423 to various aspects of a system, for example.

In some examples, in operation, "weak" connections and nodes can initially be set to zero. The DLN 420 then processes its nodes in a retaining process. In certain examples, the nodes and connections that were set to zero are not allowed to change during the retraining. Given the redundancy present in the network 420, it is highly likely that equally good images will be generated. As illustrated in FIG. 4B, after retraining, the DLN 420 becomes DLN 421. DLN 421 is also examined to identify weak connections and nodes and set them to zero. This further retrained network is DLN 422. The example DLN 422 includes the "zeros" in DLN 421 and the new set of nodes and connections. The DLN 422 continues to repeat the processing until a good image quality is reached at a DLN 423, which is referred to as a "minimum viable net (MVN)". The DLN 423 is a MVN because if additional connections or nodes are attempted to be set to zero in DLN 423, image quality can suffer.

Once the MVN has been obtained with the DLN 423, "zero" regions (e.g., dark irregular regions in a graph) are mapped to the input 410. Each dark zone is likely to map to one or a set of parameters in the input space. For example, one of the zero regions may be linked to the number of views and number of channels in the raw data. Since redundancy in the network 423 corresponding to these parameters can be reduced, there is a highly likelihood that the input data can be reduced and generate equally good output. To reduce input data, new sets of raw data that correspond to the reduced parameters are obtained and run through the DLN 421. The network 420-423 may or may not be simplified, but one or more of the DLNs 420-423 is processed until a "minimum viable input (MVI)" of raw data input 410 is reached. At the MVI, a further reduction in the input raw data 410 may result in reduced image 430 quality. The MVI can result in reduced complexity in data acquisition, less demand on system components, reduced stress on patients (e.g., less breath-hold or contrast), and/or reduced dose to patients, for example.

By forcing some of the connections and nodes in the DLNs 420-423 to zero, the network 420-423 to build "collaterals" to compensate. In the process, insight into the topology of the DLN 420-423 is obtained. Note that DLN 421 and DLN 422, for example, have different topology since some nodes and/or connections have been forced to zero. This process of effectively removing connections and nodes from the network extends beyond "deep learning" and can be referred to as "deep-deep learning".

In certain examples, input data processing and deep learning stages can be implemented as separate systems. However, as separate systems, neither module may be aware of a larger input feature evaluation loop to select input parameters of interest/importance. Since input data processing selection matters to produce high-quality outputs, feedback from deep learning systems can be used to perform input parameter selection optimization or improvement via a model. Rather than scanning over an entire set of input parameters to create raw data (e.g., which is brute force and can be expensive), a variation of active learning can be implemented. Using this variation of active learning, a starting parameter space can be determined to produce desired or "best" results in a model. Parameter values can then be randomly decreased to generate raw inputs that decrease the quality of results while still maintaining an acceptable range or threshold of quality and reducing runtime by processing inputs that have little effect on the model's quality.

Figure 5:
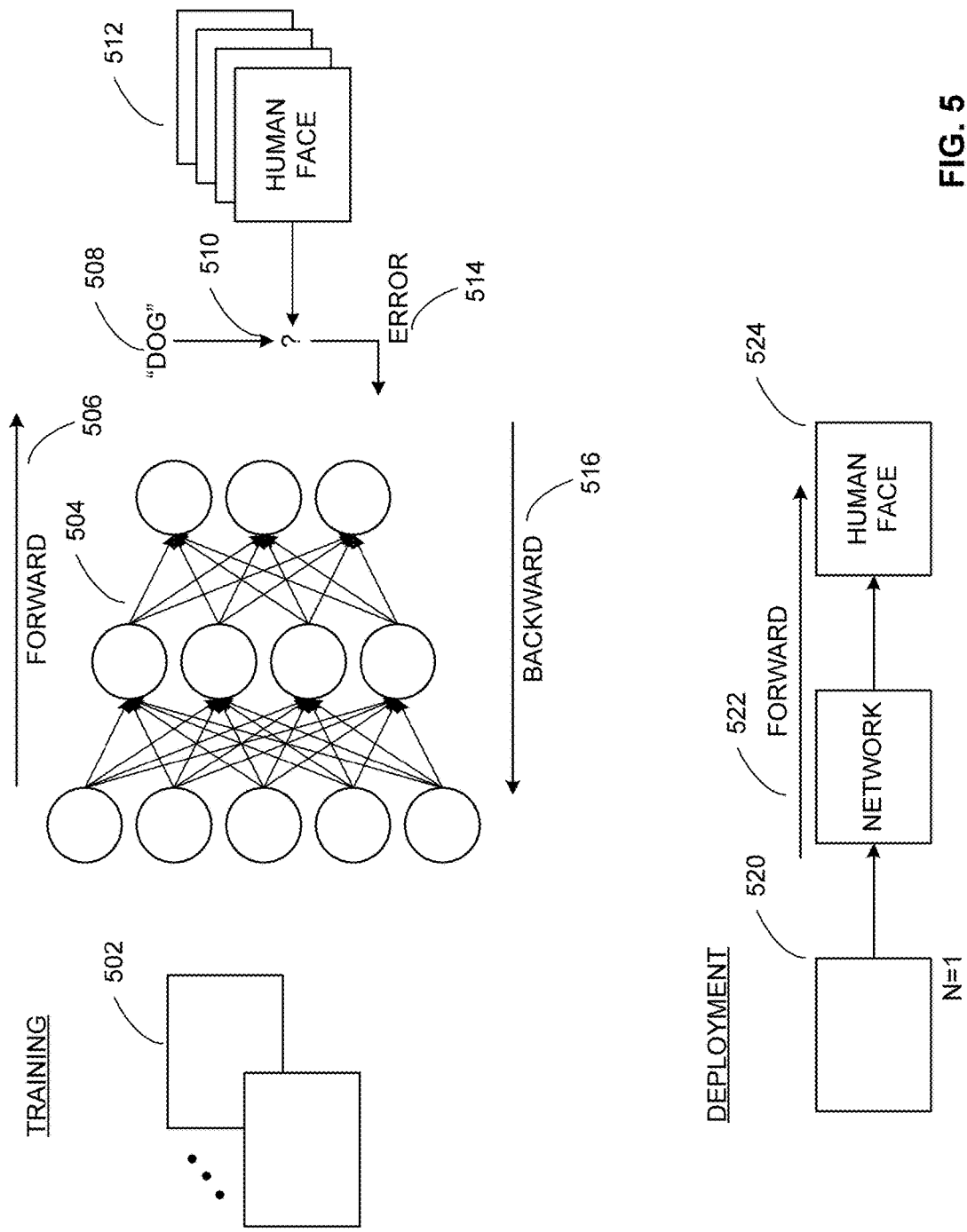
FIG. 5 illustrates example training and deployment phases of a deep learning network.

FIG. 5 illustrates example training and deployment phases of a deep learning network. As shown in the example of FIG. 5, in the training phase, a set of inputs 502 is provided to a network 504 for processing. In this example, the set of inputs 502 can include facial features of an image to be identified. The network 504 processes the input 502 in a forward direction 506 to associate data elements and identify patterns. The network 504 determines that the input 502 represents a dog 508. In training, the network result 508 is compared 510 to a known outcome 512. In this example, the known outcome 512 is a human face (e.g., the input data set 502 represents a human face, not a dog face). Since the determination 508 of the network 504 does not match 510 the known outcome 512, an error 514 is generated. The error 514 triggers an analysis of the known outcome 512 and associated data 502 in reverse along a backward pass 516 through the network 504. Thus, the training network 504 learns from forward 506 and backward 516 passes with data 502, 512 through the network 405.

Once the comparison of network output 508 to known output 512 matches 510 according to a certain criterion or threshold (e.g., matches n times, matches greater than x percent, etc.), the training network 504 can be used to generate a network for deployment with an external system. Once deployed, a single input 520 is provided to a deployed deep learning network 522 to generate an output 524. In this case, based on the training network 504, the deployed network 522 determines that the input 520 is an image of a human face 524.

Figure 6:
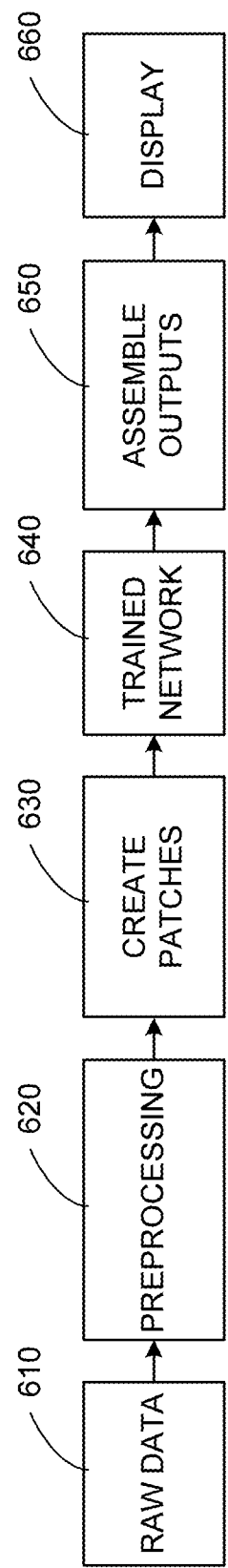
FIG. 6 illustrates an example product leveraging a trained network package to provide a deep learning product offering.

FIG. 6 illustrates an example product leveraging a trained network package to provide a deep learning product offering. As shown in the example of FIG. 6, an input 610 (e.g., raw data) is provided for preprocessing 620. For example, the raw input data 610 is preprocessed 620 to check format, completeness, etc. Once the data 610 has been preprocessed 620, patches are created 630 of the data. For example, patches or portions or "chunks" of data are created 630 with a certain size and format for processing. The patches are then fed into a trained network 640 for processing. Based on learned patterns, nodes, and connections, the trained network 640 determines outputs based on the input patches. The outputs are assembled 650 (e.g., combined and/or otherwise grouped together to generate a usable output, etc.). The output is then displayed 660 and/or otherwise output to a user (e.g., a human user, a clinical system, an imaging modality, a data storage (e.g., cloud storage, local storage, edge device, etc.), etc.).

Figure 7A:
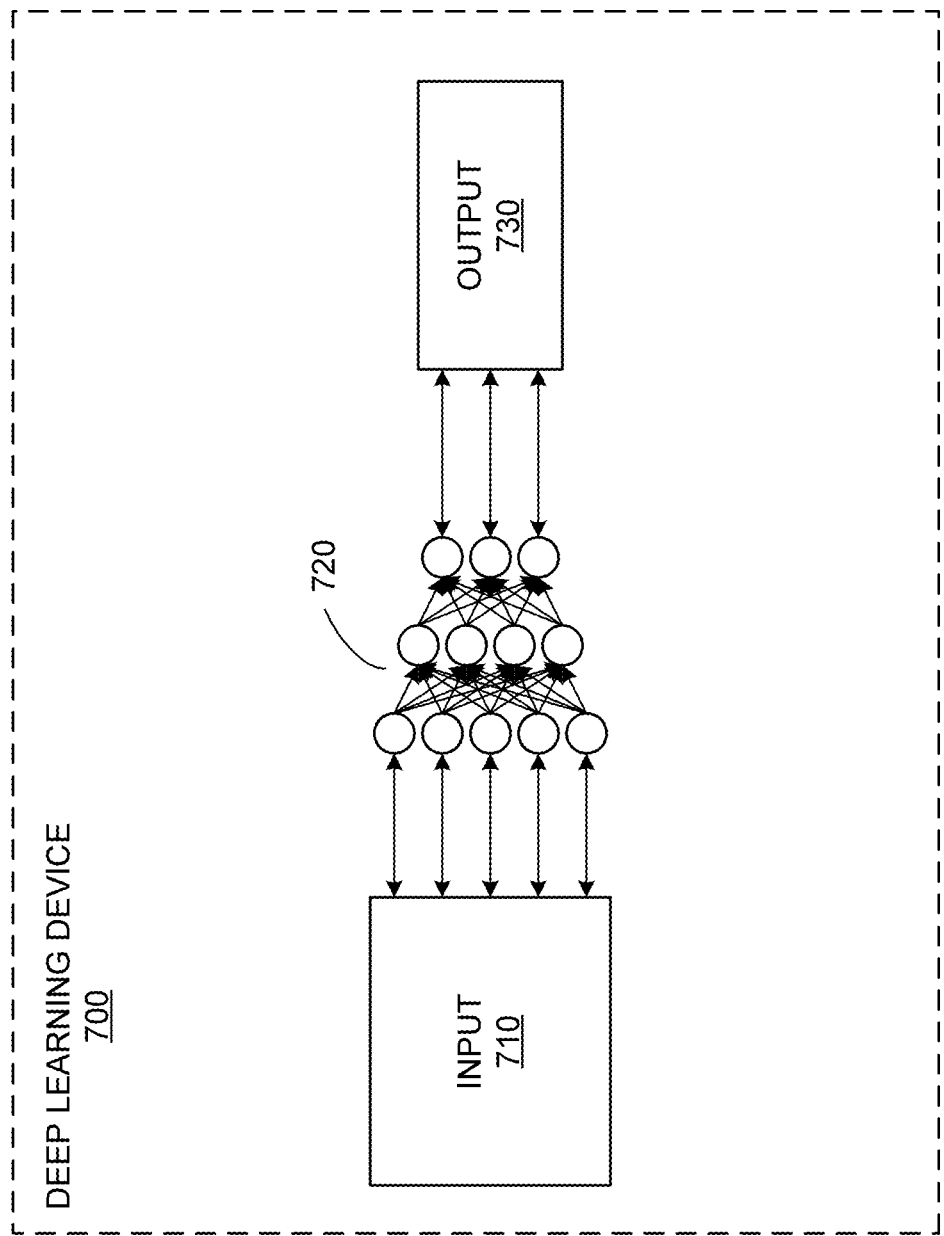
FIGS. 7A-7C illustrate various deep learning device configurations.
Figure 7B:
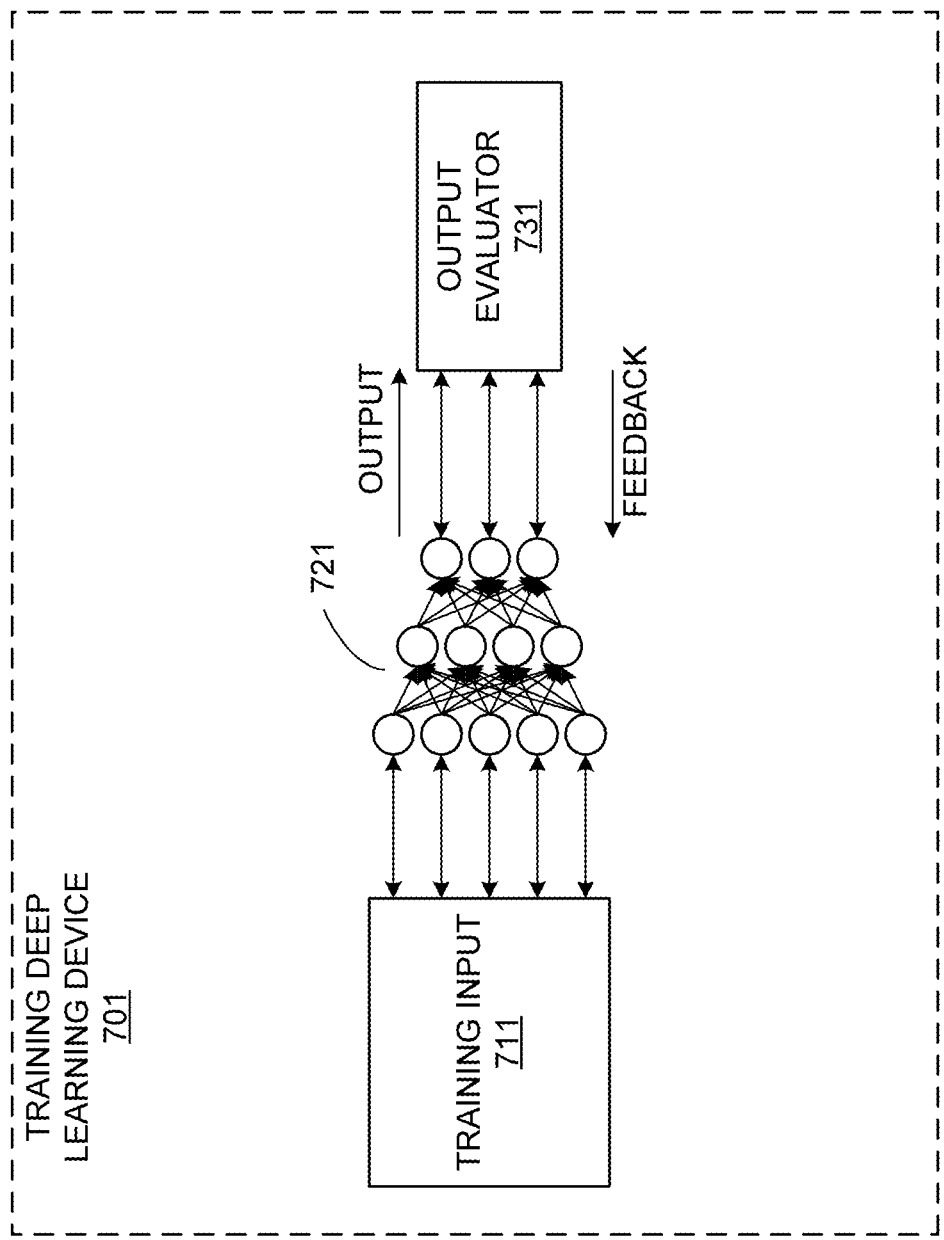
Figure 7C:
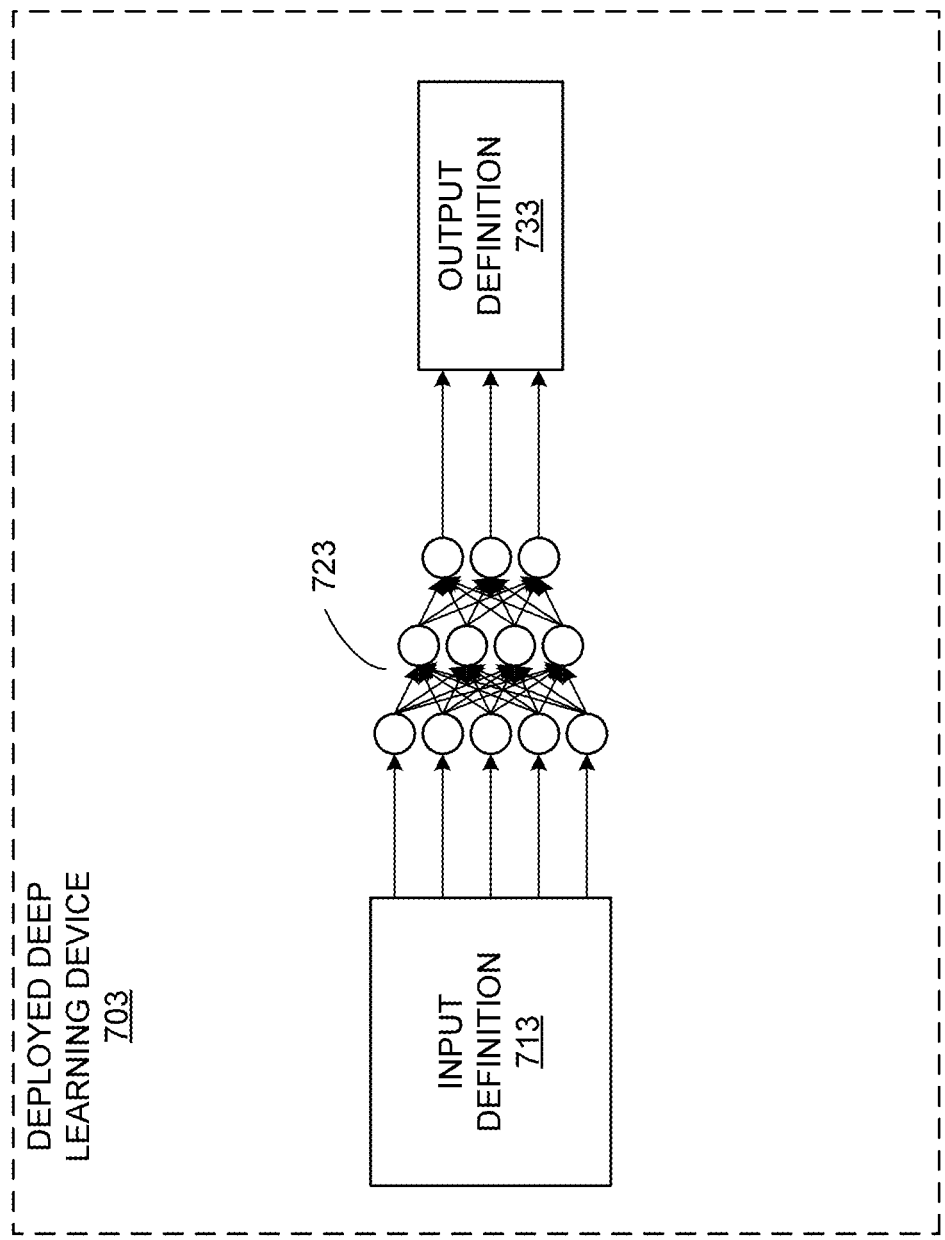

As discussed above, deep learning networks can be packaged as devices for training, deployment, and application to a variety of systems. FIGS. 7A-7C illustrate various deep learning device configurations. For example, FIG. 7A shows a general deep learning device 700. The example device 700 includes an input definition 710, a deep learning network model 720, and an output definitions 730. The input definition 710 can include one or more inputs translating into one or more outputs 730 via the network 720.

FIG. 7B shows an example training deep learning network device 701. That is, the training device 701 is an example of the device 700 configured as a training deep learning network device. In the example of FIG. 7B, a plurality of training inputs 711 are provided to a network 721 to develop connections in the network 721 and provide an output to be evaluated by an output evaluator 731. Feedback is then provided by the output evaluator 731 into the network 721 to further develop (e.g., train) the network 721. Additional input 711 can be provided to the network 721 until the output evaluator 731 determines that the network 721 is trained (e.g., the output has satisfied a known correlation of input to output according to a certain threshold, margin of error, etc.).

FIG. 7C depicts an example deployed deep learning network device 703. Once the training device 701 has learned to a requisite level, the training device 701 can be deployed for use. While the training device 701 processes multiple inputs to learn, the deployed device 703 processes a single input to determine an output, for example. As shown in the example of FIG. 7C, the deployed device 703 includes an input definition 713, a trained network 723, and an output definition 733. The trained network 723 can be generated from the network 721 once the network 721 has been sufficiently trained, for example. The deployed device 703 receives a system input 713 and processes the input 713 via the network 723 to generate an output 733, which can then be used by a system with which the deployed device 703 has been associated, for example.

In certain examples, the training device 701 and/or deployed device 703 can be integrated in a learning and improvement factory to provide output to a target system, collect feedback, and update/re-train based on the feedback. FIG. 8A illustrates an example learning and improvement factory 800 including the training deep learning device 701 and the deployed deep learning device 703. As shown in the example of FIG. 8A, the training deep learning device 701 provides output to a model evaluator 802. The model evaluator 802 compares the output of the device 701 to a known output and/or otherwise measures accuracy, precision, and/or quality of the output to determine whether or not the training device 701 is ready for deployment. Once the model evaluator 802 has determined that the device 701 has been properly trained, the model evaluator 802 provides a model of the trained network from the device 701 to a model deployment module 804, which prepares the trained model for deployment. The module 804 provides the prepared model to a deployed deep learning device generator 806 which instantiates the deployed deep learning device 703 with a framework or package for input definition and output definition around a model of the trained network from the device 701.

The deployed device 703 operates on input and provides output, and a feedback collector 808 monitors the output (and input) and gathers feedback based on operation of the deployed deep learning device 703. The feedback is stored in feedback storage 810 until a certain amount of feedback has been collected (e.g., a certain quantity, a certain quality/consistency, a certain time period, etc.). Once sufficient feedback has been collected, a re-training initiator 812 is triggered. The re-training initiator 812 retrieves data from the feedback storage 810 and operates in conjunction with a re-training data selector 814 to select data from the feedback storage 810 to provide to the training deep learning device 701. The network of the training device 701 is then updated/re-trained using the feedback until the model evaluator 802 is satisfied that the training network model is complete. The updated/re-trained model is then prepared and deployed in the deployed deep learning device 703 as described above.

Figure 8B:
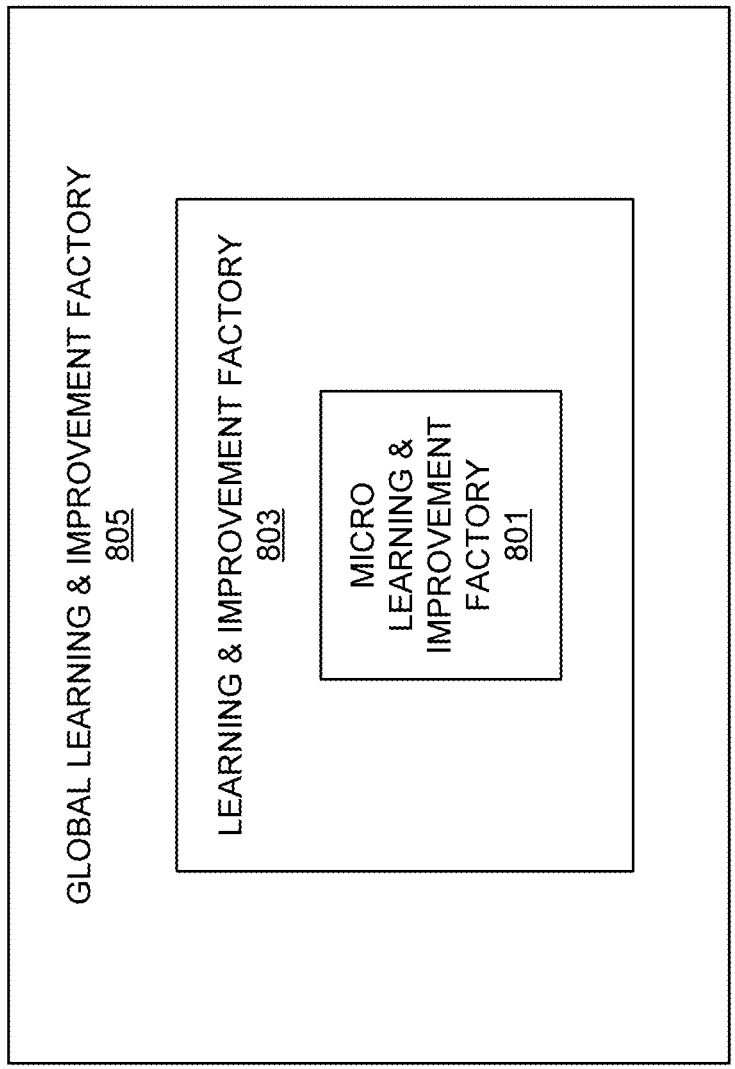

As shown in the example of FIG. 8B, the learning and improvement factory 800 can be implemented in a variety of levels/hierarchy. For example, a micro learning and improvement factory 801 may model and/or provide support for a particular device, device feature, etc. A learning and improvement factory 803 can target an overall system or installation, for example. A global learning and improvement factory 805 can provide output and model an organization, facility, etc. Thus, learning and improvement factories 801-805 can be implemented through an organization to learn, model, and improve system accuracy, performance, effectiveness, safety, efficiency, etc.

Figure 8C:
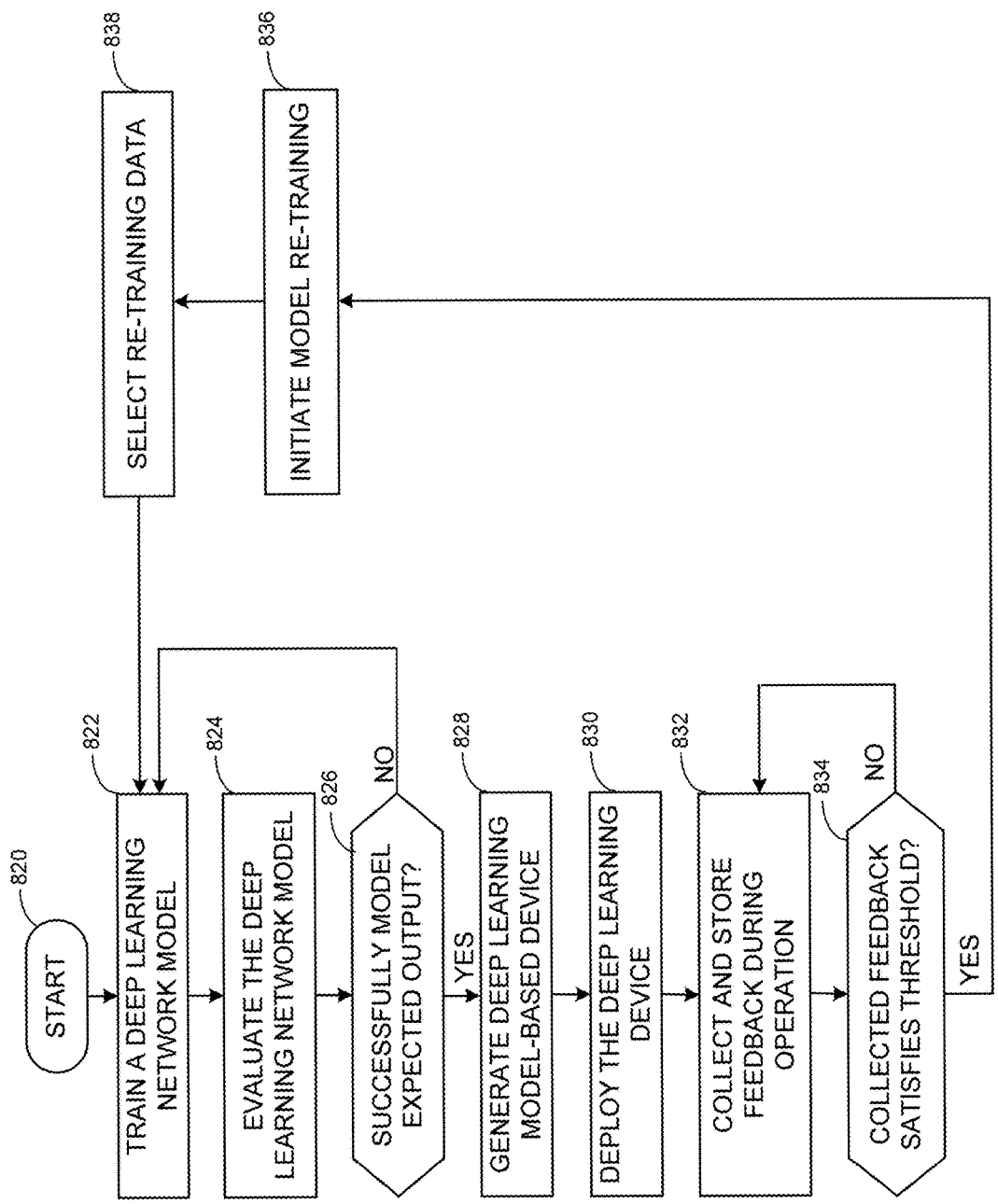
FIG. 8C illustrates an example flow diagram of an example method to train and deploy a deep learning network model.

FIG. 8C illustrates a flow diagram of an example method 820 to train and deploy a deep learning network model. At block 822, a deep learning network model is trained. For example, a plurality of inputs are provided to the network, and output is generated. At block 824, the deep learning network model is evaluated. For example, output of the network is compared against known/reference output for those inputs. As the network makes connections and learns, the accuracy of the network model improves. At block 826, the output is evaluated to determine whether the network has successfully modeled the expected output. If the network has not, then the training process continues at block 822. If the network has successfully modeled the output, then, at block 828, a deep learning model-based device is generated. At block 830, the deep learning device is deployed.

At block 832, feedback from operation of the deployed deep learning model-based device is collected and stored until the collected feedback satisfies a threshold (block 834). Feedback can include input, deployed model information, pre-and/or post-processing information, actual and/or corrected output, etc. Once the feedback collection threshold is satisfied, at block 836, model re-training is initiated. At block 838, data from the collected feedback (and/or other input data) is selected to re-train the deep learning model. Data selection can include pre- and/or post-processing to properly format the data for model training, etc. Control then passes to block 822 to (re)train the deep learning network model.

Figure 8D:
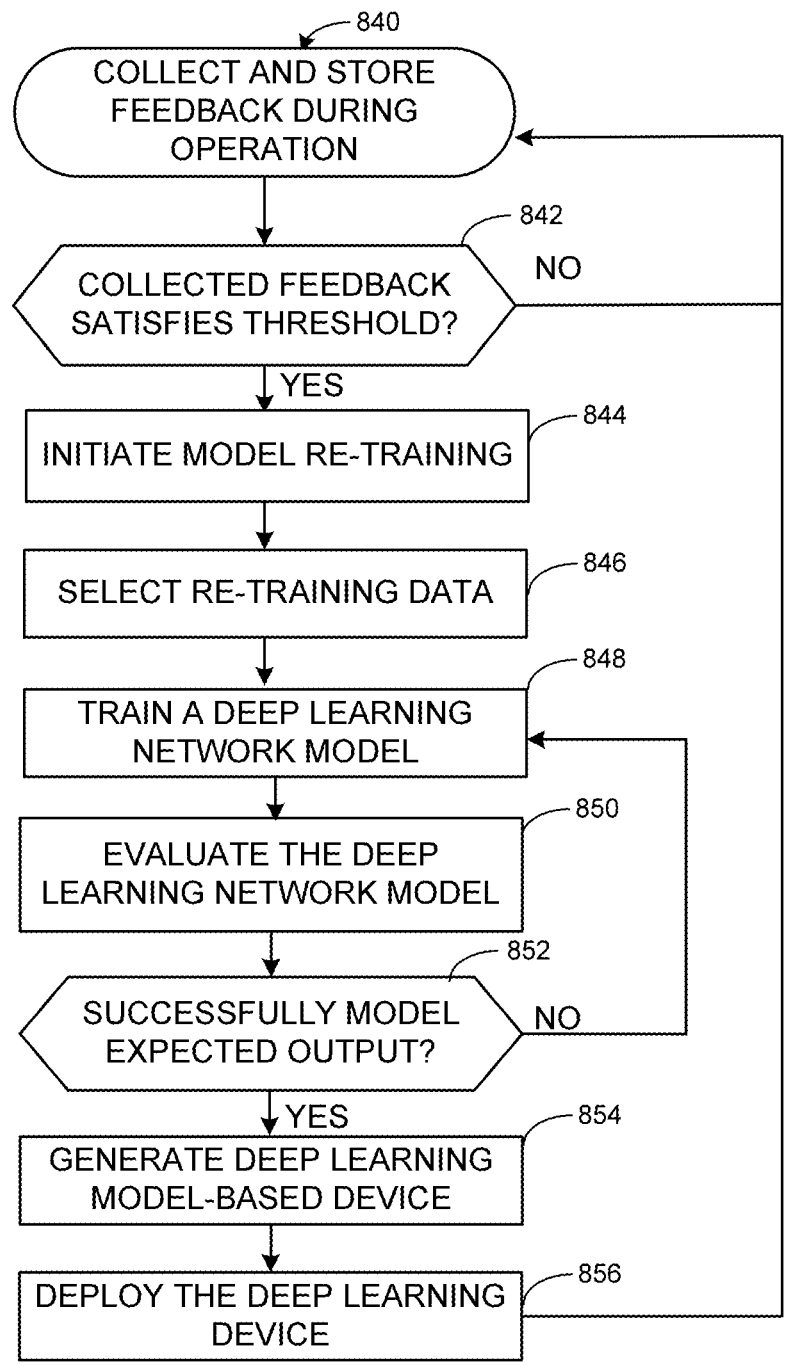
FIG. 8D illustrates an example process to collect and store feedback during operation of a deployed deep learning network model-based device and re-train the model for re-deployment.

FIG. 8D re-iterates an example process to collect and store feedback during operation 840 of the deployed deep learning network model-based device and re-train the model for re-deployment. Feedback can include input, deployed model information, pre- and/or post-processing information, actual and/or corrected output, etc. At block 842, the collected feedback is reviewed to determine whether the collected feedback satisfies a collection/feedback threshold (e.g., an amount of feedback, a frequency of feedback, a type of feedback, an amount of time lapsed for feedback, etc.). If the threshold is not satisfied, then feedback collection and storage continues at block 840. If the threshold is satisfied, however, then, at block 844, model re-training is initiated.

At block 846, data is selected to re-train the deep learning network model. Data includes collected feedback and can also include other data including original input data to the model and/or other reference data, for example. Thus, the model may not be re-trained exclusively on feedback data but on a mix of old and new data fed into the deep learning model, for example. Data selection can include pre- and/or post-processing to properly format the data for model training, etc.

At block 848, the deep learning network model is (re)trained. That is, data is provided as input to modify the network model and generate an output. At block 850, the output is evaluated to determine whether the network model has been (re)trained. At block 852, if the network has not modeled expected output, then control reverts to block 848 to continue model training with input and output evaluation. If the (re)trained network has successfully modeled the expected output (e.g., over a certain threshold of times, etc.), then, at block 854, the deep learning model-based device is generated. At block 856, the deep learning device is deployed. Thus, a model can be initiated trained and/or re-trained and used to generated a deployed network model-based device. While the deployed device is not modified during operation, the training model can be updated and/or otherwise modified and periodically used to replace/re-deploy the deployed network model, for example.

Figure 9:
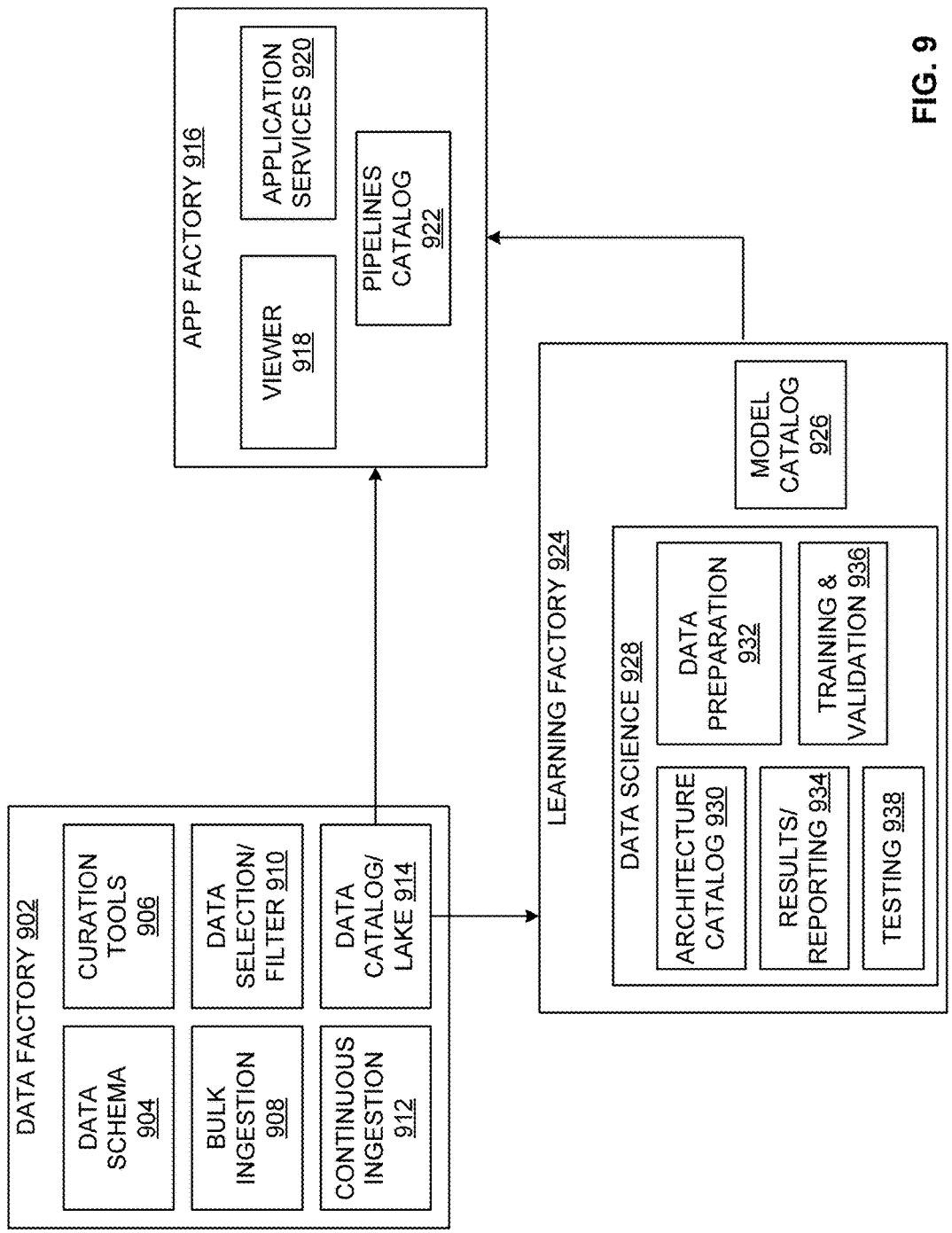
FIG. 9 illustrates an example system including a data factory, application factory, and learning factory leveraging deep learning to provide applications for one or more systems and/or associated users.

FIG. 9 illustrates an example system including a data factory 902, application factory 916, and learning factory 924 leveraging deep learning to provide applications for one or more systems and/or associated users. In the example of FIG. 9, the data factory 902 includes one or more data schema 904, curation tools 906, bulk data ingestion 908, data selection/filter 910, continuous data ingestion 912, and data catalog/lake 914. The example data factory 902 ingests data 908, 912 and can process the data to select/filter the data 910 and format the data according to a certain schema 904. The data can be organized according to one or more curation tools 906 and stored in the data catalog/lake 914 to be made available to the application factory 916 and/or the learning factory 924. The application factory 916 includes a viewer 918 allowing a system and/or associated user to view and/or access applications available via application services 920 and/or a pipelines catalog 922.

In the example of FIG. 9, the learning factory 924 includes a model catalog 926 including one or more network models (e.g., deep learning-based network models, machine learning-based network machines, etc.) available to the application factory 916 and/or other external system, for example. The learning factory 924 also includes data science 928 including data to form and/or be leveraged by models in the model catalog 926. The example data science 928 includes an architecture catalog 930, data preparation 932, results/reporting 934, training and validation 936, and testing 938 to organize and otherwise pre-process data, train and validate a learning network, report results, and test outcomes, etc. Trained and validated networks are made available for deployment in one or more applications via the model catalog 926, for example.

Figure 10:
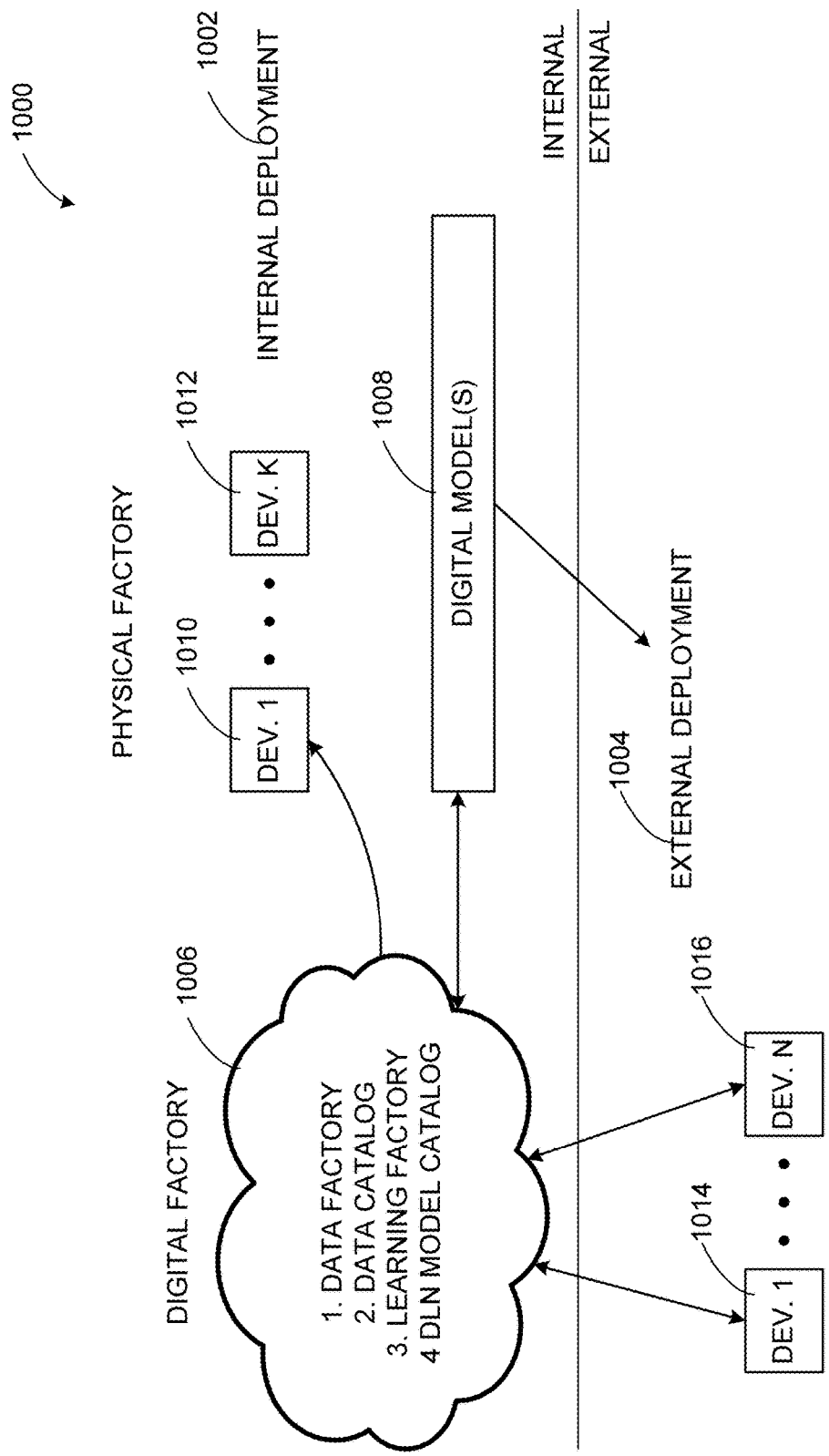
FIG. 10 illustrates an overview of a medical device ecosystem including devices physically deployed internally and externally (physical factory) with a digital factory.

FIG. 10 illustrates an overview of a medical device ecosystem 1000 including devices physically (physical factory) deployed internally 1002 and externally 1004 with a digital factory 1006. As shown in the example of FIG. 10, the digital factory 1006 includes a data factory 902, data catalog 914, learning factory 924, deep learning network-based model catalog 926, etc. The digital factory 1006 provides and/or interacts with one or more digital models 1008 (e.g., deep learning network models, machine learning models, etc.). The digital factory 1006 interacts with a physical factory including a plurality of devices 1010-1016 deployed internally 1002 (e.g., devices 1010 and 1012 and externally 1004 (e.g., devices 10140 and 1016). Devices 1010-1016 are connected to the digital factory 1006 and can upload data to the digital factory 1006, subscribe to model(s) from the catalog 926, update models, etc. Devices 1010, 1012 in internal deployment 1002 can be used for testing and refinement purposes with the digital factory 1006, for example, while devices 1014, 1016 in external deployment 1004 are "live" with deployed models aiding devices 1014, 1016 in decision-making and/or other execution, for example.

Figure 11:
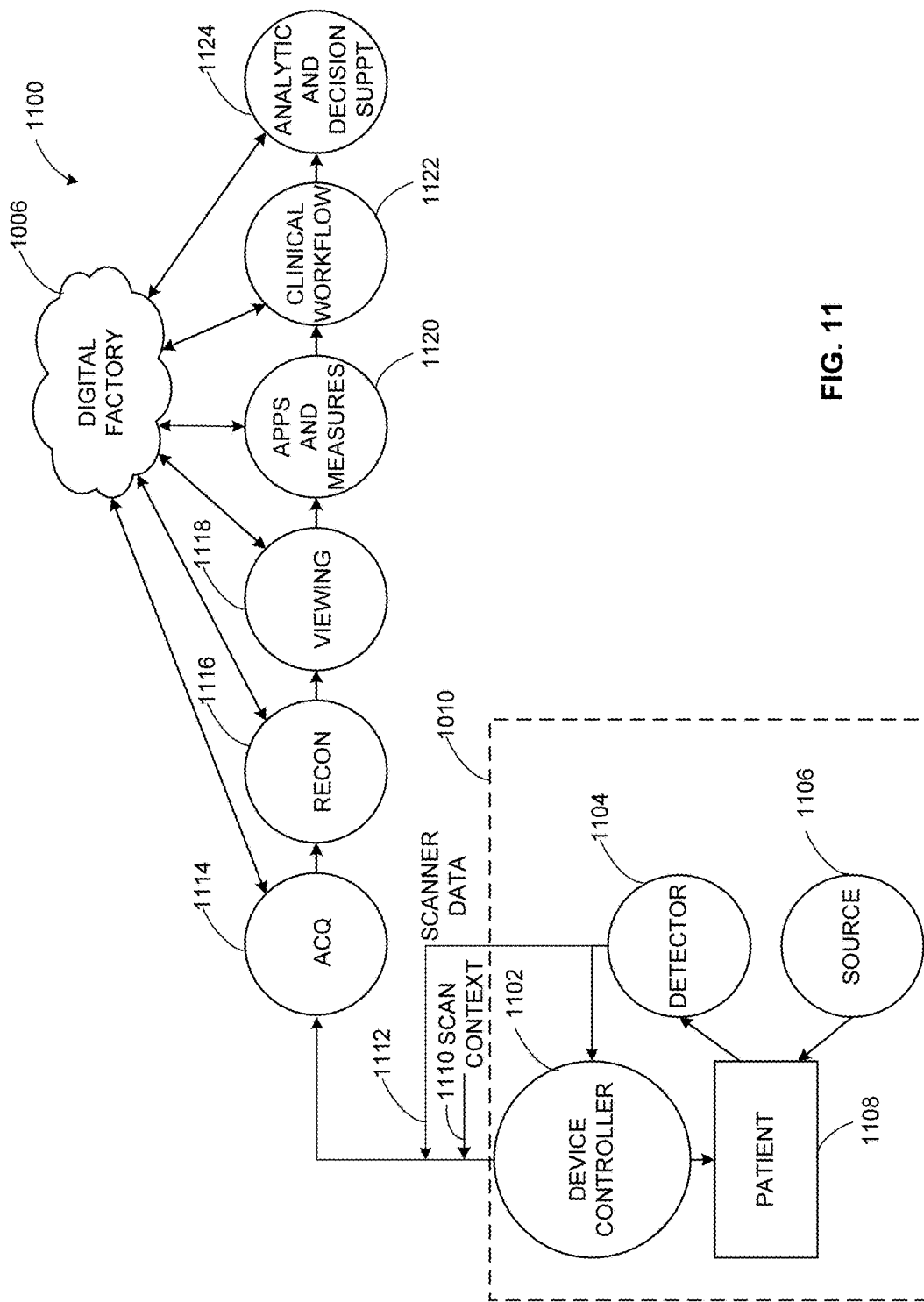
FIG. 11 illustrates an example physical device and its data flow interacting with the digital factory.

FIG. 11 illustrates an example configuration 1100 of the physical device 1010 and its data flow interacting with the digital factory 1006, which can include the data factory 902 and its data catalog 914, data curation 906, as well as the learning factory 924 and its model catalog 926, and the application factory 916 with its application pipelines catalog 922, etc. As shown in the example of FIG. 11, the physical device 1010 (e.g., an imaging scanner) includes a device controller 1102, a detector 1104, and a source 1106 to acquire image data of a patient 1108. The scanner device 1010 provides a scan context 1110 and scanner data 1112 in image acquisition 1114. The acquisition engine 1114 interacts with the digital factory 1006 to model acquisition of image data, etc. Acquired image data is provided for reconstruction 1116, and the reconstruction engine 1116 also interacts with the digital factory 1006 for model-based resources for reconstruction of the acquired image data. The reconstructed image is provided for viewing 1118 in conjunction with an application provided from the digital factory 1006, for example. One or more applications and/or measurements 1120 can be applied to the reconstructed image (e.g., based on models and/or other applications from the digital factory 1006, etc.), for example. Processed image and/or other data can be leveraged in one or more clinical workflows 1122, which in turn leverage applications, data, and models from the digital factory 1006 to facilitate improved and/or automated execution of the clinical workflow(s) 1122. Outcome(s) of the workflow(s) can be provided to analytics and decision support 1124 to drive conclusion(s), recommendation(s), next action(s), model refinement, etc., in conjunction with the digital factory 1006, for example.

Figure 12:
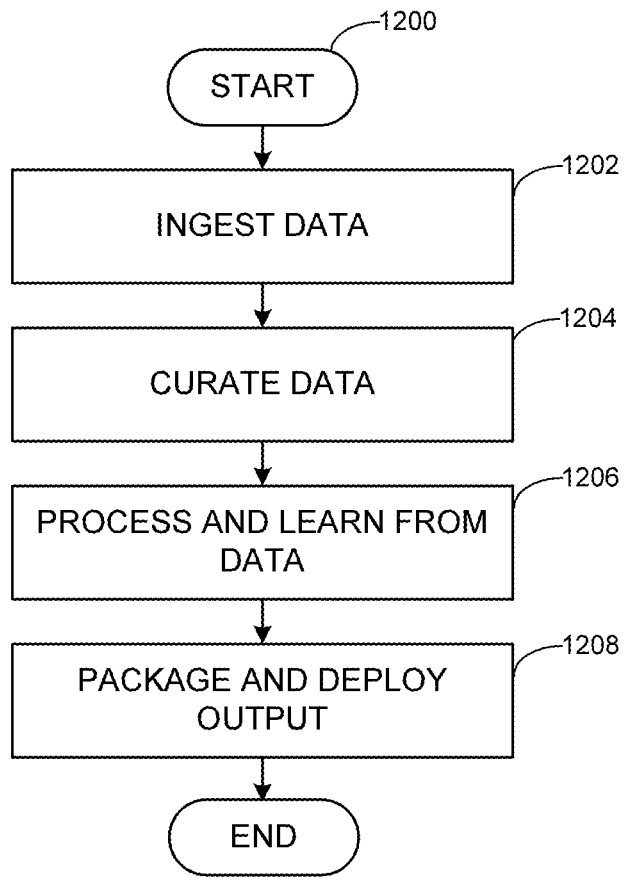
FIG. 12 illustrates a flow diagram of an example method to process and leverage data in a digital factory.

FIG. 12 illustrates a flow diagram of an example method 1200 to process and leverage data in the data factory 902 and learning factory 924. At block 1202, data is ingested (e.g., by bulk 908 and/or continuous 912 ingestion, etc.). At block 1204, the ingested data is curated. For example, one or more data categorization, processing, and/or other curation tools 906 can be applied to organize the ingested data. At block 1206, the curated data is processed and used for learning. For example, the curated data can be analyzed, used to train a deep learning network, etc. At block 1208, output generated from the processed data and based on the learning is packaged and deployed. For example, one or more trained deep learning networks can be cataloged in the model catalog 926 and made available for deployment.

Figure 13:
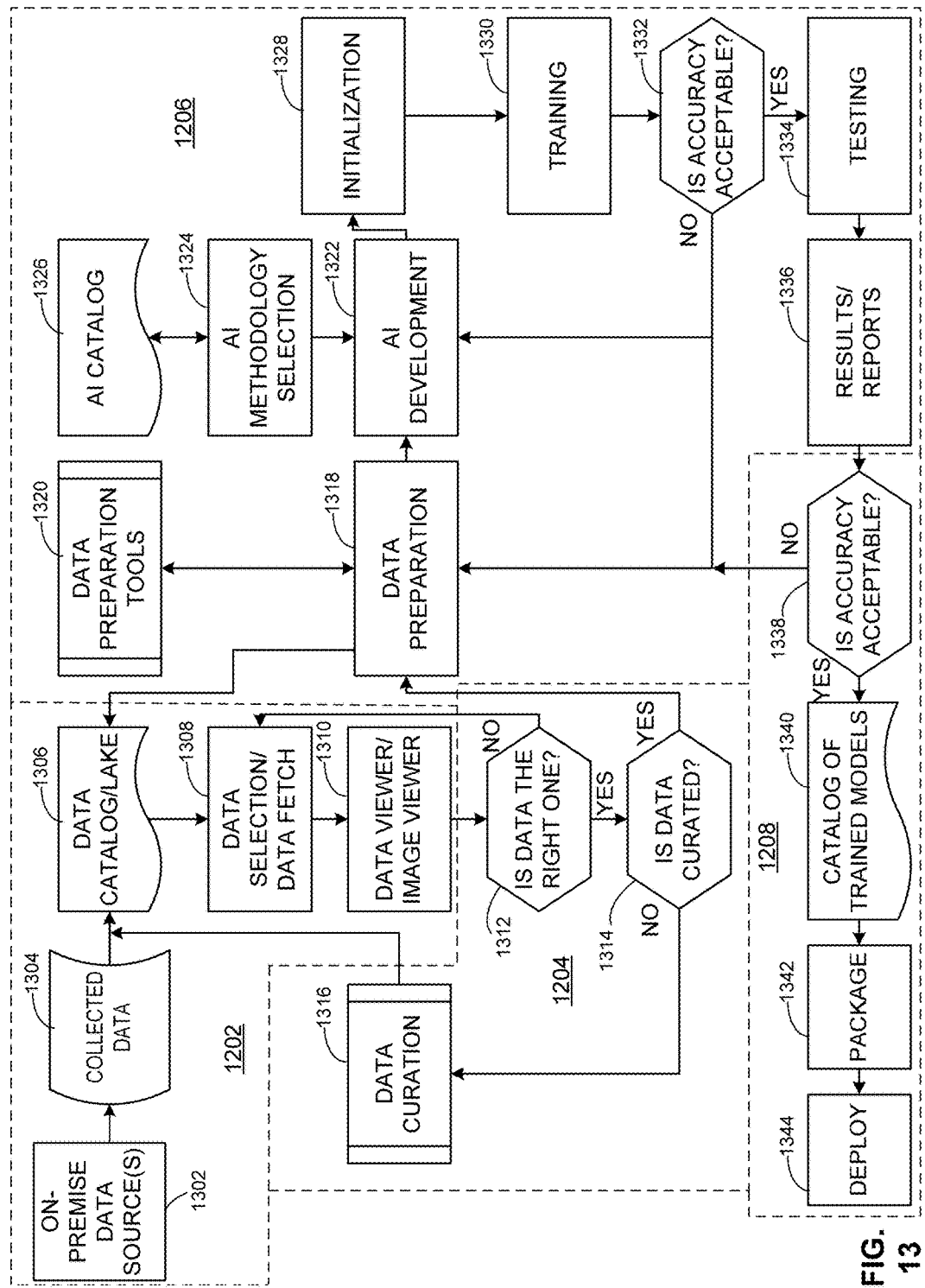
FIG. 13 provides further detail regarding the example method to process and leverage data in the data factory and learning factory.

FIG. 13 provides further detail regarding the example method 1200 to process and leverage data in the data factory 902 and learning factory 924. As shown in the example of FIG. 13, data ingestion 1202 includes extracting data from one or more on-premise data sources 1302 such as a picture archiving and communication system (PACS), vendor-neutral archive (VNA), enterprise archive (EA), imaging scanner, etc. Ingested data is collected and stored 1304 in a data catalog/lake 1306. At block 1308, data is selected and/or fetched for viewing 1310 via the image and/or other data viewer 1310.

FIG. 13 also provides further detail regarding data curation/organization 1204. At block 1312, the selected/fetched data is analyzed to determine if the correct data for the application and/or other request. If not, control reverts to block 1308 to select/fetch different data. If the right data has been selected, then, at block 1314, the data is reviewed to determine whether or not the data is curated. If the data is not curated, then, at block 1316, data curation occurs. For example, data curation involves accurate labeling of data, identification of a region of interest (ROI) with editable bounding box, addition of meta data information, modifying improper pre-curation information, etc., and saving as a new data set. Curated data is provided back to the data catalog 1306. If, at block 1314, the data is curated, then, control shifts to data processing at block 1206.

As shown in more detail in FIG. 13, data processing 1206 includes preparing the data 1318 using one or more data preparation tools 1320. The data is prepared for development of artificial intelligence (AI) (block 1322), such as development of a deep learning network model and/or other machine learning model, etc. Data preparation 1318 (e.g., for training, validation, testing, etc.) includes creation and labeling of data patches, image processing (e.g., crop, squash, etc.), data augmentation to generate more training samples, three-dimensional image processing to provide to a learning network model, database creation and storage (e.g., j son and/or other format), patch image data storage (e.g., .png, .jpeg, etc.), etc. In some examples, a final patch image data dataset is stored in the data catalog/lake 1306.

At block 1324, an AI methodology (e.g., deep learning network model and/or other machine learning model, etc.) is selected from an AI catalog 1326 of available models, for example. For example, a deep learning model can be imported, the model can be modified, transfer learning can be facilitated, an activation function can be selected and/or modified, machine learning selection and/or improvement can occur (e.g., support vector machine (SVM), random forest (RF), etc.), an optimization algorithm (e.g., stochastic gradient descent (SGD), AdaG, etc.) can be selected and/or modified, etc. The AI catalog 1326 can include one or more AI models such as good old fashioned artificial intelligence (GOFAI) (e.g., expert systems, etc.), machine learning (ML) (e.g., SVM, RF, etc.), deep learning (DL) (e.g., convolutional neural network (CNN), recurrent neural network (RNN), long short-term memory (LSTM), generative adversarial network (GAN), etc.), paradigms (e.g., supervised, unsupervised, reinforcement, etc.), etc.

At block 1328, model development is initialized (e.g., using an activation function, weight, bias, hyper-parameters, etc.), and, at block 1330, training of the model occurs (e.g., as described above, etc.). In certain examples, training 1330 is an iterative process including training and validation involving hyper-parameter setup, hyper-parameter search, training/validation set accuracy graph(s), area under the curve (AUC) graphing, intermittent model generating and saving, early and/or manually stop training, etc. At block 1332, an accuracy of the AI model is evaluated to determine whether the accuracy is acceptable. If the accuracy is not acceptable, then control reverts to block 1318 for additional data preparation and subsequent development. If the accuracy is acceptable, then, at block 1334, the AI model is released for testing (e.g., providing additional input(s) and evaluating output(s), etc.). At block 1336, results of the testing are reported. For example, a continuous recording of experimental parameters and outcomes can be provided.

FIG. 13 also provides further example detail regarding packaging and deployment 1208. At block 1338, if the accuracy of the tested model is not acceptable, control reverts to block 1318 for data preparation. If the accuracy of the tested model is acceptable, then, at block 1340, the model is added to a catalog of trained models. At block 1342, one or more of the models in the catalog of trained models is packaged, and, at block 1344, the package is deployed (e.g., to a target site, target system, etc.).

Figure 14:
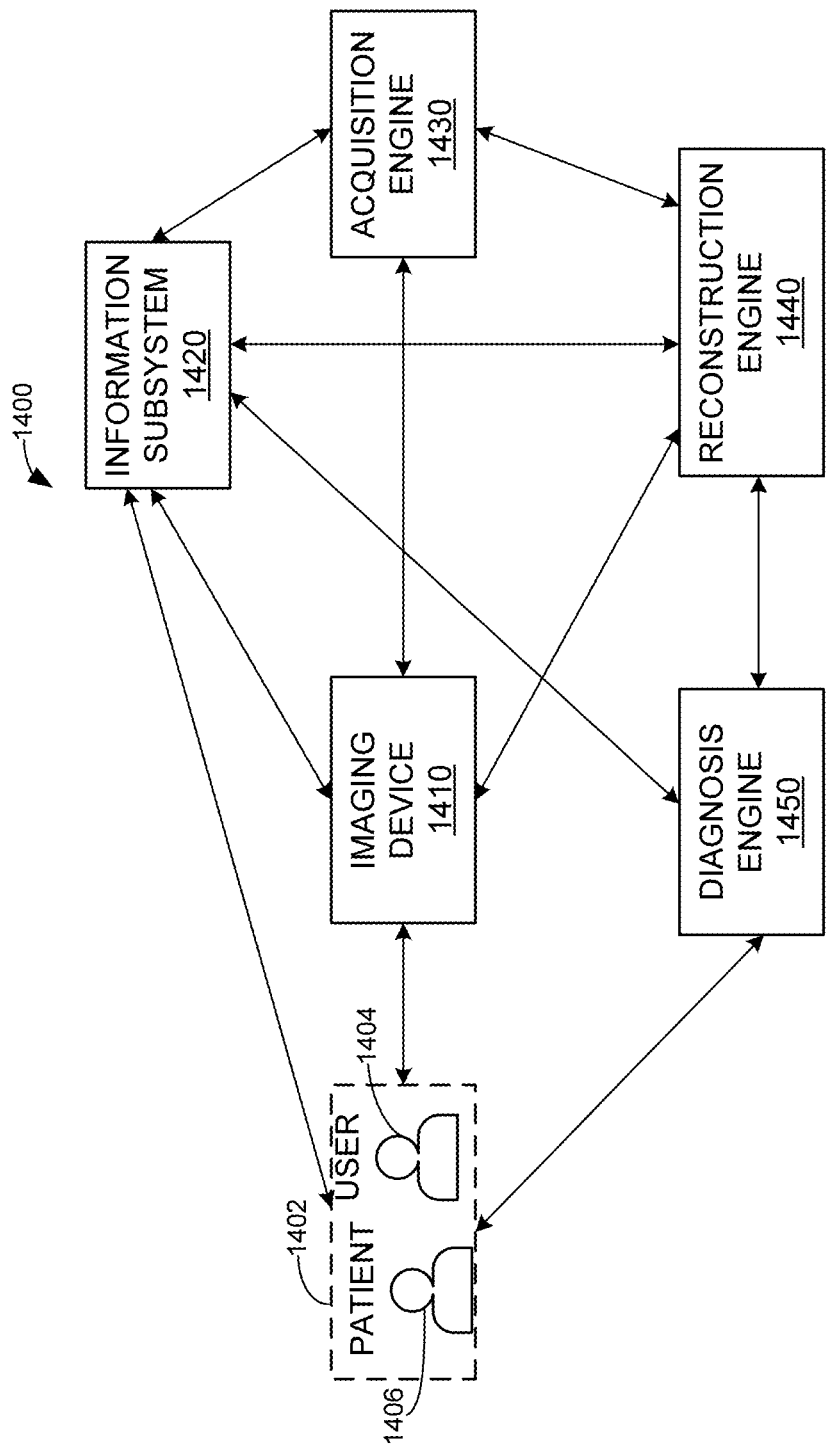
FIG. 14 illustrates an example healthcare system for patient evaluation and diagnosis with deep learning.

Example Improved Healthcare Systems Utilizing Deep and/or Other Machine Learning and Associated Methods FIG. 14 illustrates an example healthcare system 1400 for patient evaluation and diagnosis. The example system 1400 includes an imaging device 1410, an information subsystem 1420, an acquisition engine 1430, a reconstruction engine 1440, and a diagnosis engine 1450 for interaction with humans 1402 such as a user 1404 (e.g., a physician, nurse, technician, and/or other healthcare practitioner, etc.) and a patient 1406. The components of the healthcare system 1400 can be implemented using one or more processors executing hardcoded configuration, firmware configuration, software instructions in conjunction with a memory, etc. For example, one or more components of the system 1400 can include a processor-based system including a combination of hardware and/or software code, routines, modules, or instructions adapted to perform the presently discussed functionality, including performance of various elements of the methods described elsewhere herein. It should be noted that such software routines may be embodied in a manufacture (e.g., a compact disc, a hard drive, a flash memory, a universal serial bus (USB)-based drive, random access memory (RAM), read only memory (ROM), etc.) and configured to be executed by a processor to effect performance of the functionality described herein.

Using the example system 1400, the patient 1404 can be examined by the imaging system 1410 (e.g., CT, x-ray, MR, PET, ultrasound, MICT, single photon emission computed tomography (SPECT), digital tomosynthesis, etc.) based on settings from the information subsystem 1420 and/or acquisition engine 1430. Settings can be dictated and/or influenced by a deployed deep learning network model/device, such as CNN, RNN, etc. Based on information, such as a reason for exam, patient identification, patient context, population health information, etc., imaging device 1410 settings can be configured for image acquisition with respect to the patient 1406 by the acquisition engine 1430, alone or in conjunction with the information subsystem 1420 (e.g., a picture archiving and communication system (PACS), hospital information system (HIS), radiology information system (RIS), laboratory information system (LIS), cardiovascular information system (CVIS), etc.). The information from the information subsystem 1420 and/or acquisition engine 1430, as well as feedback from the imaging device 1410, can be collected and provided to a training deep learning network model to modify future settings, recommendations, etc., for image acquisition, for example. Periodically and/or upon satisfaction of certain criterion, the training deep learning network model can process the feedback and generate an updated model for deployment with respect to the system 1400.

Acquired or raw image data from the imaging device 1410, alone or in conjunction with additional patient history, patient context, population health information, reason for exam, etc., is provided to the reconstruction engine 1440 to process the data to generate a resulting image. The reconstruction engine 1440 uses the information and acquired image data to reconstruct one or more two-dimensional (2D) and/or three-dimensional (3D) images of the patient 1406. Method(s) for reconstruction, reconstruction engine 1440 setting(s), etc., can be set and/or influenced by a deep learning network, such as a CNN, RNN, etc. For example, slice thickness, image quality, etc., can be determined and modified using a deep learning network.

In certain examples, raw image data can be preprocessed by the reconstruction engine 1440. Preprocessing may include one or more sub-processes, such as intensity correction, resembling, filtering, etc. In certain examples, anatomical markers in the image data may be detected, and an image grid may be created. Based on the anatomical markers and the image grid, the reconstruction engine can register the image data (e.g., according to a reference coordinate system, etc.). Following registration, features of interest in the image data may be extracted.

In certain examples, particular features that are of interest in the raw image data may vary depending on a particular disease or condition of interest. For example, in diagnosing neurological conditions, it may be useful to extract certain features of brain image data to facilitate diagnosis. Further, in some examples, it may be desirable to determine the thickness of the cerebral cortex of a patient or of one or more reference individuals.

Certain examples process raw data acquired by the imaging device 1410 and acquisition engine 1430 and provide the raw image data to the reconstruction engine 1440 to produce one or both of a) a machine-readable image provided to the diagnostic decision support engine 1450 and b) a human-viewable image displayed for user diagnosis.

For example, while image reconstruction is primarily performed for human consumption, pre-reconstruction data can be used by a machine which does not care whether or not data has been reconstructed to be viewable by a human. Thus, pre-reconstruction data can be processed differently for human consumption and for machine consumption. Machine-readable image data can be processed by the reconstruction engine 1440 according to indicators of a given disease, for example, so that the reconstruction engine 1440 and/or the diagnosis engine 1450 can identify patterns indicative of the disease without performing reconstruction (e.g., in the raw image data acquisition state). Thus, in some examples, the reconstruction engine 1440 can perform a diagnosis with the diagnosis engine 1450 rather than relying on the user 1404 to interact with the diagnosis engine 1450 to make a clinical diagnosis.

Image output from the reconstruction engine 1440 can then be provided to the diagnosis engine 1450. The diagnosis engine 1450 can take image data from the reconstruction engine 1440 and/or non-image data from the information subsystem 1420 and process the data (e.g., static data, dynamic data, longitudinal data, etc.) to determine a diagnosis (and/or facilitate a diagnosis by the user 1404) with respect to the patient 1406. Data provided to the diagnosis engine 1450 can also include data from one or more patient monitors, such as an electroencephalography (EEG) device, an electrocardiography (ECG or EKG) device, an electromyography (EMG) device, an electrical impedance tomography (EIT) device, an electronystagmography (ENG) device, a device adapted to collect nerve conduction data, and/or some combination of these devices.

In some examples, the diagnosis engine 1450 processes one or more features of interest from the image data to facilitate diagnosis of the patient 1406 with respect to one or more disease types or disease severity levels. Image data may be obtained from various sources, such as the imaging device 1410, the information subsystem 1420, other device, other database, etc. Further, such image data may be related to a particular patient, such as the patient 1406, or to one or more reference individuals of a population sample. The image data can be processed by the reconstruction engine 1440 and/or the diagnosis engine 1450 to register and extract features of interest from the image, for example.

Information can then be output from the diagnosis engine 1450 to the user 1404, the information subsystem 1420, and/or other system for further storage, transmission, analysis, processing, etc. Information can be displayed in alpha-numeric data format and tabulated for further analysis and review (e.g., based on metric analysis, deviation metric, historical reference comparison, etc.), for example. Alternatively or in addition, data can be presented holistically for analysis via heat map, deviation map, surface matrix, etc., taken alone or with respect to reference data, for example. U.S. Pat. Nos. 9,271,651, 8,934,685, 8,430,816, 8,099,299, and 8,010,381, commonly owned by the present assignee, provide further disclosure regarding an example holistic analysis.

A patient diagnosis can be provided with respect to various patient disease types and/or patient conditions, as well as associated severity levels, while also providing decision support tools for user-diagnosis of patients. For example, patient clinical image and non-image information can be visualized together in a holistic, intuitive, and uniform manner, facilitating efficient diagnosis by the user 1404. In another example, patient cortical deviation maps and reference cortical deviation maps of known brain disorders can be visualized along with calculation of additional patient and reference deviation maps, and the combination of such maps with other clinical tests, to enable quantitative assessment and diagnosis of brain disorders.

Making a diagnosis is a very specialized task, and even highly-trained medical image experts conduct a subjective evaluation of an image. Due to this inherent subjectivity, diagnoses can be inconsistent and non-standardized. The diagnosis engine 1450 can employ a deep learning network, such as a CNN, RNN, etc., to help improve consistency, standardization, and accuracy of diagnoses. Additional data, such as non-image data, can be included in the deep learning network by the diagnosis engine 1450 to provide a holistic approach to patient diagnosis.

In certain examples, the components of the system 1400 can communicate and exchange information via any type of public or private network such as, but not limited to, the Internet, a telephone network, a local area network (LAN), a cable network, and/or a wireless network. To enable communication via the network, one or more components of the system 1400 includes a communication interface that enables a connection to an Ethernet, a digital subscriber line (DSL), a telephone line, a coaxial cable, or any wireless connection, etc.

In certain examples, the information subsystem 1420 includes a local archive and a remote system. The remote system periodically and/or upon a trigger receives the local archive via the network. The remote system may gather local archives (e.g., including the local archive from the information subsystem 1420, reconstruction engine 1440, diagnosis engine 1450, etc.) from various computing devices to generate a database of remote medical image archives. In some examples, the remote system includes a machine learning algorithm to analyze, correlate, and/or process information to develop large data analytics based on archives from various clinical sites based. For example, a plurality of images can be gathered by the remote system to train and test a neural network to be deployed to automatically detect regions of interest in images (e.g., auto-contour, etc.).

FIG. 15 illustrates a further detailed view of an example improved healthcare system 1500 for patient evaluation and diagnosis. In the example of FIG. 15, the imaging device 1410, information system 1420, acquisition engine 1430, reconstruction engine 1440, and diagnosis engine 1450 are configured with a plurality of deep learning networks 1522, 1532, 1542, a system health module 1550, and a system design engine 1560.

Figure 15A:
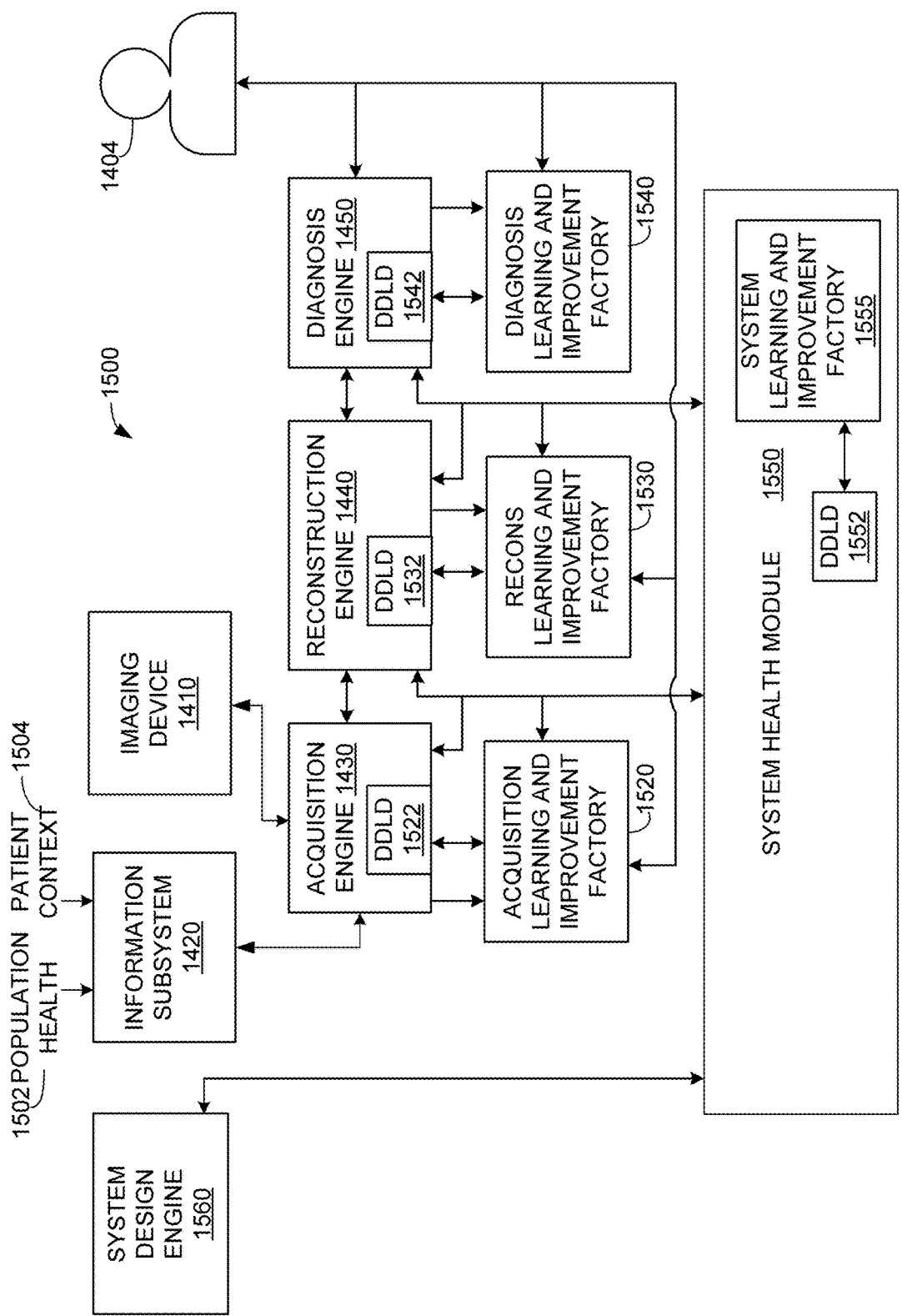
FIG. 15A illustrates a further detailed view of an example improved healthcare system for patient evaluation and diagnosis.

As shown in the example of FIG. 15A, each of the acquisition engine 1430, reconstruction engine 1440, and diagnosis engine 1450 communicates with an associated learning and improvement factory 1520, 1530, 1540 for feedback evaluation and training and, also, includes a deployed deep learning device 1522, 1532, 1542, respectively (e.g., a CNN, RNN, other deep neural network, deep belief network, recurrent neural network, other machine learning, etc.) to aid in parameter selection, configuration, data processing, outcome determination, etc. While the devices 1522, 1532, 1542 are depicted with respect to the engines 1430, 1440, 1450 in the example of FIG. 15A, the devices 1522-1542 can be incorporated in the factories 1520-1540 as described above with respect to FIG. 8A, for example. The learning and improvement factories 1520, 1530, 1540 implement a process of learning, feedback, and updating the deployed deep learning devices 1522, 1532, 1542, for example. The engines 1430, 1440, 1450 provide feedback to one or more of the factories 1520-1540 to be processed and train an updated model to adjust settings, adjust output, request input, etc. Periodically and/or otherwise upon reaching a threshold, satisfying a criterion, etc., the factories 1520, 1530, 1540 can replace and/or re-deploy the deep learning network model for the devices 1522, 1532, 1542, for example.

The deployed deep learning network (DLN) devices 1522, 1532, 1542 and associated factories 1520, 1530, 1540 can be implemented using a processor and a memory particularly configured to implement a network, such as a deep learning convolutional neural network, similar to the example networks 100, 200, 300 described above. Each factory 1520, 1530, 1540 can be taught by establishing known inputs and outputs associated with an intended purpose of the network 1520, 1530, 1540. For example, the acquisition learning and improvement factory 1520 is tasked with improving image acquisition settings for the acquisition engine 1430 to provide to the imaging device 1410 based on patient information, reason for examination, imaging device 1410 data, etc. The reconstruction learning and improvement factory 1530 is tasked with determining image quality and reconstruction feedback based on acquired image data, imaging device 1410 settings, and historical data, for example. The diagnosis learning and improvement factory 1540 is tasked with assisting in patient diagnosis based on patient information, image reconstruction information and analysis, and a clinical knowledge base, for example.

For each factory 1520, 1530, 1540, data sets are established for training, validation, and testing. A learning fraction to train and validate the factory 1520, 1530, 1540 and its included training network model is a multiple of the validate and testing fraction of the available data, for example. The factory 1520, 1530, 1540 can be initialized in a plurality of ways. For example, if no prior knowledge exists about the component 1430, 1440, 1450 associated with the respective factory 1520, 1530, 1540, the training deep learning network of the factory 1520, 1530, 1540 can be initialized using random numbers for all layers except the final classifier layer of the network, which can be initialized to zero. If prior knowledge exists, network layers of the factory 1520, 1530, 1540 can be initialized by transferring the previously learned values to nodes in the network. Alternatively, even when prior knowledge does not exist, network layers can be initialized using a stacked auto-encoder technique.

In certain examples, feedback to and/or from the factory 1520, 1530, and/or 1540 is captured in storage (e.g., stored and/or buffered in a cloud-based storage, etc.) including input data, actual output, and desired output. When a sufficient amount of feedback is received, the training DLN of the corresponding factory 1520, 1530, 1540 is retrained in an incremental fashion or newly trained using the additional feedback data (e.g., based on original feedback data plus additional feedback data, etc.) depending on the amount of feedback data received. Once (re)trained, the network model from the factory 1520-1540 can be used to generate and/or re-deploy the deployed network model for the deep learning device 1522-1542.

In certain examples, an au encoder technique provides unsupervised learning of efficient codings, such as in an artificial neural network. Using an auto-encoder technique, a representation or encoding can be learned for a set of data. Auto-encoding can be used to learn a model of data and/or other dimensionality reduction using an encoder and decoder to process the data to construct layers (including hidden layers) and connections between layers to form the neural network.

For example, an auto-encoder can be implemented using a 3-layer neural network including an input layer, a hidden layer, and an output layer. In this example, the input layer and output layer include the same number of nodes or units but not all hidden layer nodes are connected to all nodes in the input layer. Rather, each node in the hidden layer is connected to input nodes in a localized region of the input layer. As with the example of FIG. 3, the auto-encoder network can model portions of an image to detect local patterns and/or features with a reduced number of parameters, for example. The example auto-encoder can include two components: 1) an encoder function $f$ that maps an input x to a hidden layer representation $h=f(x)$, and 2) a decoder function g that maps h to reconstruct x for the output layer. Using weights and biases, the auto-encoder can be used to generate a new representation of the input x through the hidden layer h.

Backpropagation or backward propagation of errors can be used in batches (e.g., mini-batches, etc.) involving pre-determined sets (e.g., small sets) of randomly selected data from the learning data set using stochastic gradient descent (SGD) to minimize or otherwise reduce a pre-determined cost function while trying to prevent over-training by regularization (e.g., dropouts, batch normalization of mini-batches prior to non-linearities, etc.) in the auto-encoder network. Using mini-batches, rather than an entire training data set, the analysis should converge more quickly. After leveraging an initial amount of training data to train the DLNs of the factories 1520, 1530, 1540 (e.g., a multiple of validation data, etc.), for each subsequent batch of data during training, validation is performed and validation error is monitored. Learning parameters with the best validation error are tracked and accumulated through the process to improve future training, for example. Parameters that provide the least error (e.g., hyper-parameters) are selected after validation. Additionally, learning iterations can be stopped if the validation error does not improve after a predetermined number of iterations. If validation error improves, iterations can continue until the validation error stabilizes. Then, parameters can be selected for the DLNs of the factories 1520, 1530, 1540, for example.

Hyper parameters represent variables to be adjusted in the factories 1520, 1530, 1540. In some examples, hyper parameters are selected for a particular learning algorithm prior to applying that learning algorithm to the neural network. Hyper parameters can be fixed by hand and/or determined by algorithm, for example. In some examples, data used to select hyper parameter values (e.g., training data) cannot be used to test the DLNs of the factories 1520, 1530, 1540. Thus, a separate test data set is used to test the network once the hyper parameter values are determined using training data, for example.

Output and/or other feedback from the acquisition engine 1430, reconstruction engine 1440, and the diagnosis engine 1450 are provided to the system health module 1550 to generate an indication of the health of the system 1500 based on an image quality indicator from the reconstruction engine 1440, a diagnosis confidence score provided by the diagnosis engine 1450, and/or other feedback generated by the deep learning networks 1522, 1532, 1542 via the acquisition engine 1530, reconstruction engine 1440, and/or diagnosis engine 1450, for example. The output/feedback provided by the acquisition engine 1430, reconstruction engine 1440, and diagnosis engine 1450 to the system health module 1550 is also provided to the learning and improvement factories 1520, 1530 to update their network models based on the output and/or other feedback. Thus, the learning and improvement factory 1520, 1530 for a prior stage can be updated using feedback from a subsequent stage 1530, 1540, etc. The system health module 1550 can include its own deployed deep learning device 1552 and system learning and improvement factory 1555 for modeling and adjusting a determination of system health and associated metric(s), recommendation(s), etc.

Deep Learning Networks identify patterns by learning the patterns. Learning includes tuning the parameters of the network using known inputs and outputs. The learned network can predict the output given a new input. Thus, during the learning process, networks adjust the parameters in such a way to represent the mapping of generic input-to-output mappings and, as a result, they can determine the output with very high accuracy.

Inputs to and outputs from the deployed deep learning device (DDLD) 1522, 1532, 1542 can vary based on the purpose of the DDLD 1522, 1532, 1542. For the acquisition DDLD 1522, for example, inputs and outputs can include patient parameters and imaging device 1410 scan parameters. For the reconstruction DDLD 1532, for example, inputs and outputs can include projection domain data and reconstructed data using a computationally intensive algorithm. For the diagnosis DDLD 1542, input can include a two-dimensional and/or three-dimensional image, and output can include a marked visualization or a radiology report, for example. A type of network used to implement the DDLD 1522, 1532, 1542 can vary based on target task(s). In certain examples, the corresponding acquisition, reconstruction, or diagnosis learning and improvement factory 1520, 1530, 1540 can be trained by leveraging non-medical, as well as medical, data, and the trained model is used to generate the DDLD 1522, 1532, 1542.

For example, the reconstruction engine 1440 provides feedback to the acquisition learning and improvement factory 1520, which can re-deploy the DDLD 1522 and/or otherwise update acquisition engine 1430 parameters based on image quality and/or other output characteristics determined by the reconstruction engine 1440. Such feedback can be used by the acquisition engine 1430 to adjust its settings when modeled and processed by the DDLD 1522. The reconstruction engine 1440 can also provide feedback to its own reconstruction learning and improvement factory 1530. The acquisition engine 1430 can also provide feedback to its own acquisition learning and improvement factory 1520.

Similarly, for example, the diagnosis engine 1450 provides feedback to the learning and improvement factory 1530 for the reconstruction engine 1440, which can re-deploy the DDLD 1532 and/or otherwise update reconstruction engine 1440 parameters based on a confidence score associated with diagnosis and/or other output characteristics determined by the diagnosis engine 1450. Such feedback can be used by the reconstruction engine 1440 to adjust its settings when modeled and processed by the DDLD 1532.

One or more of the learning and improvement factories 1520, 1530, 1540 can also receive feedback from one or more human users 1404 (e.g., based on using the outcome of the diagnosis engine 1450 to diagnose and treat the patient 1406, etc.). By chaining feedback between engine(s) 1430-1450, factories 1520-1540d the system health module 1550, engines 1430, 1440, 1450 can learn and improve from the current and/or subsequent phase of the imaging and diagnosis process.

Thus, certain examples consider a reason for examination of a patient in conjunction with an acquisition deployed deep learning device 1522, a reconstruction deployed deep learning device 1532, a diagnosis deployed deep learning device 1542, and a system health deployed deep learning device 1552 to improve configuration and operation of the system 1500 and its components such as the imaging device 1410, information subsystem 1420, acquisition engine 1430, reconstruction engine 1440, diagnostic engine 1450, etc. Deep learning can be used for image analysis, image quality (e.g., quality of clarity, resolution, and/or other image quality feature, etc.), etc.

A learning data set can be applied as input to each learning and improvement factory 1520, 1530, 1540. The learning data set can include an image data set with assigned image quality metric (e.g., a scale of 1-5, etc.) as an output, for example. The system 1500 and its components evaluate one or more metrics as outputs and feedback to the factories 1520, 1530, 1540 for continued improvement. Automating inputs and outputs to the factories 1520, 1530, 1540, 1555, as well as the DDLDs 1522, 1532, 1542, 1552, facilitates continued system operation and improvement.

In certain examples, using a 3D topography of medical images from different imaging modalities (MRI, CT, x-ray, etc.) can provide changes in classification, convolution, etc. A model can be formed by the respective DDLD 1522, 1532, 1542. The model(s) can be adjusted based on anatomy, clinical application, patient information (e.g., data and/or scout scan, etc.), patient history, etc.

In certain examples, each DDLD 1522, 1532, 1542 determines a signature. For example, the DDLD 1522, 1532, 1542 determines signature(s) for machine (e.g., imaging device 1410, information subsystem 1420, etc.) service issues, clinical issues related to patient health, noise texture issues, artifact issues, etc. The DDLD 1522, 1532, 1542 can determine a signature indicative of one of these issues based on input, learned historical patterns, patient history, preference, etc.

Certain examples provide metrics for validation and regressive testing via the DDLD 1522, 1532, 1542. Output can also include notice(s) from signature classification(s). Certain examples provide an image quality matrix/metrics for human visual inspection. Certain examples provide an image quality matrix/metrics for non-human interpretation (e.g., big data analytics, machine learning, etc.).

Certain examples can provide an output for quality control (e.g., provide a number or value to reflect an overall quality of an imaging scan, etc.). Certain examples provide an output for rescan assistance (e.g., deciding whether a rescan is warranted, etc.). Certain examples can be used to automate protocol selection and/or new protocol customization (e.g., new protocol parameters can be computed based on an image quality metric, etc.).

In certain examples, the output can be used to improve development of hardware systems. For example, if an issue is identified in a medical system (e.g., an artifact caused by hardware, etc.), a next iteration can propose a solution to fix or alleviate the issue. In certain examples, clinical context is added to the DDLD 1522, 1532, 1542 to facilitate clinical decision making and support.

Output from the DDLD 1522, 1532, 1542 can be used to improve development of algorithms such as algorithms used to measure quality. By providing feedback to the factories 1520, 1530, 1540, a change to an algorithm can be modeled and tested via a DLN of the respective factory 1520, 1530, 1540 to determine how the change can impact output data. Capturing and modeling changes in a feedback loop can be used with nonlinear, iterative reconstruction of acquired image data, for example.

Certain examples facilitate monitoring and adjustment of machine health via automated diagnosis by the system 1500. Service decisions can be made (e.g., an automated service that the machine can run on itself, a call for manual human repair, etc.) based on deep learning output information. Machine-based decision support can be provided, and one or more machine-specific signatures indicative of an issue can be investigated and adjusted.

Certain examples can extrapolate additional information about a patient based on patient information input from the information subsystem 1420 combined with output from the acquisition engine 1430, reconstruction engine 1440, and diagnosis engine 1450 in conjunction with their DDLDs 522, 1532, 1542. In certain examples, based on patient history, medical issue, past data sets, etc., the DDLD 1522 can help determine which acquisition settings are best to acquire an image data set, and the DDLD 1532 can help determine what protocol is the best selection to provide image data set output. Patient behavior, such as movement during scans, how their body handles contrast, the timing of the scan, perceived dose, etc., can be gathered as input by the DDLD 1522, for example, to determine image device 1410 acquisition settings, for example.

Certain examples provide an end-to-end image acquisition and analysis system including an improved infrastructure chaining multiple DDLDs 1522, 1532, 1542 together. For example, raw data acquired by the imaging device 1410 and acquisition engine 1430 is processed and provided to the reconstruction engine 1440 to produce one or both of a) a machine-readable image provided to the diagnostic decision support engine 1450 and b) a human-viewable image displayed for user diagnosis. Different DLNs are provided for acquisition, reconstruction, and diagnosis, and each DDLD 1522, 1532, 1542 has different input, different processing, and different output.

Thus, the example system 1500 creates one or more images using interconnected DDLDs 1522, 1532, 1542 and corresponding engines 1430, 1440, and links the image(s) to decision support via the diagnosis engine 1450 and DDLD 1542 for diagnosis. Real-time (or substantially real time given processing and transmission delay) feedback (e.g., feed forward and feed back between learning and improvement factories 1520, 1530, 1540 and engines 1430, 1440, 1450) loops are formed in the example system 1500 between acquisition and reconstruction and between diagnosis and reconstruction, for example, for ongoing improvement of settings and operation of the acquisition engine 1430, reconstruction engine 1440, and diagnosis engine 1450 (e.g., directly and/or by replacing/updating the DDLD 1522, 1532, 1542 based on an updated/retrained DLN, etc.). As the system 1500 learns from the operation of its components, the system 1500 can improve its function. The user 1404 can also provide offline feedback (e.g., to the factory 1520, 1530, 1540, etc.). As a result, each factory 1520, 1530, 1540 learns differently based on system 1500 input as well as user input in conjunction with personalized variables associated with the patient 1406, for example.

In certain examples, the diagnosis engine 1450 operates with the DDLD 1542, which is trained, validated and tested using sufficiently large datasets that can adequately represent variability in the expected data that the diagnosis engine 1450 is to encounter. The diagnosis learning and improvement factory 1540 can be used to refine its output as more input is provided to it by the diagnostic engine 1450 and/or reconstruction engine 1440, for example. The factory 1540 can then replace the deployed DLN of the DDLD 1542, for example.

The diagnosis engine 1450 identifies pattern(s) in one or more images based on big data from patients in a population (e.g., retrieved from the information subsystem 1420) to suggest a diagnosis of the patient 1406 to the user 1404. The example diagnosis engine 1450 highlights area(s) for user 1404 focus and can predict future area(s) of interest based on big data analytics, for example. Even if the image is presented in a suboptimal way, the diagnosis engine 1450 can provide a patient-dependent answer, rather than a determination one dependent on that particular imaging scan. The diagnosis engine 1450 can analyze the image and identify trouble spot(s) that the user 1404 may not see based on settings used in acquisition, reconstruction, analysis, etc. Output can be automatic to trigger another system/device and/or can be presented as a suggestion to the user 1404. Data output from the system 1500 can be provided to a cloud-based system, for example. Output can be provided to the system learning and improvement factory 1555 of the system health module 1550 such that the system health module 1550 learns when actions should be taken to maintain or improve health of the system 1500.

The system health module 1550 receives input from a plurality of components 1430, 1440, 1450 and processes the input to determine whether changes should be made to the system 1500. Based on exposure to and learning from issues affecting the acquisition engine 1430, reconstruction engine 1440, diagnosis engine 1450, etc., the system health module 1550 provides an output to the acquisition engine 1430 to modify behavior of the imaging device 1410 and/or other system component. The system health module 1550 also provides an output for the system design engine 1560, which uses the identified problem/issue to modify design of the imaging device 1410 and/or system 1400, 1500 component, for example.

Figure 15B:
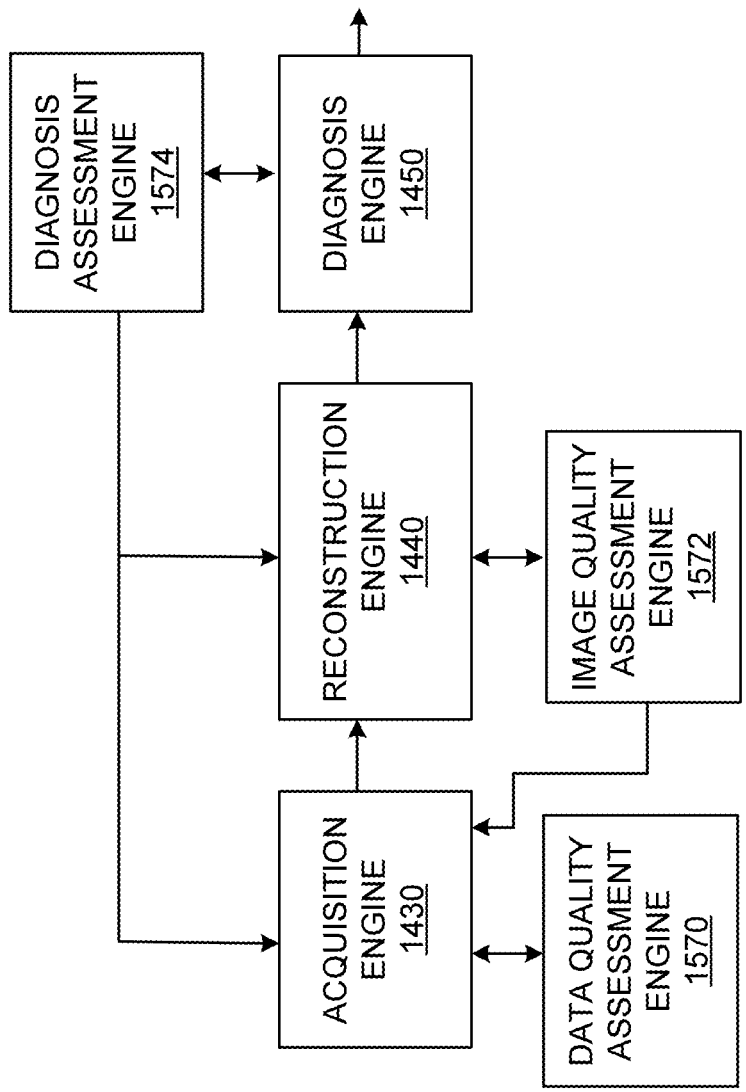
FIG. 15B illustrates an example system implementation in which the acquisition engine, reconstruction engine, and diagnosis engine are accompanied by a data quality assessment engine, an image quality assessment engine, and a diagnosis assessment engine.

FIG. 15B illustrates an example system implementation 1501 in which the acquisition engine 1430, reconstruction engine 1440, and diagnosis engine 1450 are accompanied by a data quality assessment engine 1570, an image quality assessment engine 1572, and a diagnosis assessment engine 1574. In the configuration 1501 of FIG. 15B, each engine 1430, 1440, 1450 receives direct feedback from an associated assessment engine 1570, 1572, 1574. In certain examples, the acquisition engine 1430, reconstruction engine 1440, and/or diagnosis engine 1450 receives feedback without having to update their associated deployed deep learning modules 1522, 1532, 1542. Alternatively or in addition, the data quality assessment engine 1570, image quality assessment engine 1572, and diagnosis assessment engine 1574 provide feedback to the engines 1430-1450. Although direct connections are depicted in the example of FIG. 15B for the sake of simplicity, it should be understood that each of the deep learning-based feedback modules 1570-1574 has an associated training image database including different classes of example conditions, an associated learning and improvement factory module, an orchestration module, and a trigger for associated parameter update and restart, for example.

Thus, the acquisition engine 1430 may receive feedback from the data quality assessment engine (DQ-AE) 1570, the image quality assessment engine (IQ-AE) 1572, and/or the diagnosis assessment engine (Diag-AE) 1574, for example. The reconstruction engine 1440 may receive feedback from the IQ-AE 1572 and/or the Diag-AE 1574, for example. The diagnosis engine 1450 may receive feedback from the Diag-AE 1574, for example.

Figure 16:
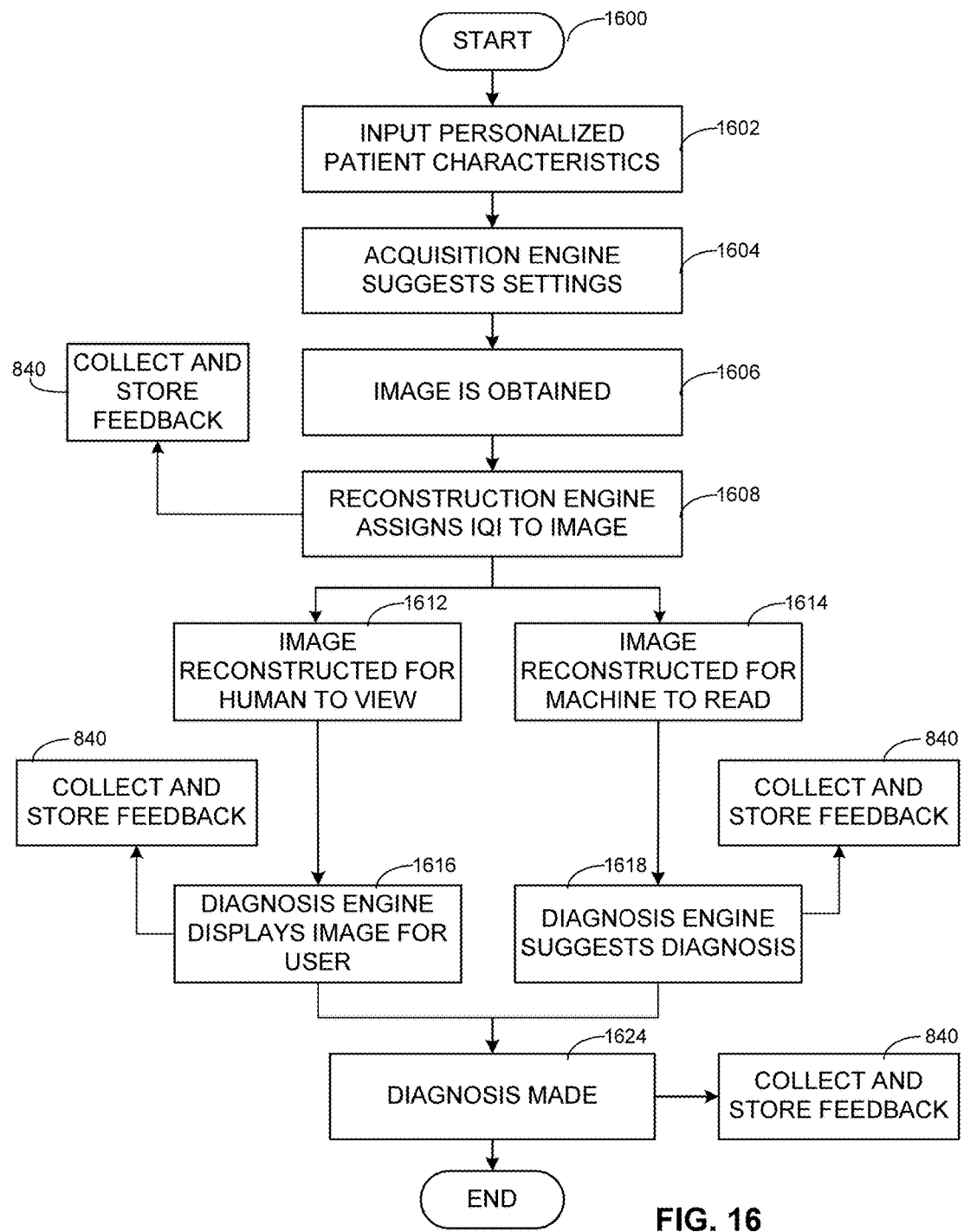
FIG. 16 illustrates a flow diagram of an example method for improved image acquisition, processing, and patient diagnosis.

FIG. 16 illustrates a flow diagram of an example method 1600 for improved image acquisition, processing, and patient diagnosis. At block 1602, personalized patient characteristics are input into the acquisition engine 1430. For example, a clinician may enter personalized patient characteristics into the acquisition engine 1430. Alternatively or in addition, personalized patient characteristics can be provided for an identified patient to be image via the information subsystem 1420. At block 1604, the acquisition engine 1430 suggests one or more imaging device 1410 settings based on the input personalized patient characteristics as well as learned information extracted from the DDLD 1522, for example.

Thus, using information particular to the patient 1406 as well as information learned by the DDLD 1522, improved settings for image acquisition by the imaging device 1410 can be determined. At block 1606, one or more images of the patient 1406 are obtained by the imaging device 1410. The images are obtained according to the settings provided by the acquisition engine 1430. The settings can be automatically configured at the imaging device 1410 by the acquisition engine 1430 and/or manually input/overridden by the user 1404 (e.g., a clinician, radiologist, technician, etc.).

At block 1608, the reconstruction engine 1440 receives raw image data from the acquisition engine 1430 and processes the image data to assign image quality metric(s). The image quality (IQ) metric can be a comprehensive image quality indicator (IQI) and/or one or more particular metrics regarding aspects of image quality. For example, specific image quality metrics include spatial resolution, noise, etc. At block 840, described above, feedback generated by the reconstruction engine 1440 can be collected and stored. Thus, lessons learned by the system 1500 from the reconstruction of the acquired image data can be fed back into the acquisition learning and improvement factory 1520 for further refinement of imaging device 1410 settings. After conducting an image quality analysis on the image data, the reconstruction engine 1440 processes the image data to reconstruct an image for further review and analysis. This resulting image or images can be processed for automated machine analysis, such as computer-aided diagnosis (CAD), or for human viewing of the image.

Configuration settings from the reconstruction DDLD 1532 is used to determine whether the acquired image data is to be processed for machine analysis and/or human viewing. At block 1612, the image is reconstructed for human review the display of the resulting image. At block 1614, the image data is processed to produce an image suitable for machine evaluation and analysis of the image. With the machine-analyzable image, for example, features of the image can be optimized for computer detection but need not be visually appreciable to a user, such as a radiologist. For the human-viewable image, however, features of the image anatomy should be detectable by a human viewer in order for the reconstruction to be useful.

At block 1616, if the human viewable image has been reconstructed, the reconstruction agent 1440 provides the image to the diagnosis engine 1450 which displays the image to the user 1404. At block 1618, the machine analyzable image has been generated, then the reconstruction engine 1440 provides the machine-readable image to the diagnosis engine 1450 automated processing and suggested diagnosis based on the image data from the diagnosis engine 1450.

At block 840, feedback regarding the human-viewable image and/or machine-suggested diagnosis is provided from the diagnosis engine 450. At block 1624, a diagnosis of the patient 1406 is made based on human viewing of the image by the user 1404 and/or automated processing of the image by the diagnosis engine 1450, taken alone or in conjunction with data from the DDLD 1542 and/or information subsystem 1420.

The diagnosis can be provided to the user 1404, the patient 1406, and/or routed to another system, for example. For example, at block 840, feedback is provided from the diagnosis engine 1450 and/or the user 1404. Feedback can also be provided to the system design engine 1560. Feedback from the user 1404, diagnosis engine 1450, reconstruction engine 440, acquisition engine 1430, and/or other system 1500 component can be provided to the system health module 1560 to compute an indication of system 1500 health.

Figure 17:
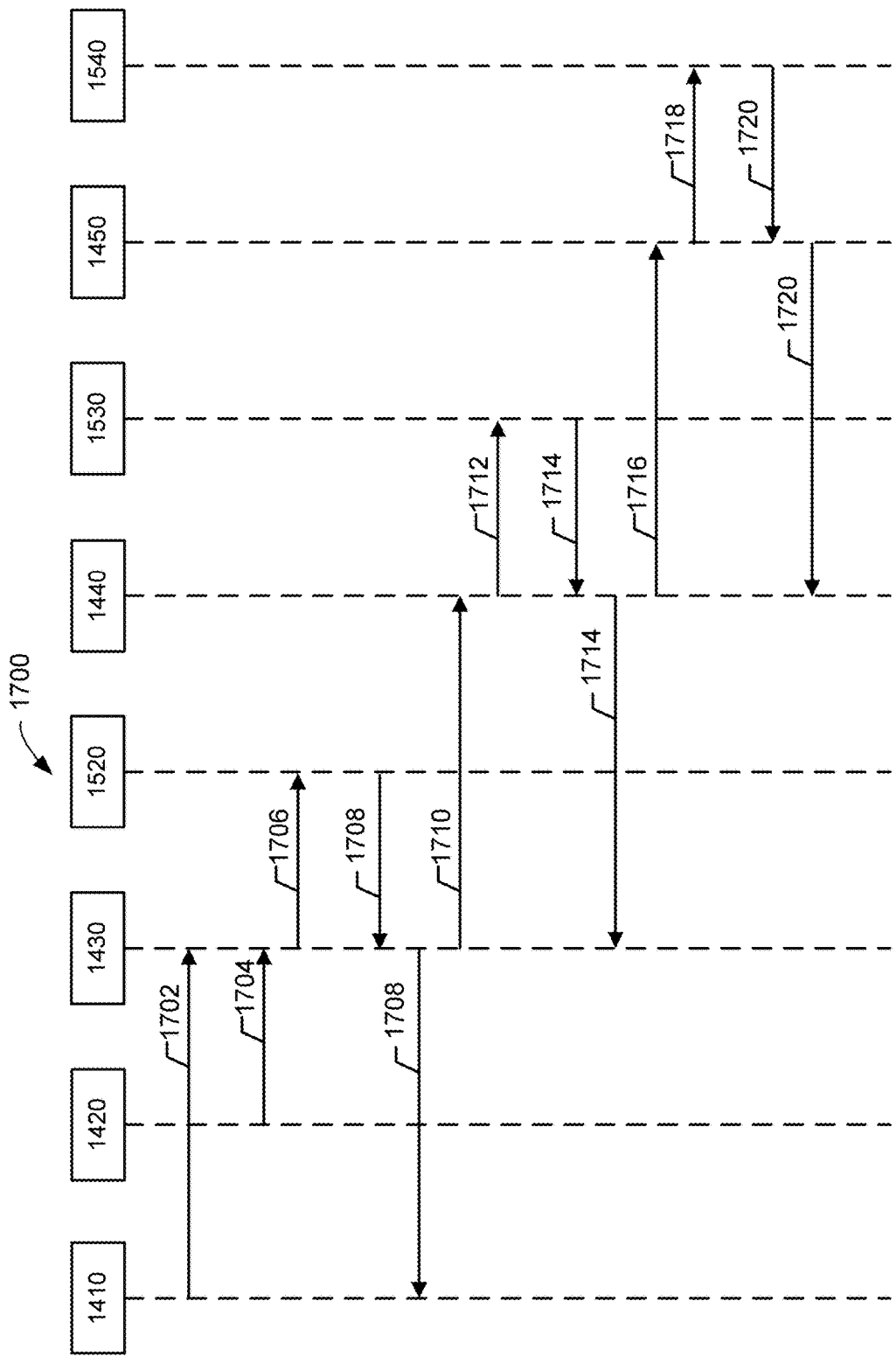
FIG. 17 illustrates an example data flow and transformation of information as it flows among the components of the example system of FIG. 15A.

FIG. 17 illustrates an example data flow and transformation of information 1700 as it flows among the components of the system 1500. As shown in the example of FIG. 17, a first data 1702 is provided by the imaging device 1410 to the acquisition engine 1430. A second data 1704 is provided by the information subsystem 1420 to the acquisition engine 1430. The acquisition engine 1430 sends third data 1706 including the first data 1702 and/or second data 1704 to the acquisition DDLD 1522. The acquisition DDLD 1522 transforms the third data 1706 into fourth data 1708, and sends the fourth data 1708 back to the acquisition engine 1430. The acquisition engine 1430 sends the fourth data 1708 to the imaging device 1410. The acquisition engine 1430 sends fifth data 1710 to the reconstruction engine 1440.

The reconstruction engine 1440 sends sixth data 1712 including the fifth data 1710 to the reconstruction DDLD 1532. The DDLD 1532 transforms the sixth data 1012 into seventh data 1714, and sends the seventh data 1714 back to the reconstruction engine 1440. The reconstruction engine 1440 sends the seventh data 1714 to the acquisition engine 1430. The reconstruction engine 1440 sends eighth data 1716 to the diagnosis engine 1450.

The diagnosis engine 1450 sends ninth data 1718 including the eighth data 1716 to the diagnosis DDLD 1542. The DDLD 1542 transforms the ninth data 1718 into tenth data 1720, and sends the tenth data 1720 back to the diagnosis engine 1450. The diagnosis engine 1450 sends the tenth data 1720 to the reconstruction engine 1440.

Thus, certain examples transform patient information, reason for examination, and patient image data into diagnosis and other healthcare-related information. Using machine learning, such as deep learning networks, etc., a plurality of parameters, settings, etc., can be developed, monitored, and refined through operation of imaging, information, and analysis equipment, for example. Using deep learning networks, for example, learning/training and testing can be facilitated before the imaging system is deployed (e.g., in an internal or testing environment), while continued adjustment of parameters occurs "in the field" after the system has been deployed and activated for use, for example.

Certain examples provide core processing ability organized into units or modules that can be deployed in a variety of locations. Off-device processing can be leveraged to provide a micro-cloud, mini-cloud, and/or a global cloud, etc. For example, the micro-cloud provides a one-to-one configuration with an imaging device console targeted for ultra-low latency processing (e.g., stroke, etc.) for customers that do not have cloud connectivity, etc. The mini-cloud is deployed on a customer network, etc., targeted for low-latency processing for customers who prefer to keep their data in-house, for example. The global cloud is deployed across customer organizations for high-performance computing and management of information technology infrastructure with operational excellence.

Using the off-device processing engine(s) (e.g., the acquisition engine 1430, reconstruction engine 1440, diagnosis engine 1450, etc., and their associated deployed deep learning network devices 1522, 1532, and/or 1542, etc.), acquisition settings can be determined and sent to the imaging device 1410, for example. For example, purpose for exam, electronic medical record information, heart rate and/or heart rate variability, blood pressure, weight, visual assessment of prone/supine, head first or feet first, etc., can be used to determine one or more acquisition settings such as default field of view (DFOV), center, pitch, orientation, contrast injection rate, contrast injection timing, voltage, current, etc., thereby providing a "one-click" imaging device. Similarly, kernel information, slice thickness, slice interval, etc., can be used to determine one or more reconstruction parameters including image quality feedback, for example. Acquisition feedback, reconstruction feedback, etc., can be provided to the system design engine 1560 to provide real-time (or substantially real-time given processing and/or transmission delay) health analytics for the imaging device 1410 as represented by one or more digital models (e.g., deep learning models, machine models, digital twin, etc.). The digital model(s) can be used to predict component health for the imaging device 1410 in real-time (or substantially real time given a processing and/or transmission delay).

Each deep learning network can be trained using curated data with associated outcome results. For example, data regarding stroke (e.g., data from onset to 90 days post-treatment, etc.) can be used to train a neural network to drive to predictive stroke outcomes. Thus, operational, clinical, treatment, and therapy "biomarkers" can be identified for best and/or other improved outcomes. Similarly, lung cancer data can be analyzed by a deep learning network including department to department tracking from screening, diagnosis, treatment planning, treatment response, final outcome, etc., for one or more imaging devices 1410 including CT, PET/CT, nuclear medicine, etc.

For image acquisition, given one or more known inputs and one or more known outputs, acquisition settings can be determined automatically to train the acquisition learning and improvement factory 1520 for predictable output to generate the deployed DDLD 1522. When the output of settings for the imaging device 1410 reaches a threshold of reliability, the acquisition engine 1430 can be certified to provide acquisition settings for the imaging device 1410 (e.g., as integrated into the imaging device 1410 and/or as a separate device in communication with the imaging device 1410, etc.). Settings can be used and modified without further customer training or testing. As a result, a user can obtain high quality image acquisitions and avoid a bad or subpar set of image acquisitions. Acquisition settings and the associated DDLD 1522 can be trained to respond only to good quality image acquisitions, and setting adjustments can be suggested by the DDLD 1522 when a bad quality image is obtained. Thus, from a user perspective, one button is pushed to consistently acquire a fast image exam. Using a purpose for the examination in conjunction with patient parameters, a DICOM header for a desired output, and an indication of the desired output obtained from an existing medical exam which corresponds to imaging device 1410 parameters for successful and/or unsuccessful data sets, the DDLD 1522 can recognize good image quality and suggest corresponding settings as default settings, as well as, when user makes a mistake in configuring the imaging device 1410 for image acquisition, suggest settings to recover from the mistake. Over time, the acquisition learning and improvement factory 1520 can evolve and improve based on learned successes and failures to re-train and re-deploy an improved DDLD 1522 to drive to the acquisition engine 1430, for example.

In certain examples, cloud-based protocols can be captured and managed to automate selection of protocol and/or rules to make best practices available via the cloud.

Quality feedback can also be obtained from image reconstruction. Without human review, a good or bad image can be identified and associated with one or more image quality metrics and/or indicators by the DDLD 1532, for example. Such an image quality index (IQI) and/or other metric can be generated by the reconstruction engine 1440 using DDLD 1532 and used to make a medical decision with or without human review, for example. The generated index/metric can be used to inform the DDLD 1532 and/or user 1404 regarding whether the imaging device 1410 is acquiring good or bad quality images and under what conditions, etc.

In deep learning, testing can assess quality of images automatically for known cases at a certain level. Feedback based on an analysis of image quality compared to imaging device 1410 settings can be provided to the system design engine 1560 to facilitate further imaging device 1410 development, for example. Using the system design engine 1560 and learning and improvement factories 1520 and/or 1530, a decline in image quality can be detected and used to evaluate system health 1550, including health of the imaging device 1410, for example. While a human user 1404 may not detect a gradual decrease in quality, deep learning provides an objective, unbiased evaluation for early detection.

In certain examples, a diagnostic index or detectability index can be calculated similar to an image quality indicator. The diagnostic index can be a measure of under what conditions the user 1404 can make a diagnosis given a set of data. The DDLD 1542 and associated diagnosis learning and improvement factory 1540 analyze current and historical data and system 1500 parameters from other components to provide a consistent indication for the user 1404, patient 1406, type of condition, type of patient, type of examination, etc. Once the training DLN of the factory 1540 is trained, for example, the model can be deployed to the DDLD 1542, and diagnosis data can be compared to image quality. Feedback can be provided to the reconstruction engine 1440, acquisition engine 1430, the associated learning and improvement factories 1520, 1530, and/or the user 1404 to provide further indication of image quality and/or a corresponding change in imaging device 1410 settings for acquisition, for example.

In some examples, instead of or in addition to a numerical indication of patient diagnosis, a holistic analysis/display can be provided. Using a holistic analysis, visual indication, such as a heat map, deviation map, etc., can be provided to visualize how the patient 1406 fits or does not fit with trends, characteristics, indicators, etc., for a particular disease or condition. In certain examples, as the factory 1540 improves in its diagnosis learning, the visual representation can improve. Using a holistic approach with the diagnosis engine 1450 and its DDLD 1542, data from a plurality of sources is processed and transformed into a form in which a human can identify a pattern. Using deep learning, the DDLD 1542 can process thousands of views of the data, where a human user 1404 may only be able to reasonably process ten before losing focus.

The deep learning process of the DDLD 1542 can identify pattern(s) (and potentially enable display an indication of an identified pattern via the diagnosis engine 1450) rather than the human user 1404 having to manually detect and appreciate (e.g., see) the pattern. Multi-variant analysis and pattern identification can be facilitated by the DDLD 1542, where it may be difficult for the human user 1404 to do so. For example, the DDLD 1542 and diagnosis engine 1540 may be able to identify a different pattern not understandable to humans, and/or a pattern that is understandable to humans but buried in too many possibilities for a human to reasonably review and analysis. The DDLD 1542 and diagnosis engine 1450 can provide feedback in conjunction with human review, for example.

In certain examples, the holistic analysis feeds into the diagnosis made by the user 1404, alone or in conjunction with the diagnosis engine 1450. The diagnosis engine 1450 and its DDLD 1542 can be used to provide a second opinion for a human decision as a legally regulated/medical device, for example. In certain examples, the diagnosis engine 1450 can work in conjunction with the DDLD 1542 to provide automated diagnosis.

Example Analytics Framework

Figure 18:
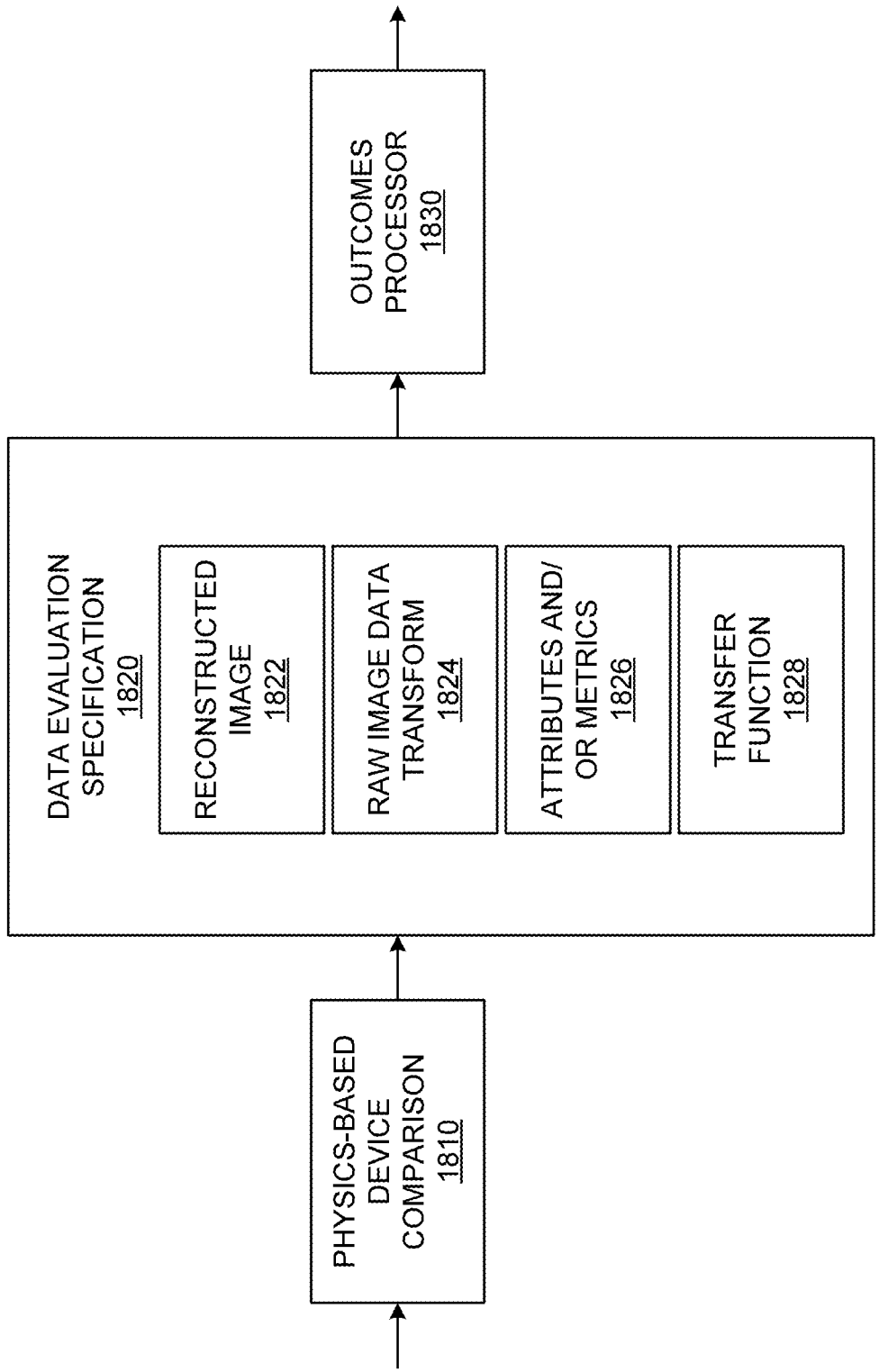
FIG. 18 illustrates an example healthcare analytics framework for image acquisition, image reconstruction, image analysis, and patient diagnosis using the example systems of FIGS. 14-15B.

In certain examples, a healthcare analytics framework 1800 can be provided for image acquisition, image reconstruction, image analysis, and patient diagnosis using the example systems 1400, 1500 (including the acquisition engine 1430, reconstruction engine 1440, and diagnosis engine 1450, along with their associated DDLDs 1520-150 and learning and improvement factories 1520-1540). As shown in the example of FIG. 18, input, such as imaging device 1410 parameter, reconstruction engine 1440 parameter, etc., is provided to a physics-based device comparison 1810. The device comparison 1810 can be facilitated by the DDLD 1522 and/or other machine learning network, for example. The input is used by the device comparison 1810 to compare the imaging device 1410 to other imaging devices of the same and/or different types from the same and/or different vendor. A deep learning and/or other machine learning technique can be used to learn and assist in developing the comparison based on device 1410 characteristics, image acquisition parameter, reconstruction setting, etc. For example, the DDLD 1522 and/or 1532 can be used for the device comparison 1810 to develop a profile and/or other comparison of the imaging device 1410 to other imaging scanners.

The device 1410 comparison information is provided to a data evaluation specification 1820. The data evaluation specification 1820 can also be implemented by the DDLD 1522 and/or 1532 and/or a separate processor, for example. The data evaluation specification 1820 processes a reconstructed image 1822 from the reconstruction engine 1440 and a transform of raw image data 1824 from the acquisition engine 1430 and the imaging device 1410. Machine learning methods such as deep learning, dictionary learning (e.g., build a dictionary from other images and apply the dictionary definitions to the current image, etc.), etc., can be applied to the reconstructed and/or raw image data to define image attributes and/or task-based image quality evaluation metrics 1826. Image quality information (e.g., noise, resolution, etc.) can be extracted directly from the image and raw image data (e.g., with region of interest, without using specific phantoms and/or modulation transfer function (MTF), etc.) using deep learning and/or other machine learning technique. Additionally, one or more task-based metrics (e.g., detectability, etc.) can be extracted from the data using deep learning and/or other machine learning. The attribute(s) and metric(s) 1826 form a specification for data evaluation based on the device-based comparison.

In certain examples, a model can be formed. The data evaluation specification 1820 constructs a transfer function 1828 to mathematically represent or model inputs to and outputs from the data evaluation specification 1820. The transfer function 1828 helps to generate and model the image attributes and/or task-based image quality evaluation metrics 1826. In certain examples, variation can be modeled based on analytics such calculating a nodule volume, estimating a source of variations from image(s) directly, etc., and modeled variation can be used to standardize the reconstructed image and improve analytics.

Based on the model and transfer function 1828 providing analytics and modification of image data, an outcomes processor 1830 determines one or more clinical outcomes. For example, information can be provided to the outcomes processor 1830 to facilitate (e.g., via the diagnosis engine 1450) user determination of a clinical outcome. Alternatively or in addition, the outcomes processor 1830 can generate a machine determination (e.g., using the diagnosis engine 1450 and DDLD 1542 with image analysis) of clinical outcome.

Thus, for example, image resolution quality has traditionally been measured using a phantom(s) (e.g., a wire, edge, etc.) in conjunction with MTF. However, many radiologists can tell that a clinical image has a lower resolution by observing the image. The deep learning and/or other machine network learns to mimic this observation through repeated exposure and analysis, for example. For example, using information from the device comparison 1810 in conjunction with the reconstructed image 1822, standardization transform 1824, etc., the data evaluation specification 1820 can enable the reconstruction engine 1440 and its DDLD 1532, for example, to compute image attributes and recalibrate transformation to work with the diagnosis engine 1450 and its DDLD 1542 to provide analytics to clinicians and to identify acceptable or unacceptable resolution in the image with respect to a range, threshold, etc., that is defined and/or learned by the DDLD 1542, for example. If the resolution is unacceptable, then the DDLD 1522 can be updated via the learning and improvement factory 1520, and acquisition engine 1430 settings are adjusted, for example.

Image Acquisition Examples

Figure 19:
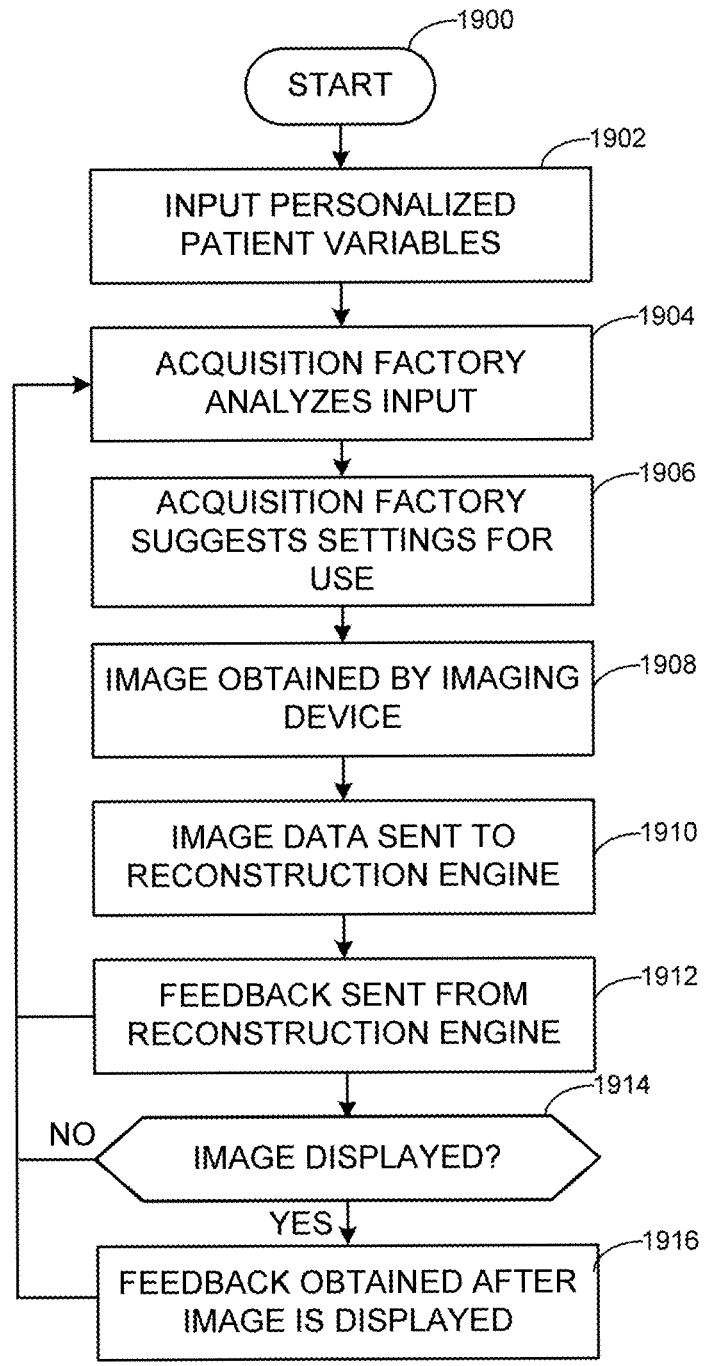
FIG. 19 illustrates a flow diagram of an example method for image acquisition.

FIG. 19 illustrates a flow diagram of an example method 1900 for image acquisition using the imaging device 1410 and the image acquisition engine 1430. At block 1902, personalize patient variables are input to the acquisition engine 1430. Personalized patient variables can include patient height, patient weight, imaging type, reason for exam, patient health history, etc. For example, a clinician may enter personalized patient characteristics into the acquisition engine 1430. Alternatively or in addition, personalized patient characteristics can be provided for an identified patient to be image via the information subsystem 1420.

At block 1904, the acquisition deployed deep learning network device 1522 analyzes the input to the acquisition engine 1430. For example, the DDLD 1522 processes patient parameters, prior imaging device 1410 scan parameters, etc., to generate imaging device 1410 settings for image acquisition. Using a CNN, RNN, autoencoder network, and/or other deep/machine learning network, the DLN 520 leverages prior acquisitions in comparison to current imaging device 1410 settings, patient information, reason for exam, patient history, and population health information, etc., to generate a predictive output. Relationships between settings, events, and results can be explored to determine appropriate imaging device 1410 settings, ideal or preferred acquisition settings based on type of exam and type of patient, changes to imaging device 1410 design, etc. Settings can include intensity or radiation dosage settings for sufficient (versus poor and/or versus high quality, etc.) image quality, etc. Settings can include acquisition type, duration, angle, number of scans, position, etc.

At block 1906, the acquisition engine 1430 suggests one or more imaging device 1410 settings based on the input personalized patient characteristics as well as learned information extracted from the DDLD 1522, for example. As described above, output from the DDLD 1522 can be organized as one or more parameters or configuration settings for the imaging device 1410 to obtain images of the patient 1406. Thus, using information particular to the patient 1406 as well as information learned by the deployed deep learning network device 1522, improved settings for image acquisition by the imaging device 1410 can be determined. Based on the reason for exam, particular patient information, and existing imaging device 1410 settings, the acquisition DDLD 1522 can generate suggested settings for use by the acquisition engine 1430 to obtain image data from the patient 1406 via the imaging device 1410. The settings can be automatically applied by the acquisition engine 1430 to the imaging device 1410 and/or manually entered/overridden by the user 1404, for example.

At block 1908, one or more images of the patient 1406 are obtained by the imaging device 1410. The images are obtained according to the settings provided by the acquisition engine 1430. The settings can be automatically configured at the imaging device 1410 by the acquisition engine 1430 and/or manually input/overridden by the user 1404 (e.g., a clinician, radiologist, technician, etc.), for example.

At block 1910, acquired image data is sent to the reconstruction engine 1440 (e.g., to be reconstructed into a human-viewable image and/or machine-processed, etc.). The reconstruction engine 1440 (using the DDLD 1532) can generate an image quality (IQ) metric to be a comprehensive image quality indicator (IQI) and/or one or more particular metrics regarding aspects of image quality associated with the acquired raw image data. For example, specific image quality metrics include spatial resolution, noise, etc.

At block 1912, feedback from the reconstruction engine 1440 is provided to the acquisition learning and improvement factory 1520 to improve the DDLD 520 (e.g., generate a new DDLD 1522 for deployment with the acquisition engine 1430) for imaging device 1410 settings generation and recommendation. Thus, lessons learned by the system 1500 from the reconstruction of the acquired image data can be fed back into the acquisition learning and improvement factory 1520 (and/or the image quality assessment engine 1572, etc.) for further refinement of network operation and resulting improvement in imaging device 1410 settings. The feedback ensures an ongoing improvement to the DDLD 1522 (via the factory 1520) and, as a result, to the settings provided to the imaging device 1410 for image acquisition for various patients 1406.

At block 1914, if the image is not displayed, then no additional feedback is obtained. However, if the image is displayed, then, at block 1916, additional feedback is provided to the acquisition learning and improvement factory 1520. For example, one or more of the reconstruction DDLD 1532, diagnosis engine 1450, diagnosis DDLD 1542, user 1404, etc., can provide further feedback to the acquisition learning and improvement factory 1520 (and/or the image quality assessment engine 1572, etc.) to improve its learning and data processing. For example, feedback regarding kernel used, noise reduction setting, slice thickness, interval, etc., can be provided.

In certain examples, the acquisition engine 1430 and associated DDLD 1522 can be implemented as a device that can be connected to the imaging device 1410 to configure the operation of the imaging device 1410 for image acquisition. The acquisition configuration device can be used by a technician or installer on-site, sold to a customer for their own operation of the device, etc.

Figure 20:
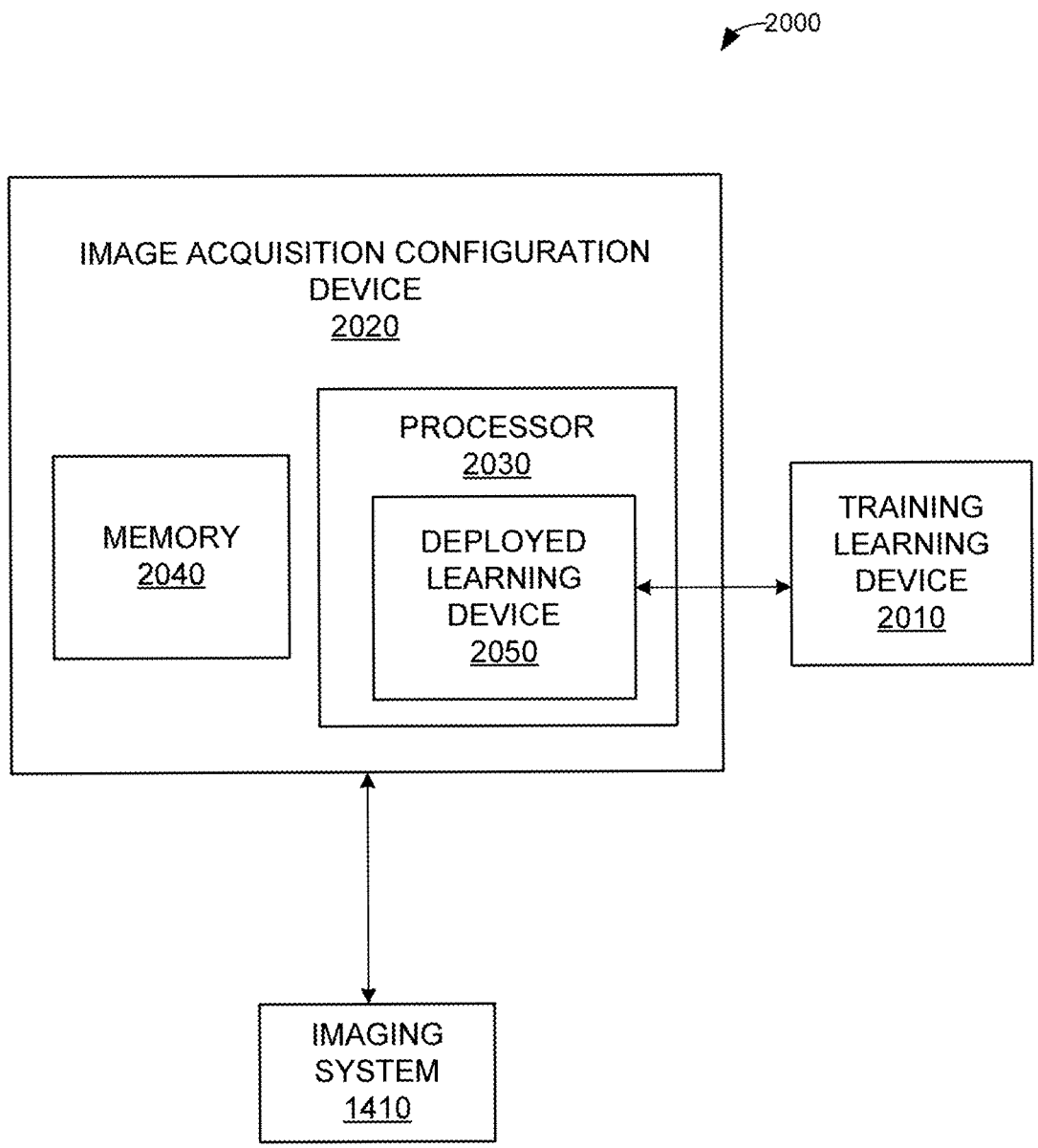
FIG. 20 illustrates example image acquisition configuration system.

FIG. 20 illustrates example image acquisition configuration system 2000 including a training learning device 2010 and an image acquisition configuration device 2020 communicating with the imaging system 1401. The image acquisition configuration device 2020 includes a processor 2030 and a memory 2040. The processor 2030 of the device 2020 instantiates a deployed deep learning device 2050.

In certain examples, the image acquisition configuration device 2020 is initially configured using a first set of imaging system configuration parameters determined by training and testing a prior set of parameters using the training learning device 2010. The device 2020 also includes its own deployed learning device 2050 to be generated using the training learning device 2010 to assist the image acquisition configuration device in determining configuration parameters based on system operation, patient input, and/or etc. The device 2050 operates with the configuration device 2020 while the training device 2010 receives feedback and continues to evolve. The training device 2010 can re-deploy the deployed learning device 2050 when certain criterion is satisfied (e.g., threshold of feedback collected, margin of deviation between device 2050 outcome and modeled device 2010 outcome, etc.). The devices 2010, 2050 can be implemented such as described above, for example.

The device 2020 and its initial parameters can be deployed using the training learning device 2010 once the network of the device 2010 has been trained (e.g., reaches a reliability threshold associated with imaging device 1410 configuration parameters for a type of patient, type of examination, type of image acquisition, image quality threshold, etc.). Until the configuration device 2020 is generating relevant, reliable settings recommendations for the imaging device 1410, the training device 2010 continues to provide recommendations and adjustments and incorporates feedback on inefficiencies, inaccuracies, etc., to continue to learn and refine parameter selection for a given examination purpose, patient type, condition type, dosage, safety threshold, operating condition, etc., and to redeploy the deployed learning device 2050.

Once the learning device 2050 has been deployed, and the configuration device 2020 has been validated as having sufficient reliability and quality, the image acquisition configuration device 2020 can be released for deployment and installation at a customer site (e.g., for use by a technician associated with the imaging device 1410 manufacturer, by the customer directly, etc.). The device 2020 can be deployed to physical connect or "plug in" to the imaging device 1410 (e.g., by wire, cable, connector, etc. Alternatively or in addition, the image acquisition configuration device 2020 can communicate wirelessly (e.g., via Bluetooth™ Bluetooth Low Energy (BLE™), near field communication (NFC), Wi-Fi™, etc.) with the imaging device 1410 to transmit settings to the imaging device 1410 and receive feedback from the imaging device 1410. Feedback is used by the training learning device 2010 to continue to learn, modify, and improve setting recommendations, for example, during operation of the devices 1410, 2020. The device 2020 can also communicate with the reconstruction engine 1440 and/or other image processing workstation to obtain image quality feedback for images resulting from image data acquisition by the imaging device 1410. The training device 2010 uses this feedback as well to train further to respond to good quality and to make suggestions for bad quality image acquisition, for example.

Figure 21:
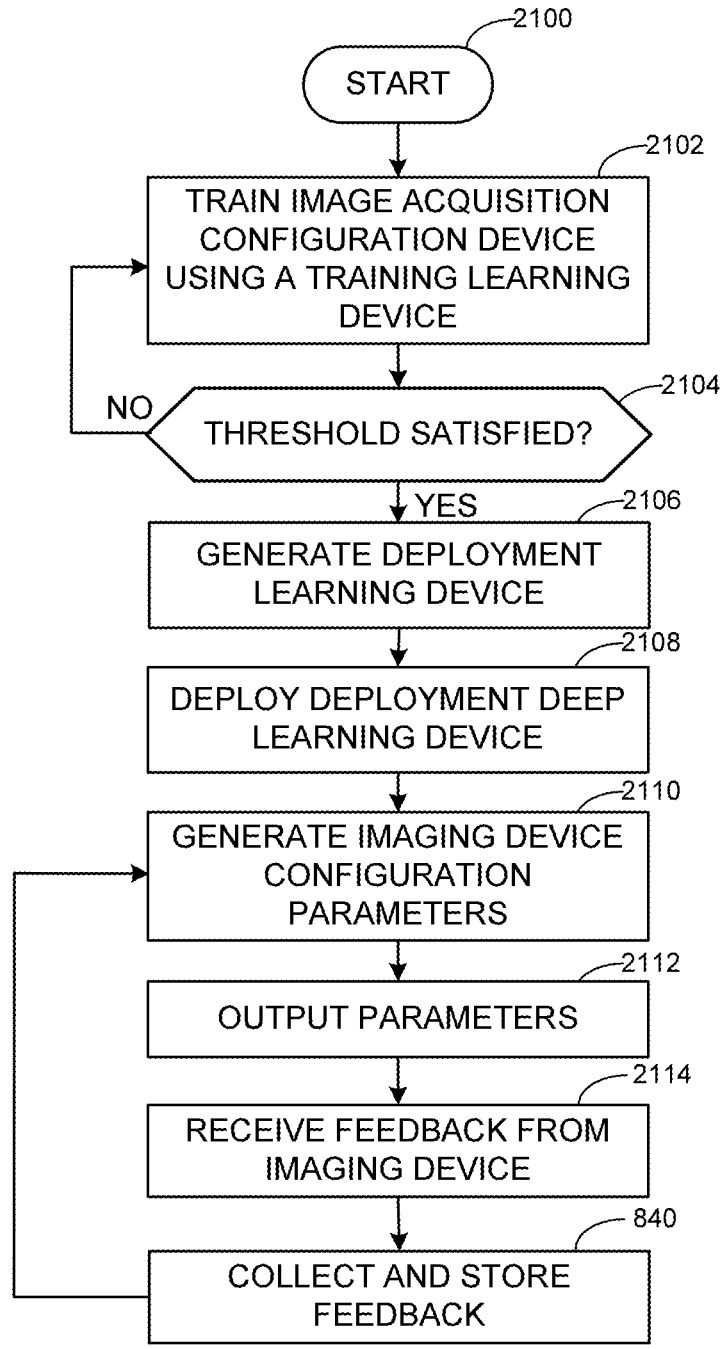
FIG. 21 illustrates a flow diagram of an example method to train and deploy the image acquisition configuration device of FIG. 20.

FIG. 21 illustrates a flow diagram of an example method 2100 to train and deploy the image acquisition configuration device 2020. At block 2102, the image acquisition configuration device 2020 is trained using the training device 2010. For example, the device 2020 and its initial configuration settings can be trained first using the training learning device 2010 based on training and testing one or more reference sets of parameters by the device 2010.

At block 2104, training continues until an output of the training learning device 2010 satisfies a threshold (e.g., compared to a known response from the reference data. Both good reference data and bad reference data can be used to train the device 2010 to recognize usable outcomes and unusable outcomes, for example. Until the training device 2010 reaches a reliability threshold associated with imaging device 1410 configuration parameters for a type of patient, type of examination, type of image acquisition, image quality threshold, etc., the training device 2010 continues to train and incorporates feedback on inefficiencies, inaccuracies, etc., to continue to learn and refine parameter selection for a given examination purpose, patient type, condition type, dosage, safety threshold, operating condition, etc.

Once the training device 2010 has been trained and validated as having sufficient reliability and quality, then, at block 2106, the deployed learning device 2050 is generated. For example, the trained network of the training device 2010 is used to generate a deployment network model for the deployed learning device 2050.

At block 2108, the image acquisition configuration device 2020 can be released for deployment at a customer site (e.g., for use by a technician associated with the imaging device 1 manufacturer, by the customer directly, etc.). The device 2020 can be deployed to physical connect or "plug in" to the imaging device 1410 (e.g., by wire, cable, connector, etc. Alternatively or in addition, the image acquisition configuration device 1120 can communicate wirelessly (e.g., via Bluetooth™, Bluetooth Low Energy (BLE™), near field communication (NFC), Wi-Fi™, etc.) with the imaging device 1410 to transmit settings to the imaging device 1410 and receive feedback from the imaging device 1410.

At block 2110, the image acquisition configuration device 2020 can generate configuration parameters for the imaging device 1410 to obtain one or more images of the patient 1406. Based on the patient 1406, prior patient information (e.g., patient medical history, family history from the information subsystem 1420, two-dimensional and/or three-dimensional scout scans, etc.), reason for and/or type of examination, etc., the deployed network 2050 of the configuration device 2020 generates configuration parameters to configure the imaging device 1410 for image acquisition of the patient 1406.

At block 2112, configuration parameters are output by the configuration device 2020. The configuration device 2020 can provide the parameters to the imaging device 1410 to automatically configure the imaging device 1410 for image acquisition (with operator override and/or adjustment, for example). The configuration device 2020 can also provide the parameters to the operator to be used to set up the imaging device 1410 for image acquisition.

At block 2114, feedback is received from the imaging device 1410 by the image acquisition configuration device 2020. For example, the feedback can be received via wired and/or wireless connection during and/or after image acquisition by the imaging device 1410. In certain examples, feedback regarding reconstruction and/or other processing of the acquired image data can also be provided to the acquisition configuration device 2020 and/or the training device 2010 to improve operation of the DDLD 2050 for parameter generation. For example, an indication of image quality (e.g., too low, sufficient, too high, etc.) can be processed by the training device 2010 to generate a new deep learning network to be deployed in the device 2050 to improve determination of imaging device 1410 settings by the configuration device 2020. At block 840, feedback is collected and stored for processing as described above. Feedback is used by the training device 2010 to continue to learn, modify, and improve setting recommendations, for example, during operation of the devices 1410, 2020. The feedback can be used to train further to respond to good quality and to make suggestions for bad quality image acquisition, for example.

Thus, the image acquisition configuration device 2020 serves as a black box that a customer and/or supplier can provide in conjunction with the imaging device 1410 to configure and improve operation of the imaging device 1410 with minimal user interaction. The customer can use and tweak the device 2020 but does not have to train and test the device 2020 before deploying the device 2020 with the imaging device 1410. An average user can obtain high quality (or sufficient diagnostic quality for reading, etc.) image acquisitions while avoiding a bad quality or unacceptable set of image acquisitions from the imaging device 1410 using the configuration device 2020 and its deployed learning device 2050.

In certain examples, a single button push can be facilitated for image acquisition, with the user 1404 pushing the button or otherwise selecting the option and the configuration device 2020 performing the remaining operations to configure and activate the imaging device 1410. For example, the device 2020 generates DICOM header information to be provided with patient information to the imaging device 1410 for image acquisition. The resulting image can be associated with the DICOM header including data such as patient history, blood pressure, etc. Information regarding prior images, prior diagnosis, information from other modality(-ies), etc., can be included.

The deployed learning device 2050 is trained to respond to good (or sufficient) quality images and provide suggestions to the user 1404 when a poor (or insufficient) quality image is obtained. The device 2050 recognizes good image quality and suggests settings used to obtain a good quality image in a particular circumstance as default settings for that particular circumstance. When a bad quality image is obtained (e.g., through bad settings, user error, etc.), the device 2050 can suggest how to recover from the mistake, such as by suggesting different settings that can be changed to correct the mistake. Input parameters include default field of view (DFOV), center, voltage (kV), current (mA), pitch, orientation, injection rate, injection timing, etc. Rather than acquiring a scout image to identify landmarks and use those settings, deep learning through the deployed device 2050 can facilitate a one-click determination of scan range, field of view, and/or other settings, and the operator can modify or approve and activate the image acquisition, for example.

For example, for a liver study, there are different ways to scan the patient. By providing symptoms, reasons for ordering the study, blood test results, etc., rather than pure operator selection, blood test, etc., the deployed learning device 2050 can determine how to scan the patient 1406, use or do not use contrast injection (e.g., how fast, concentration, total injection volume, etc.), use or do not use dual energy, etc. Settings can be evaluated and configured for a plurality of imaging modalities, such as CT, MICT, SPECT, PET, etc., which follow the same process with different inputs for different outputs. Cardiac imaging, neuro profusion, lung cancer screening, treatment response, etc., can be supported and improved using the configuration device 2020.

For example, if a patient 1406 is scheduled for a contrast-enhanced liver exam, a patient having normal heart size, size, and liver function uses certain contrast settings, but if the patient's cardiac function is low (e.g., compromised), a slower bolus (e.g., slower injection rate) and longer diluted contrast can be configured with the imaging device 1410 to help ensure that the contrast is provided in a particular place of the patient. Without more accurate configuration settings provided by the configuration device 2020, over nine hundred views of the patient may be obtained. By leveraging prior learning, however, only sixty views may be involved for a diagnosis, for example. In certain examples, working with the system health module 1550 and system design engine 1560, if the system is not operating with optimal performance, acquisition and/or reconstruction can be adjusted to obtain diagnostic image quality even though the imaging device 1410 is not operating normally. In certain examples, the training learning device 2010 can be perturbed (e.g., periodically and/or based on an event trigger such as a result, type of data, type of exam, etc.) to force the device 2010 to reevaluate its nodes, connections, weights, etc.

In certain examples, feedback to and/or from the device 2020 is captured in storage (e.g., stored and/or buffered cloud-based storage, etc.) including input data, actual output, and desired output. When a sufficient amount of feedback is received, the training learning network 2010 of the device 1120 is retrained in an incremental fashion or newly trained using the additional feedback data (e.g., based on original feedback data plus additional feedback data, etc.) depending on the amount of feedback data received. Thus, the training network 2010 can learn about user and/or site preferences for the imaging device 1410, etc., over time and react to those preferences for settings, alerts, recommended protocols, etc., by redeploying the deployed learning device 2050.

Image Reconstruction Examples

As described above, acquired image data can be reconstructed and/or otherwise processed for machine processing and/or human viewing. However, unless the image data is of sufficient quality for the intended machine processing and/or human reading, the image acquisition by the imaging device 1410 is not successful and beneficial to the patient 1406.

Image quality is an important parameter for medical imaging. Previously, traditional imaging measurement metrics, such as spatial resolution, temporal resolution, and low-contrast detectability, have been used extensively by the medical imaging community to compare the performance of different imaging devices, such as x-ray CT. Recently, there are significant efforts in redefining the image quality metrics that can be linked closer to the performance of the task-based results. These efforts, however, have met with limited success because of the numerous factors that impact the image quality such as complex anatomy, object-dependent spatial resolution, dose-dependent spatial resolution, image texture, application dependency, noise and pattern, human visual system, image artifacts, anatomy-dependent temporal resolution, object-dependent low contrast detectability (LCD), dose-dependent LCD, etc.

In certain examples, iterative reconstruction makes many measurement metrics nonlinear and less predictable. For example, a modulation transfer function (MTF) of iterative reconstructed images is both object-contrast-dependent as well as dose-dependent. Therefore, it is no longer sufficient to quote a single set of MTF numbers for an entire CT system, for example. One has to indicate the testing conditions under which the MTF has been obtained. This transforms a numerical value into a complex multi-dimensional variable.

This issue is further complicated by the human visual system. Judgment of the "quality" of an image can vary from one observer to another. For example, each radiologist has his or her preference in the appearance of the image based on past experiences. Some radiologists prefer coarser noise texture while other radiologists prefer finer texture. Often, radiologists link the presence of noise in the image with the "sharpness" of the structure in the image. Additionally, image texture cannot currently be mathematically defined. Many attempts, such as the introduction of noise-power-spectrum (NPS), fail to differentiate subtle differences in noise texture, for example.

Given the complexity of the problem, certain examples provide systems and methods to establish image quality metrics based on deep learning and/or other machine learning. For purposes of illustration only, the methodology is focused on x-ray CT imaging analysis and quality metrics. It should be understood, however, that such technology can be broadly applicable to other imaging modalities, such as MR, PET, SPECT, x-ray, ultrasound, etc.

Figure 22:
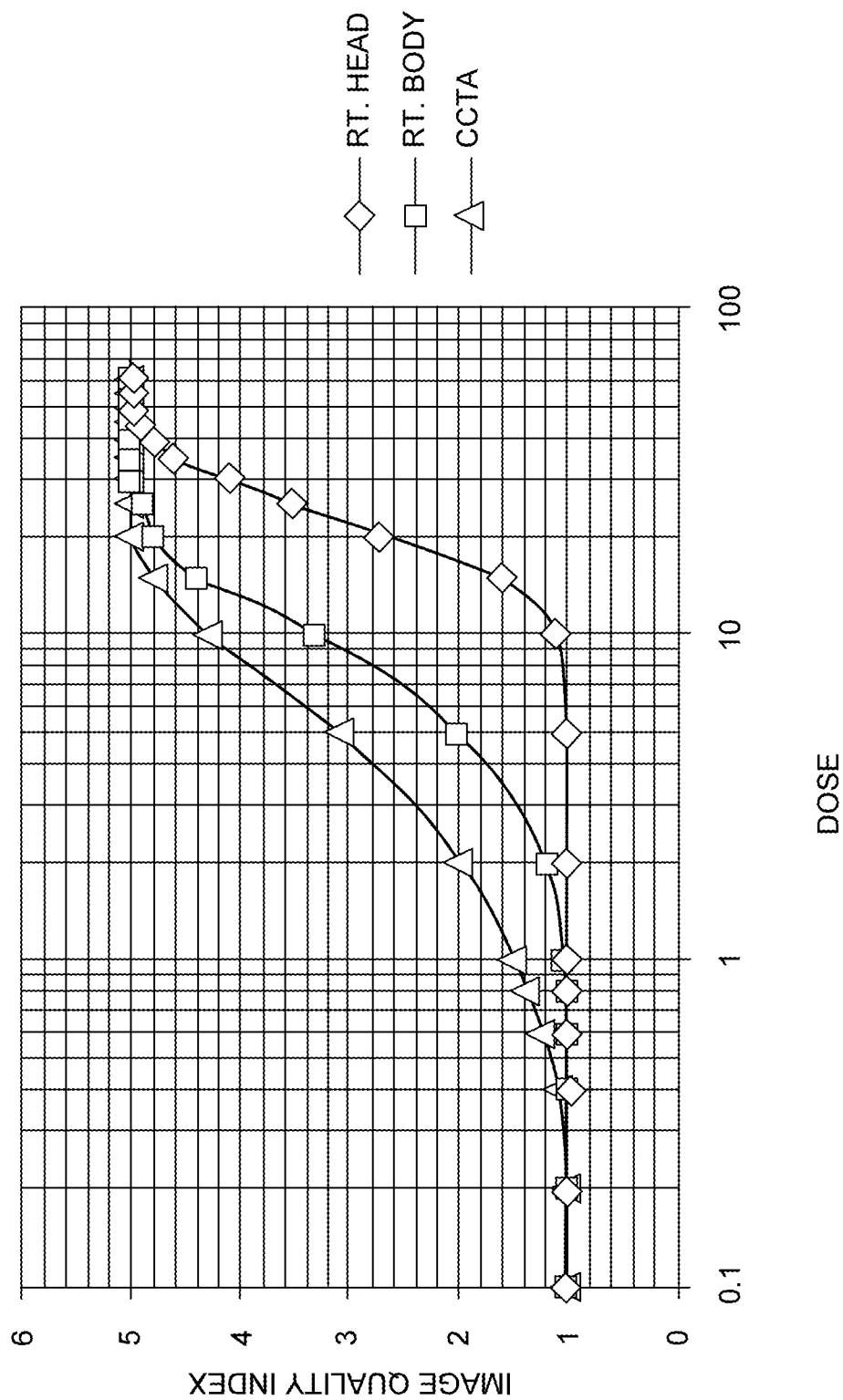
FIG. 22 shows a graph of an image quality index as a function of dose provided to a patient.

For x-ray CT, an image quality index (IQI) includes a plurality of factors, such as dose, and can be influenced by environmental factors such as the level of x-ray flux. In general, a higher x-ray dose produces better image quality. However, there is a detrimental effect on patient health since CT uses ionization radiation, and a high level of radiation exposure is linked to an increased probability of cancer. Therefore, it is desirable to establish IQI as a function of the dose provided to a patient, such as illustrated in the graph of FIG. 22. Note that IQI versus dose can be clinical application-dependent. For example, 40-50 Milligray (mGy) radiation is used to produce good non-contrast head images, while 8-10 mGy is used to generate good abdomen and pelvis images.

In certain examples, IQI is based on a 5-point scale for human consumption. In other examples, image quality is generated for computer analysis as a change in probabilistic values of image classification. On a scale of 1-5, for example, a 3 indicates the image is diagnosable (e.g., is of diagnostic quality), a 5 indicates a perfect image (e.g., probably at too high of a dose), and a 1 indicates the image data is not usable for diagnosis. As a result, a preferred score is 3-4. The DDLD 1532 can generate an IQI based on acquired image data by mimicking radiologist behavior and the 1-5 scale. Using image data attributes, the DDLD 1532 can analyze an image and determine features (e.g., a small lesion) and evaluate diagnostic quality of each feature in the image data. If the IQI is low (e.g., 1, 2, etc.), the DDLD 1532 can provide suggestions as to how to improve the image quality at the acquisition DDLD 1522. If the IQI is satisfactory (e.g., 3, 4, etc.), the image can be recommended for user 1404 (e.g., radiologist, etc.) reading. In certain examples, the learning and improvement factory 1530 can learn about a specific user and/or site image quality preferences over time. For example, Dr. S usually likes to see images with an IQI of 4. Learning this, the learning and improvement factory 1530 and/or the image quality assessment engine 1572 can propose a scan protocol to achieve an IQI of 4 or trigger a warning that the protocol will not achieve Dr. S's IQI preference. Thus, the reconstruction learning and improvement factory 1530 and/or the image quality assessment engine 1572 can facilitate a self-learning protocol based on the IQI determination (e.g., the factory 1530 learns that a user prefers protocol X to reach an IQI of Y, etc.).

In certain examples, the reconstruction DDLD 1532 can model an image as having varying probabilities of belong to a certain value or class. For example, an image can be categorize as belonging to class 4 with an associated probability of 90%, a 9% probability that the image belongs to class 5, and a 1% probability that the image belongs to class 3. The value of these percentages over time can be leveraged to statistically determine gradual changes at a more granular level.

While traditional methods of generating IQI have not been successful, at least because they fail to account for non-linear iterative reconstruction and the less-predictable nature of the human visual system, certain examples provide IQI generation that accounts for non-linear iterative reconstruction and human visualization. As described above, deep learning can be used to train and refine a target algorithm based on input data and desired output(s). Certain examples apply deep learning and/or other machine learning to image reconstruction and image quality metric, such as IQI, etc., determination.

Deep learning tries to mimic the human brain by recognizing objects using a layered approach. As the deep learning network is navigated from a lower layer to a higher layer, a higher-level set of features is extracted and abstracted. The extraction and abstraction provide an answer to the question and an identification of key "features" using to determine the answer. For example, image features used to determine the IQI include local signal to noise ratio, Markov random fields, scale and space based Gabor wavelet decomposition, Fourier transforms, etc. These features can be used to initialize the neural network and supplement automated feature maps to generate a classifier for image quality, for example. Images can be two-dimensional (2D), three-dimensional (3D), four-dimensional (4D), or n-dimensional (ND) images of a variety of modalities.

Deep learning input includes labeled images and/or unlabeled images, for example. The labeled images can be classified based on clinical applications, human anatomy, and/or other important attribute. The labeled images have also undergone image quality evaluation, and an IQI can be assigned to each labeled image. The labeled images are rated based on a confidence level for making clinical decisions using the image. For example, a level 3 indicates sufficient confidence to make a decision based on the image, while a level 5 indicates the highest level of confidence in making the decision based on the image. A level 1, on the other hand, indicates that such image cannot be used for diagnosis. The labeled images are used to train the deep learning image quality algorithm initially.

FIGS. 23A-23B illustrate example learning and testing/evaluation phases for an image quality deep learning network. As shown in the example of FIG. 23A, known, labeled images 2310 are applied to a convolution network 2320. The images 2310 are obtained using multiple users, and their image quality indices are known. As discussed above with respect to FIGS. 1-3, the convolution 2320 is applied to the input images 2310 to generate a feature map, and pooling 2330 reduces image size to isolate portions 2325 of the images 2310 including features of interest to form a fully connected layer 2340. A classifier 2350 (e.g., a softmax classifier, etc.) associates weights with nodes representing features of interest. The classifier 2350 provides weighted features that can be used to generate a known image quality index 2360. In certain examples, a central tendency metric such as average image quality indices can be used as the known image quality index 2360 for training purposes. The evaluation can be performed separately on individual images, for example.

In the example of FIG. 23A, a number of feature maps are created by convolving the input 2310 by a number of convolutional kernels 2320. Each convolutional kernel 2320 is randomly initialized and, as the learning progresses, the random kernels converge to "feature maps." This is followed by the pooling layer 2330. Fully connected layers 2340 are formed by pooling 2330 and additional convolution and pooling layers may be optionally added. A classifier stage

2350 is the final layer to determine the output index 2360. In certain examples, training of the network 2300 is done in batches using a stochastic gradient method (SGD).

Unlabeled images are images that have not yet been evaluated to identify and label features in the image. Unlabeled images can be used to test the performance of the deep learning algorithm trained in FIG. 23A and refine the algorithm performance. As illustrated in the example of FIG. 23B, the example network 2300 can also be applied to unlabeled images 2315. An image quality index 2365 can be generated and can be compared to the known image quality index 2360 to evaluate the development and reliability of the network 2300. If the network 2300 is tested and found to be a satisfactory determiner of image quality, the network 2300 can be deployed as the reconstruction DDLD 1532, for example.

There are several deep learning and other machine learning techniques that can be useful for classifying images to be associated with certain IQI. For example Deep Convolutional Networks can be set up in several ways depending upon the availability of labeled data, computational and memory constraints, performance requirements, etc. In a convolutional layer of an example deep convolutional network, an initial layer includes a plurality of feature maps in which node weights are initialized using parameterized normal random variables. The feature maps are followed by a first pooling layer, which is followed by a second convolution layer, which is then followed by a second pooling layer, and so on. Subsequent pooling and convolution layers are optional depending upon configuration, complexity, type of data, target environment, etc. A final layer is a classification layer using, for example, a softmax classifier, to evaluate options in the network.

Figure 24A:
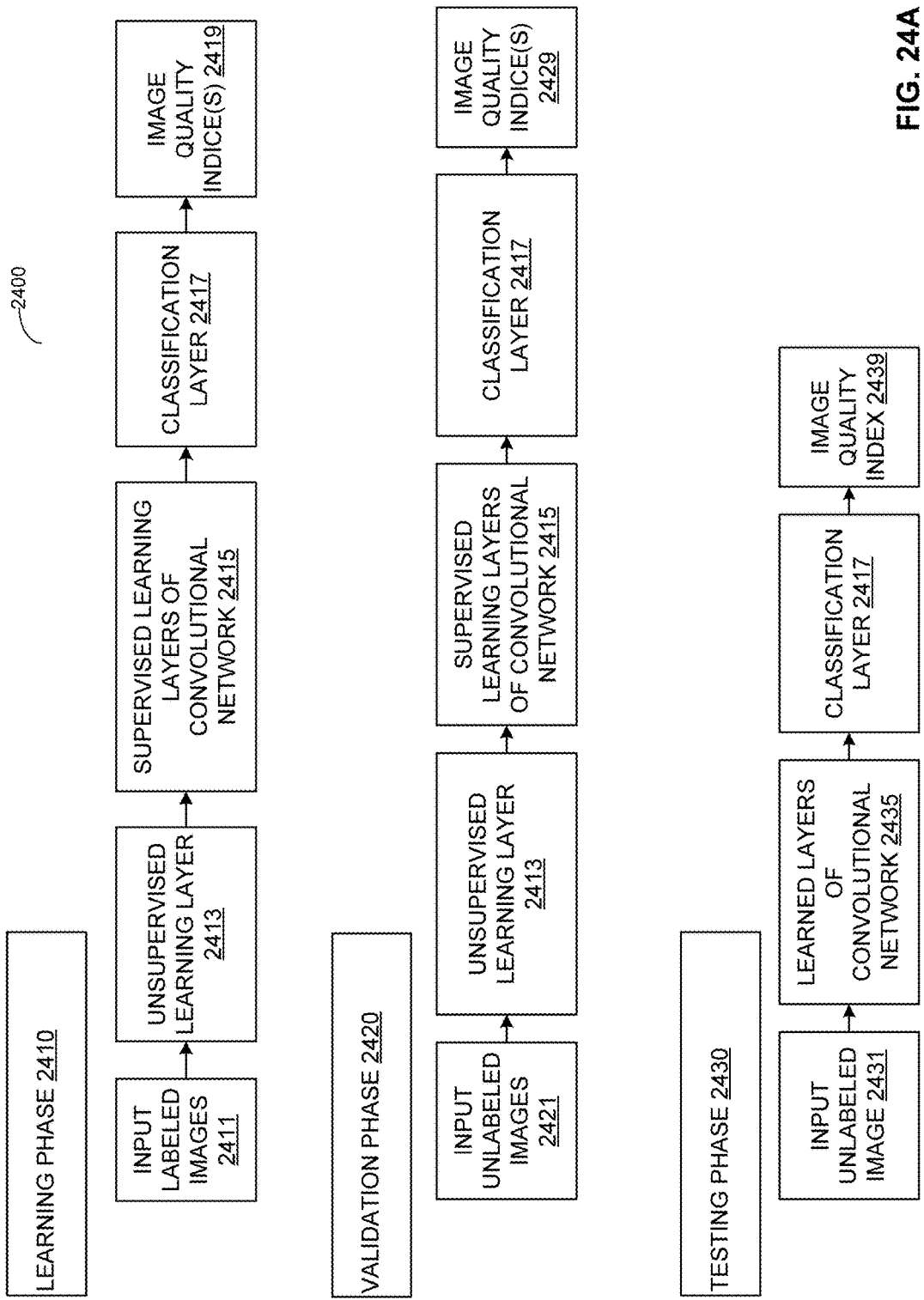
FIGS. 24A-24B show example learning, validation, and testing phases for an example deep convolution network.
Figure 24B:
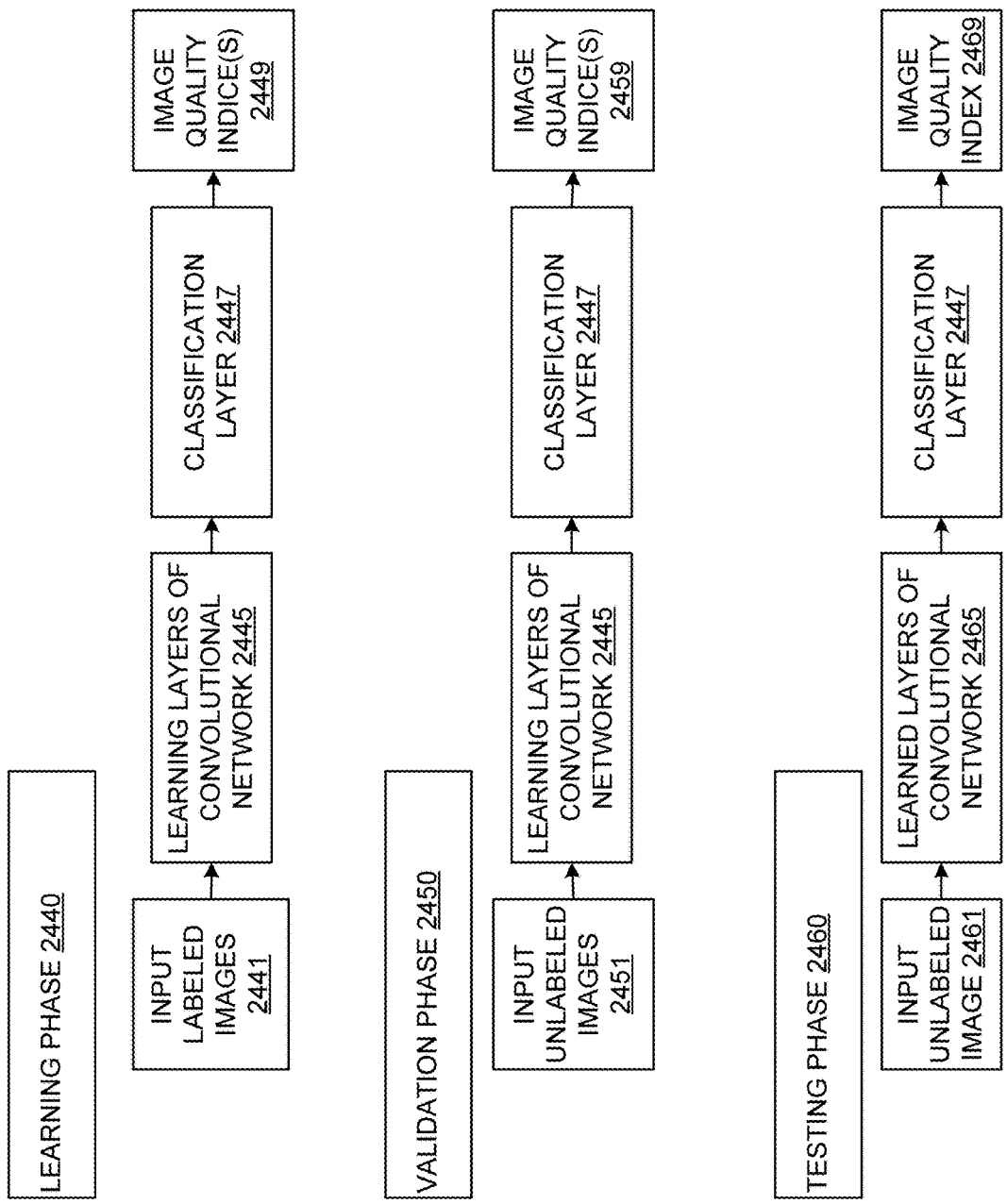

In certain examples, weights and biases for the classification layer are set to 0. An output from the softmax layer is a set of positive numbers which sum up to 1. In other words, the output from the softmax layer can be thought of as a probability distribution. Using this distribution, the network can be used to select values for desired hyper parameters. FIGS. 24A-24B show example learning, validation, and testing phases for an example deep convolution network.

As shown in the example of FIG. 24A, if a large set of labeled data is not available in a collection of medical data, an example network 2400 can be trained, validated and tested. In a learning phase 2410, labeled images are input 2411 to an unsupervised learning layer 2413 (e.g., an auto encoder, etc.). The unsupervised learning layer 2413 initializes a feature space for the input 2411. After processing by the unsupervised learning layer 2413, the image information then passes to one or more supervised learning layers of a convolutional network 2415. As described above, feature maps can be created and features can be reduced via the convolutional layers 2415. The supervised learning layers 2415 are hidden layers in the network 2400 and perform backpropagation. Output is then classified via a classification layer 2417, which analyzes weights and biases and generates one or more image quality indices 2419.

In a validation phase 2420, hyper parameters are tuned by inputting unlabeled images 2421 to the unsupervised learning layer 2413 and then to the supervised learning layers of the convolutional network 2415. After classification 2417, one or more image quality indices 2419 are generated.

After tuning parameters during the validation phase 2420, a testing phase 2430 processes an input unlabeled image 2431 using learned layers of the convolution network 2435. The classification layer 2417 produces an image quality index 2439.

If a large set of labeled data is available, a network can be trained, validated, and tested as shown in the example of FIG. 24B. In a learning phase 2440, labeled images are input 2441 to one or more learning layers of a convolutional network 2445. As described above, feature maps can be created and features can be reduced via the convolutional layers 2445. Output is then classified via a classification layer 2447, which analyzes weights and biases and generates one or more image quality indices 2449.

In a validation phase 2450, hyper parameters are tuned by inputting unlabeled images 2451 to the learning layers of the convolutional network 2445. After classification 2447, one or more image quality indices 2459 are generated.

After tuning parameters during the validation phase 2450, a testing phase 2460 processes an input unlabeled image 2461 using learned layers of the convolution network 2465. The classification layer 2447 produces an image quality index 2469.

While the examples of FIGS. 24A-24B have been illustrated with auto encoder and deep convolutional networks, deep residual networks can be used in the examples as well. In a deep residual network, a desired underlying mapping is explicitly defined in relation to stacked, non-linear internal layers of the network. Using feedforward neural networks, deep residual networks can include shortcut connections that skip over one or more internal layers to connect nodes. A deep residual network can be trained end-to-end by stochastic gradient descent (SGD) with backpropagation, such as described above.

Additionally, deep learning networks can be improved through ongoing learning and evaluation in operation. In certain examples, an analysis of intermediate layers of the neural network combined with preprocessing of the input data can be used to determine redundancies in the data to drive data generation efficiencies. Preprocessing of data can include, but is not limited to, principal component analysis, wavelet decomposition, Fourier decomposition, matched filter decomposition, etc. Each preprocessing can generate a different analysis, and preprocessing techniques can be combined based on the structure of the deep learning network under one or more known conditions. A meta-analysis can then be performed across a plurality of individual analyses (e.g., from each preprocessing function performed).

In certain examples, feedback from the deep learning system can be used to optimize or improve input parameter selection, thereby altering the deep learning network used to process input (e.g., image data, device parameter, etc.) to generate output (e.g., image quality, device setting, etc.). Rather than scanning over an entire set of input parameters to create raw data, a variation of active learning can be used to select a starting parameter space that provides best results and then randomly decrease parameter values to generate raw inputs that decrease image quality but still maintain an acceptable range of quality values. Randomly decreasing values can reduce runtime by processing inputs that have little effect on image quality, such as by eliminating redundant nodes, redundant connections, etc., in the network.

Figure 25A:
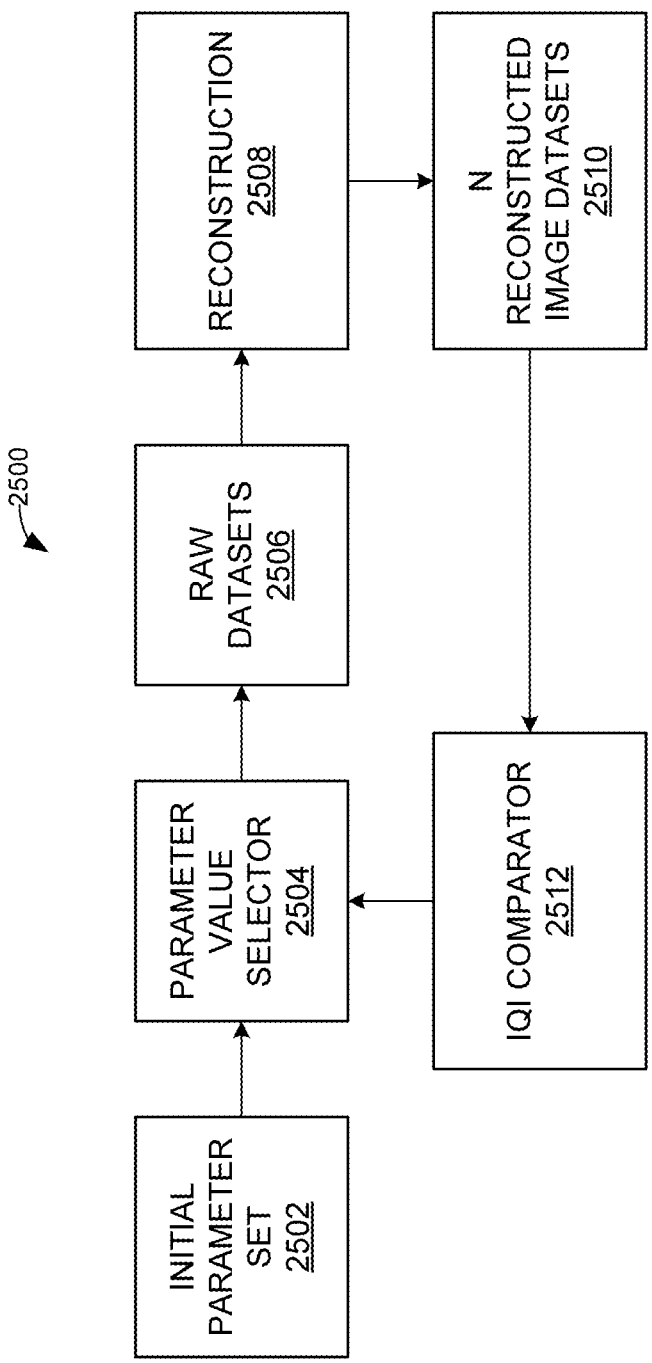
FIG. 25A shows an example trained network leveraged to determine an output quality for an initial set of reconstruction parameters.

For example, to use multiple input parameters to process each raw dataset to produce a corresponding output dataset while reducing parameter set values that still maintain the processed output dataset, a search strategy is employed to navigate through the parameter space. First, parameters used in data processing (e.g., reconstruction parameters, etc.) are determined. As shown in the example of FIG. 25A, a trained network 2500 is leveraged to determine an output quality (e.g., IQI of reconstructed image datasets) for a starting or initial parameter set 2510 of reconstruction parameters and is used as a baseline. For example, the starting parameter set 2510 includes reconstruction parameters Param 0, Param 1, . . . , Param N. Starting with known values (including redundant parameters), a reference IQI can be determined for N datasets.

Since the goal is to reduce the number of parameters, parameter values are decreased according to a given strategy (e.g., gradient decent, etc.) until a stop criteria is met (e.g., eliminate known trivial selections providing bad results, etc.). A parameter value selector 2504 determines the search strategy limiting the search space and updating results. Raw datasets 2506 (e.g., Dataset 0, Dataset 1, . . . , Dataset N) are processed for reconstruction 2508 to produce N reconstructed image datasets 2510. An IQI comparator 2512 processes each image dataset 2510 to generate a feedback value to the parameter value selector 2504. The feedback value is based on a disparity between an average parameter-based IQI is to a current average parameter-based IQI. This process is repeated for different datasets to map the general behavior of the parameter pruning process for each parameter in a normalized space. The process is repeated until the set providing the minimal parameter values is identified which still provides acceptable image quality which can be used as a best available solution.

Figure 25B:
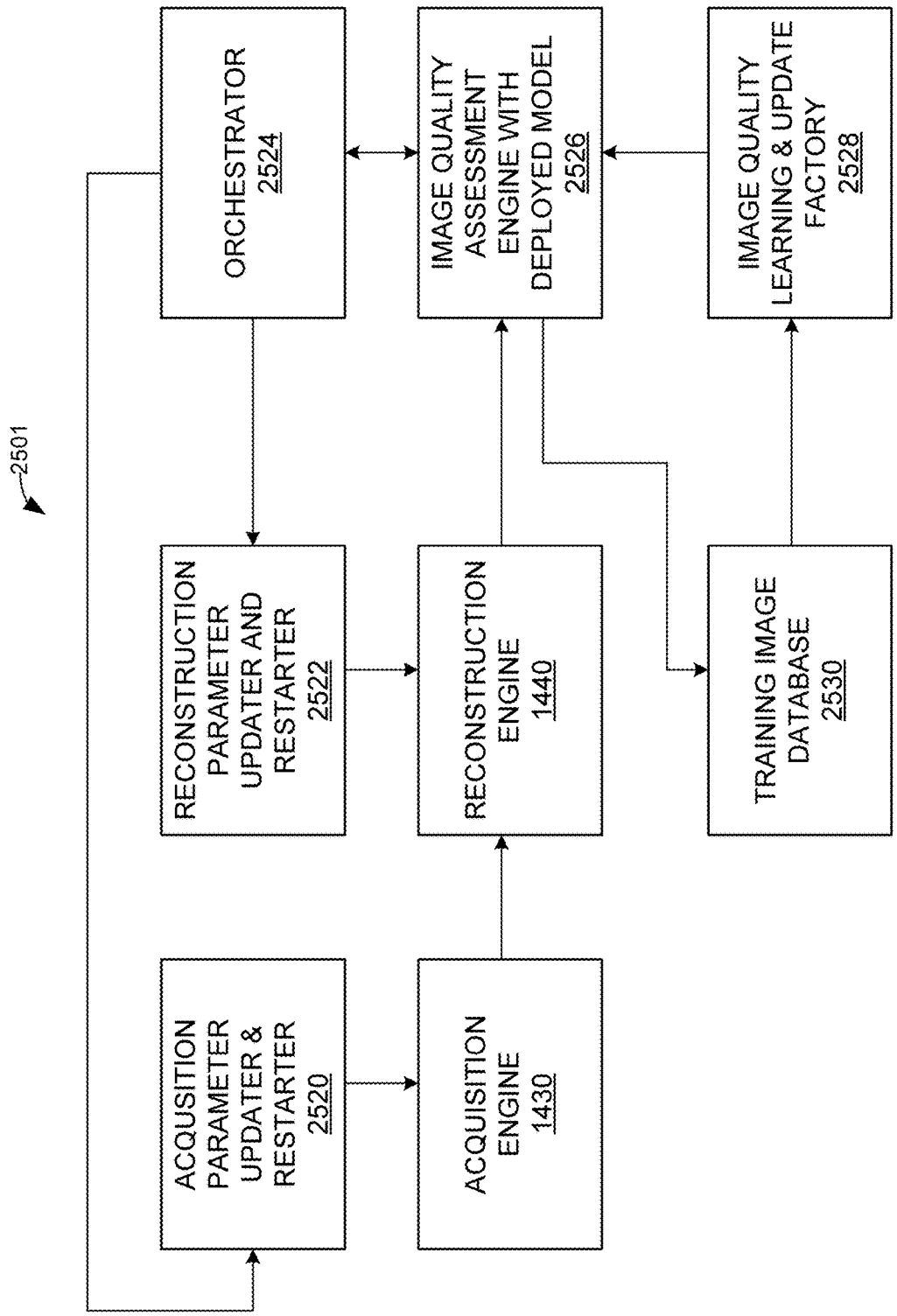
FIG. 25B illustrates an example system for image quality assessment and feedback using a deployed network model.

FIG. 25B illustrates an example system 2501 for image quality assessment and feedback using a deployed network model. As shown in the example of FIG. 25B, an acquisition parameter updater and restarter 2520 provides an update to the acquisition engine 1430. A reconstruction parameter updater and restarter 2522 provides an update to the reconstruction engine 1440. An orchestrator 2524 coordinates among the engines 2520, 2522, and an image quality assessment engine with deployed model 2526. An image quality learning and update factory 2528 learns from a training image database 2530 to train a deep learning network model to be deployed with the image quality assessment engine 2526 (e.g., the image quality assessment engine 1572, etc.). In operation, the image quality assessment engine with deployed model 2526 provides information to the training image dataset 2530 which can be used in ongoing monitoring and improvement of the factory 2528, for example. The training image dataset 2530 can include image data representing different classes of example error conditions, for example. Using the orchestrator 2524, the acquisition engine 1430 and/or the reconstruction engine 1440 can be updated and restarted by the acquisition parameter updater and restarter 2520 and/or the reconstruction parameters updater and restarter 2522, respectively, for example.

Figure 25C:
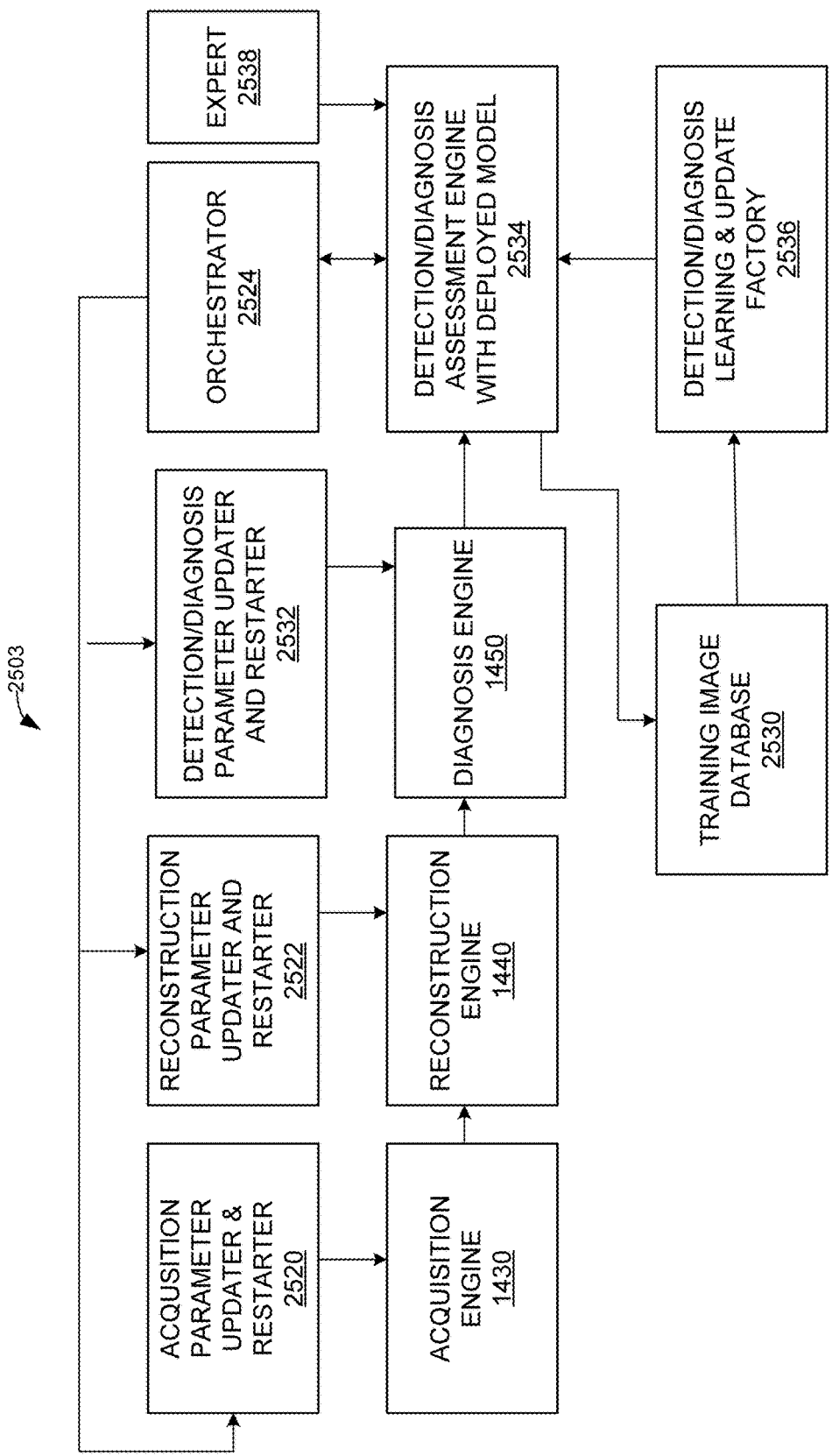
FIG. 25C illustrates an example system for detection and/or diagnosis assessment and feedback using a deployed network model.

FIG. 25C illustrates an example system configuration 2503 that further includes a detection/diagnosis parameter updater and restarter 2532 associated with the diagnostic engine 1450. The example system 2503 also includes a detection/diagnosis assessment engine with deployed model 2534. The diagnosis assessment engine with deployed model 2534 is generated from a detection/diagnosis learning and update factory 2536 leveraging data from the training image database 2530. The training image database 2530 includes data representing different classes of example detection and diagnosis of conditions, for example.

In the example of FIG. 25C, the orchestrator 2524 coordinates among the engines 2520, 2522, 2532, and the detection/diagnosis assessment engine with deployed model 2534. The detection/diagnosis learning and update factory 2535 learns from the training image database 2530 to train a deep learning network model to be deployed with the detection/diagnosis assessment engine 2534 (e.g., the diagnosis assessment engine 1574, etc.). In operation, the detection/diagnosis assessment engine with deployed model 2534 provides information to the training image dataset 2530 which can be used in ongoing monitoring and improvement of the factory 2534, for example. The engine 2534 can operate in conjunction with an expert 2538, for example. Using the orchestrator 2524, the acquisition engine 1430, the reconstruction engine 1440, and/or the diagnosis engine 1450 can be updated and restarted by the acquisition parameter updater and restarter 2520, the reconstruction parameters updater and restarter 2522, and/or the detection/diagnosis parameter updater and restarter 2532, respectively, for example.

Certain examples utilize deep learning and/or other machine learning techniques to compute task-based image quality from acquired image data of a target. Since humans can visually appreciate a level of image quality (e.g., noise, resolution, general diagnostic quality, etc.) by viewing the images, an artificial intelligence or learning method (e.g., using an artificial neural network, etc.) can be trained to assess image quality. Image quality (IQ) has usually been estimated based on phantom scans using wires, line pairs, and uniform regions (e.g., formed from air, water, other material, etc.). This requires a separate scan of the physical phantom by a human operator and reading by a technician and/or radiologist, and it is often not practical to perform multiple phantom scans to measure image quality. Moreover, image quality itself may depend on the object or patient being scanned. Hence, the image quality with a test phantom may not be representative of quality obtained when scanning an actual patient. Finally, traditional IQ metrics such as full-width at half maximum (FWHM) of the point spread function (PSF), modulation transfer function (MTF) cutoff frequency, maximum visible frequency in line pairs, standard deviation of noise, etc., are not reflecting true task-based image quality. Instead, certain examples provide it is impactful to estimate IQ directly from acquired clinical images. Certain examples assess image quality using a feature-based machine learning or deep learning approach, referred to as a learning model. In certain examples, task-based image quality (and/or overall image quality index) can be computed directly from actual patient images and/or object images.

Using images (e.g., clinical images) with a known image quality (IQ) of interest, a learning model can be trained. Additional training images can be generated by manipulating the original images (e.g. by blurring or noise insertion, etc., to obtain training images with different image quality). Once the learning model is trained, the model can be applied to new clinical images to estimate an image IQ of interest.

For example, image input features such as mean, standard deviation, kurtosis, skewness, energy, moment, contrast, entropy, etc., taken from cropped raw image data and edge map information are combined with one or more label such as spatial resolution level, spatial resolution value, etc., to form a training set for a machine learning system. The machine learning network forms a training model using the training set and applies the model to features obtained from a test set of image data. As a result, the machine learning network outputs an estimated spatial resolution (e.g., level and/or value) based on the training model information.

In certain examples, a regression and/or classification method can be used to generate image quality metrics by labeling the training data with an absolute value and/or level of the corresponding image IQ metric. That is, metrics can include quantitative measures of image quality (e.g., noise level, detectability, etc.), descriptive measures of image quality (e.g., Likert score, etc.), a classification of image quality (e.g., whether the image is diagnostic or not, has artifacts or not, etc.), and/or an overall index of image quality (e.g., an IQI).

In a feature-based machine learning approach, an input to model training includes extracted features from the training image data set. Feature selection can be tailored to an image IQ of interest. Features include, but are not limited to, features based on a histogram of intensity values (e.g., mean, standard deviation, skewness, kurtosis, energy, energy, contrast, moment, entropy, etc.). These features can be calculated from raw image data and/or can be extracted after applying a difference filter on the image for local enhancement and/or other image operation and/or transformation. These features can be calculated from an entire image, a cropped image, and/or from one or more regions of interest (ROIs). Global and/or local texture features based on an adjacency matrix (such as Mahotas Haralick, etc.) can also be included.

In a deep learning (e.g., convolutional neural network)-based approach, a set of features need not be defined. The DLN will identify features itself based on its analysis of the training data set. In certain examples, more data is involved for training (if features have not been identified) than with a feature-based machine learning approach in which features have been identified as part of the input.

Thus, in certain examples, input can include a full image, a cropped image (e.g., cropped to a region of interest), an image patch, etc. With an image patch, smaller image patches can be used to assess image quality on a local basis, and a map of image quality can be generated for the image. Metrics such as quantitative image IQ, such as spatial resolution, noise level, and/or task-based IQ metric (e.g., detectability, etc.) can be extracted directly from clinical images. Certain examples can be applied in any context in which image quality assessment is performed or desired, such as to compare imaging technologies (e.g., hardware and/or algorithms); during image acquisition to improve or optimize a scanning technique and reconstruction in real time (or substantially real time given a processing, storage, and/or data transmission latency) while reducing or minimizing radiation dose, and/or to provide quantified image IQ to clinicians to help with diagnosis, etc. The proposed techniques can be applied to other imaging modalities between the example of CT, such as MRI, PET, SPECT, X-ray, tomosynthesis, ultrasound, etc.

Thus, by identifying sources of variation (e.g., in image resolution, etc.) and reconstructing images in view of the variation, a standardization transform can be created by a machine learning network, refined, and applied to image reconstruction (e.g., using the reconstruction engine 1430 and associated DDLD 1532. When image attributes are computed, a recalibration transform can be developed, refined, and applied to compute image attributes. Analytics can be provided to clinicians and used to evaluate image resolution using the learning network.

For example, suppose a data set includes nine cardiac volumes with 224 images per volume. A Gaussian blur is applied to the images to generate images at four additional resolution levels. The total sample size is then 224*5*9=10080. Seven features are extracted from the raw image data, and eight features are extracted from an edge map of the image. Cross-validation is facilitated by splitting the sample into a training set (70%) and a test set (30%), and a random forest regression was used.

Figure 26:
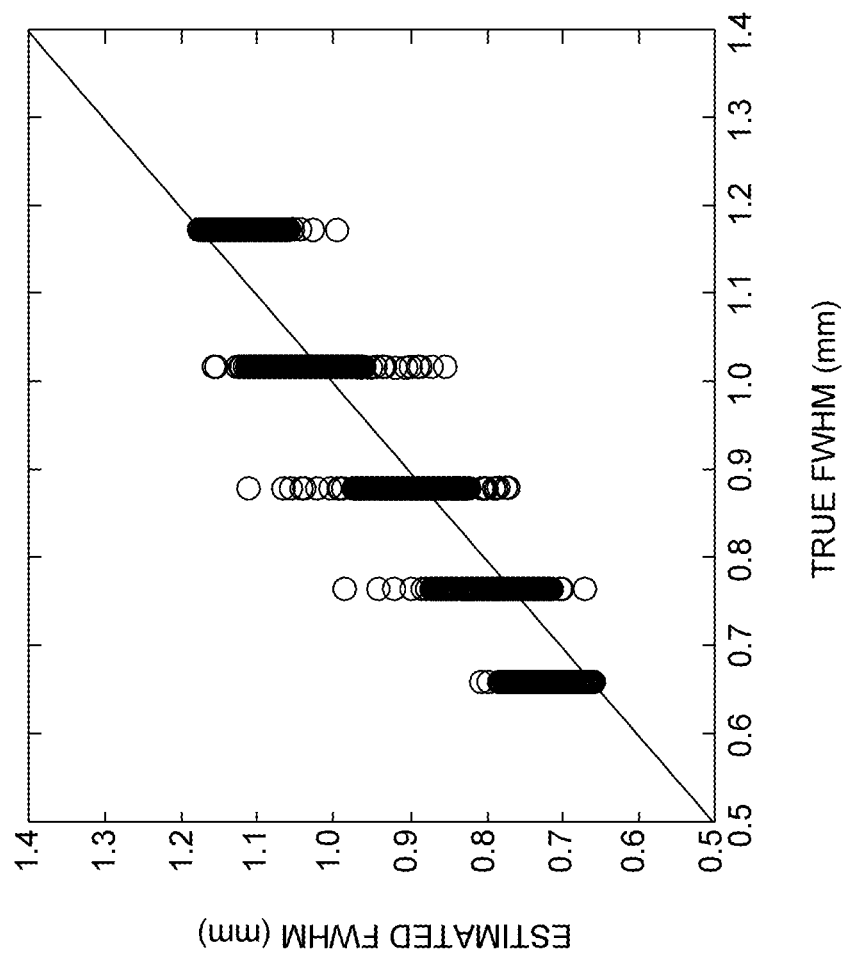
FIGS. 26-30 depict graphs of experimental results using techniques disclosed herein.
Figure 27:
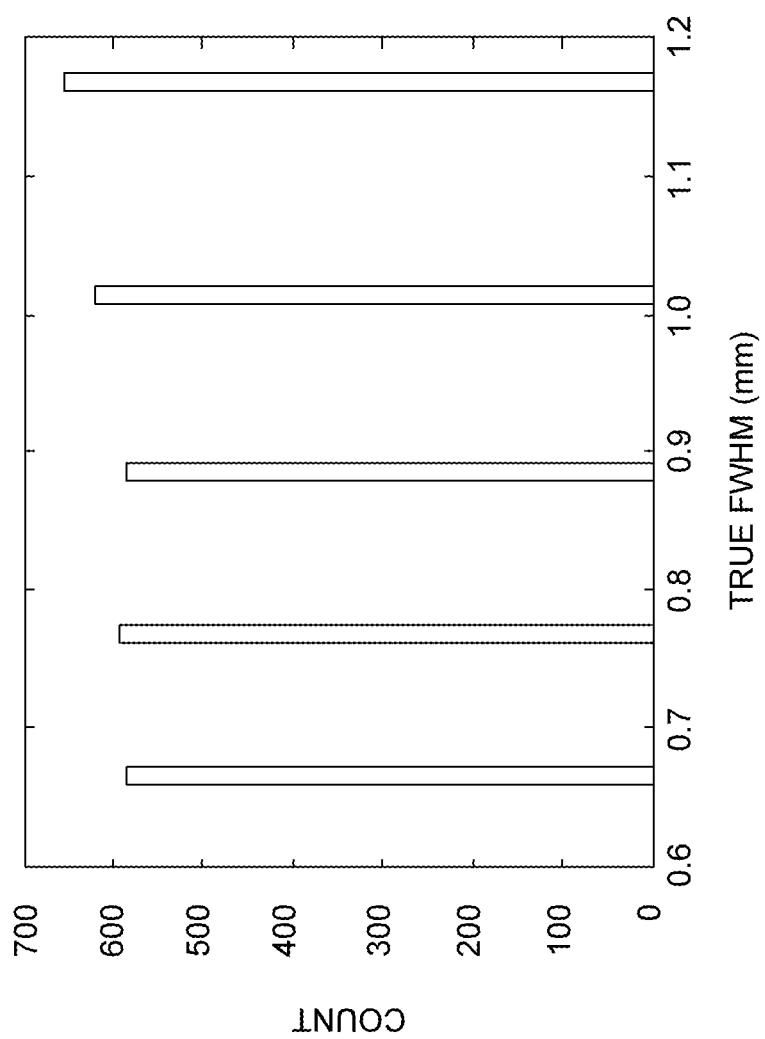
Figure 28:
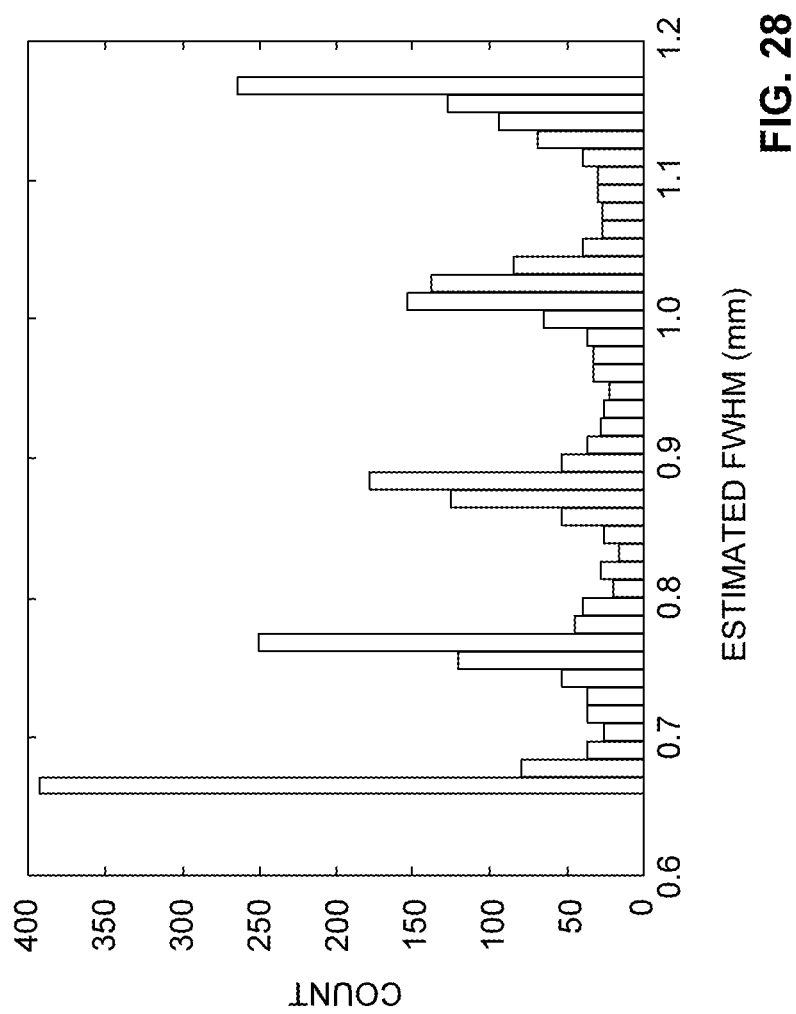
Figure 29:
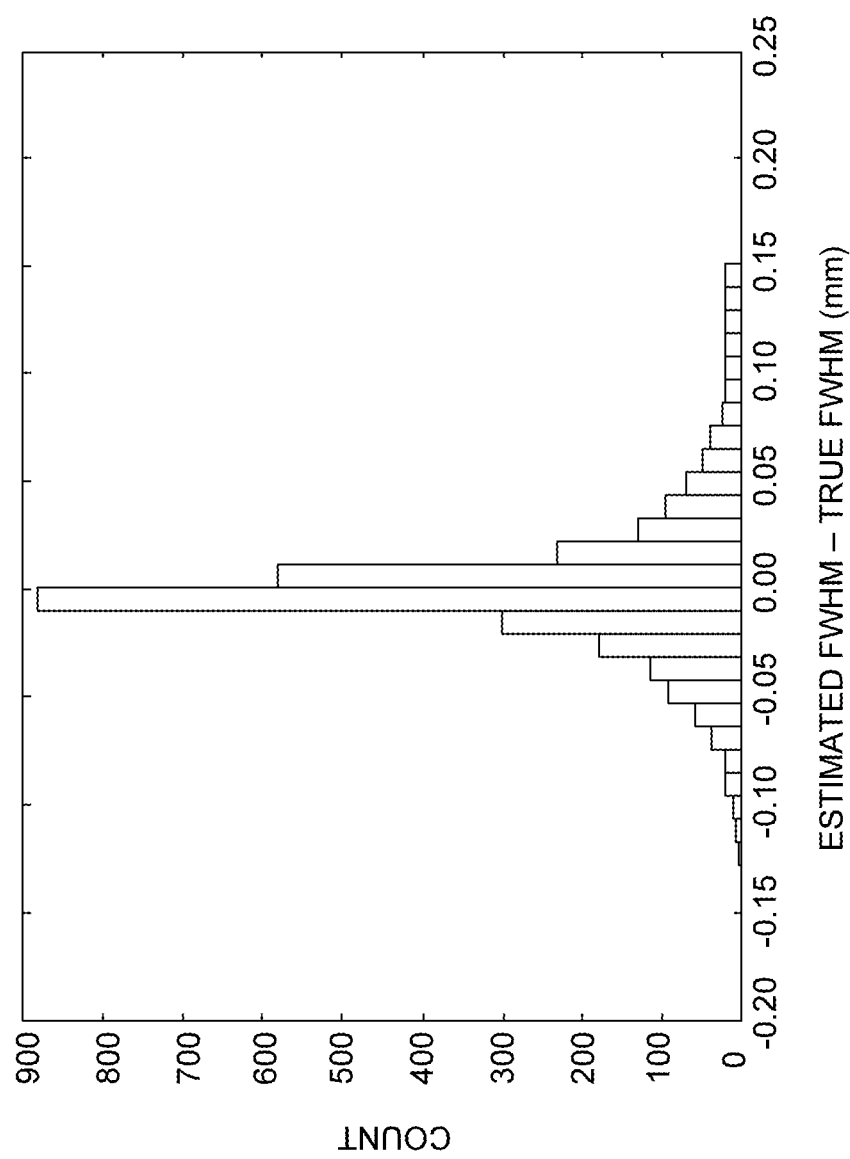
Figure 30:
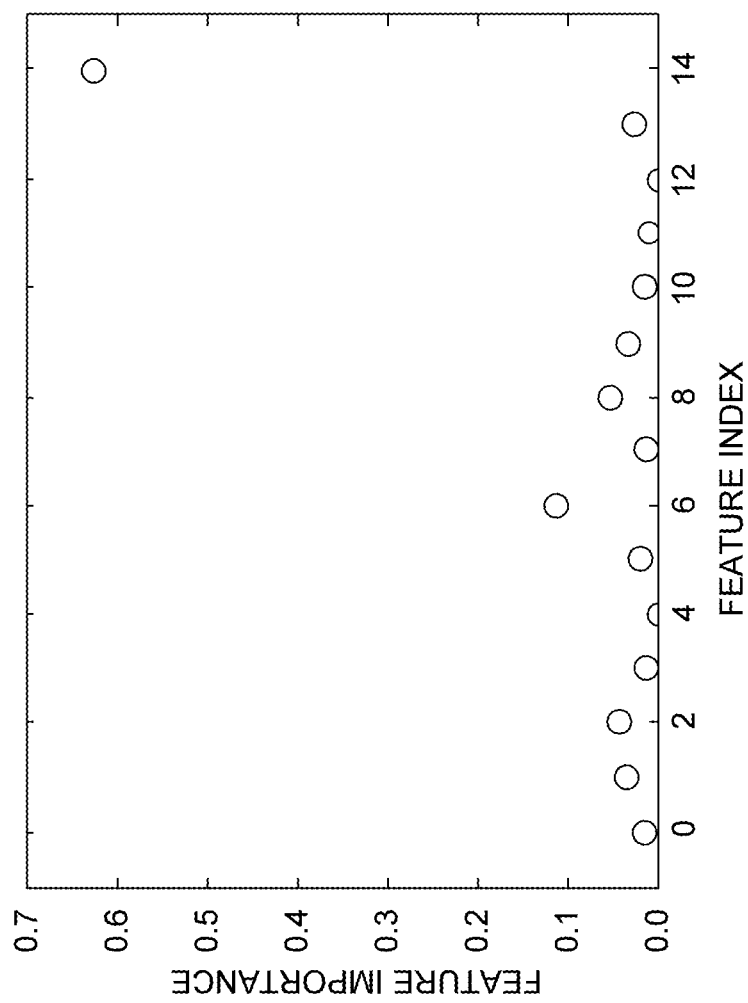

Results were generated and contrasted between estimated (using machine learning) and actual (measured) error or distribution. For example, FIG. 26 illustrates a comparison of estimated FWHM (in millimeters) to true FWHM. FIG. 27 shows an example true FWHM distribution. FIG. 28 shows an example estimated FWHM distribution. FIG. 29 shows an example estimation error in the FWHM of the PSF (e.g., estimated FWHM−true FWHM (mm)). FIG. 30 shows an example comparison of feature importance from the example data set. The example graph of FIG. 30 organizes feature importance by feature index. Features from raw image data include: 0: Mean, 1: Kurtosis, 2: Skewness, 3: Energy, 4: Moment, 5: Contrast, 6: Entropy. Features from the edge map include: 7: Mean, 8: Standard Deviation, 9: Kurtosis, 10: Skewness, 11: Energy, 12: Moment, 13: Contrast, 14: Entropy. As shown from the example data, machine learning yields reasonable results for estimating spatial resolution from clinical datasets. Additionally, entropy of the edge map is shown to be an important feature to estimate spatial resolution, as well as entropy of the raw image.

Additional use cases can include lung nodule/calcification or small structure detection and analysis for lung cancer detection. Source of variation can include noise (e.g., mA, peak kilovoltage (kVp), patient size, etc.), resolution (e.g., reconstruction kernel type, thickness, pixel size, etc.), respiratory and cardiac motion (e.g., rotation speed and patient compliance, etc.), blooming artifact (e.g., reconstruction method, partial volume, motion, etc.). An impact on outcome can include measurement error in volume and density which lead to under-staging and missed structure. Another use case can include a cardiac perfusion analysis to diagnose coronary artery disease (CAD). Source of variation can include patient physiology (e.g., cross patients and same patient, dynamic range small, etc.), beam hardening artifact (patient uptake, bolus timing, etc.), cardiac motion, contrast pooling, etc. Impact on outcome can include an incorrect perfusion map (e.g., missed perfusion defect or wrong diagnosis of perfusion defect, etc.). Another use case can include liver lesion/small dark structures for cancer detection. Source of variation can include noise (e.g., mA, kVp, patient size, etc.), resolution (e.g., reconstruction kernel type, thickness, pixel size, etc.), structured noise (e.g., streaks, pattern, texture, etc.), shadowing artifact (e.g., bone, ribs, spines reconstruction artifact, etc.), motion, etc. An impact on outcome can include a missed lesion or incorrect diagnosis due to low contrast detectability.

Another use case can include coronary/vascular imaging. Source of variation can include streak or blooming artifact (e.g., reconstruction method, partial volume, motion, etc.), noise (e.g., mA, kVp, patient size, etc.), resolution, etc. Impact on outcome can include, if analysis of lumen is needed, noise and resolution have a bigger impact.

Another use case can include brain perfusion for stroke. Source of variation can include shadowing artifact from bone, small physiological change (e.g., dynamic range small, etc.), structured noise (e.g., reconstruction method, etc.), etc. Impact on outcome can include an incorrect perfusion map (e.g., missed perfusion defect or wrong diagnosis of perfusion defect, etc.), etc.

Another use case can include Chronic Obstructive Pulmonary Disease (COPD) and/or other lung disease (e.g., pneumoconiosis, etc.) diagnosis and classification (e.g., Thoracic VCAR), etc. Source of variation can include noise (e.g., mA, kVp, patient size, slice thickness, etc.), resolution (e.g., kernel, pixel size, thickness size, etc.), contrast (e.g., iodine, etc.), patient physiology (e.g., lung volume during scan, can be measured from image, etc.), respiratory motion, etc. Impact on outcome can include measurement error (e.g., airway diameter/perimeter, luminal narrowing underestimated, wall thickening overestimated, etc.), etc.

Another use case can include liver fat quantification (e.g., steatosis grading, cirrhosis staging, etc.). Source of variation can include noise (e.g., mA, kVp, patient size, etc.), resolution (e.g., reconstruction kernel type, thickness, pixel size, etc.), structured noise (e.g., streaks, pattern, texture, etc.), shadowing artifacts (e.g., ribs, spines reconstruction artifact, etc.), etc. An impact on outcome can include measurement error and mis-staging, etc. Another use case can include volume/size quantification of other organs (e.g., kidney transplant, etc.) or masses in organ (e.g., cyst or stones, etc.), etc.

Figure 31A:
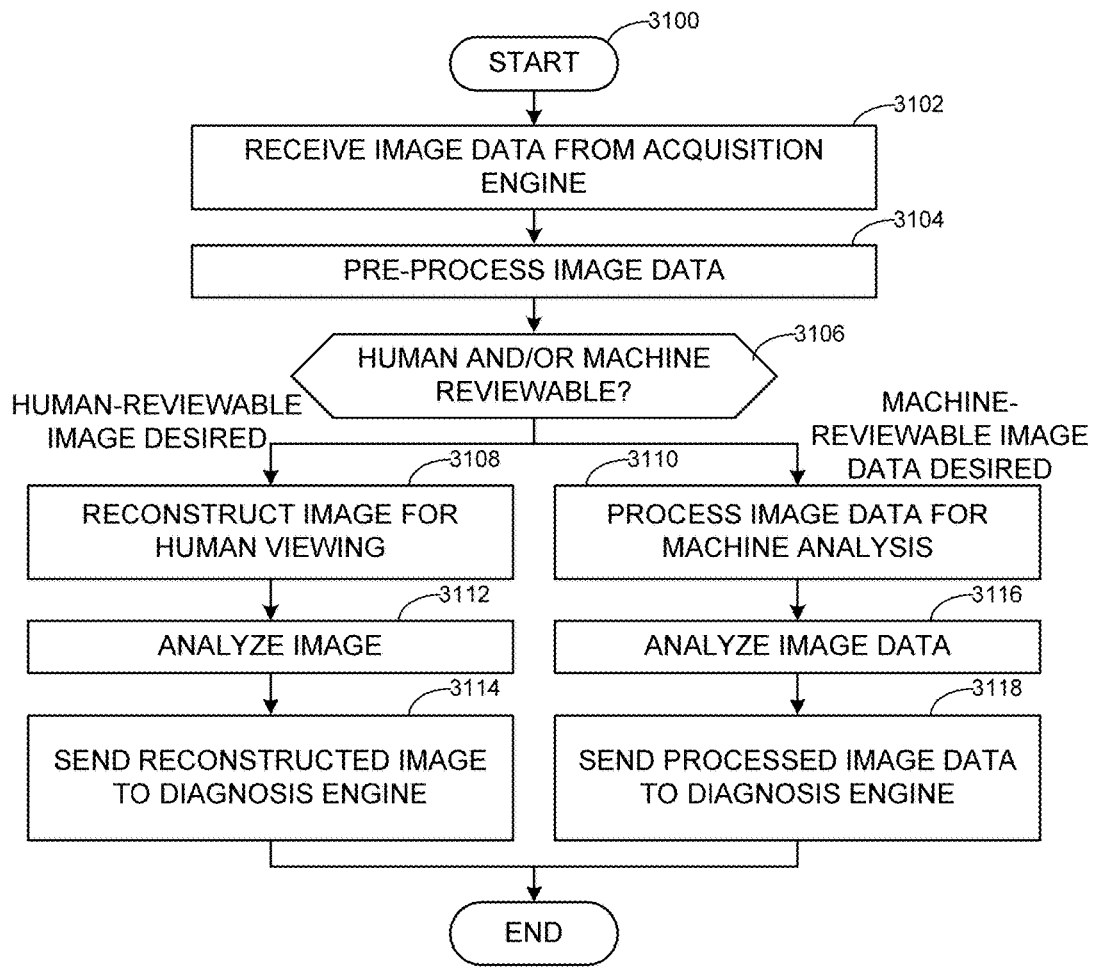
FIG. 31A illustrates a flow diagram of an example method for image reconstruction.

FIG. 31A illustrates a flow diagram of an example method 3100 for image reconstruction. At block 3102, image data is received from the acquisition engine 1430. For example, the reconstruction engine 1440 receives image from the imaging device 1410 via the acquisition engine 1430. At block 3104, the image data is pre-processed. For example, the DDLD 1532 pre-processes the image data according to one or more settings or parameters, such as whether a human-viewable and/or machine-readable image is to be generated from the acquired image data. For example, the reconstruction DDLD 1532 can be deployed with a network trained to replace a noise reduction algorithm (e.g., by training the DLN in the learning and improvement factory 1530 on a plurality of examples of noisy and noise-free image pairs) to convert noisy data to produce high quality data.

As described above, a machine-readable image need not be formatted for human viewing but can instead be processed for machine analysis (e.g., computer-aided diagnosis, etc.). Conversely, a human-viewable image should have clarity in features (e.g., sufficient resolution and reduced noise, etc.) such that a radiologist and/or other human user 1404 can read and evaluate the image (e.g., perform a radiology reading). The DDLD 1532 can evaluate the image data before reconstruction and determine reconstruction settings, for example. Reconstruction and/or other processing parameters can be determined by the DDLD 1532 for human-viewable and/or machine-readable images.

At block 3106, the reconstruction settings are evaluated to determine whether a human-viewable and/or machine-readable image is to be generated. In some examples, only a human-viewable image is to be generated for user 1404 review. In some examples, only machine-processable image data is to be generated for automatic evaluation by the diagnosis engine 1450, for example. In some examples, both human-viewable image and machine-processable image data are to be provided.

If a human-reviewable image is desired, then, at block 3108, an image is reconstructed using the image data for human viewing (e.g., radiologist reading). For example, rather than employing a computationally intensive iterative reconstruction algorithm that takes in raw data and produces an image, the reconstruction engine 1440 and DDLD 1532 (e.g., trained on a plurality of examples of raw and reconstructed image pairs) can process raw image data and produce one or more reconstructed images of equivalent or near-equivalent quality to the iterative algorithm. Additionally, as described above, the DDLD 1532 can convert noisy data into higher quality image data, for example. Further, the DDLD 1532 can be used to condition the image data and provide a "wide view" to reconstruct images outside the field of view (FOV) of a detector of the imaging device 1410. Rather than using equations to extrapolate data outside the detector, the DDLD 1532 can fill in the gaps based on what it has learned from its training data set. If machine-reviewable image data is desired, then, at block 3110, the image data is processed for machine analysis. The DDLD 1532 can process the image data to remove noise, expand field of view, etc., for example, At block 3112, the reconstructed image is analyzed. For example, the image is analyzed by the DDLD 1532 for quality, IQI, data quality index, other image quality metric(s), etc. The DDLD 1532 learns from the content of the reconstructed image (e.g., identified features, resolution, noise, etc.) and compares to prior reconstructed images (e.g., for the same patient 1406, of the same type, etc.). At block 3114, the reconstructed image is sent to the diagnosis engine 1450. The image can be displayed and/or further processed by the diagnosis engine 1450 and its DDLD 1542 to facilitate diagnosis of the patient 1406, for example.

Similarly, at block 3116, the processed image data is analyzed. For example, the image data is analyzed by the DDLD 1532 for quality, IQI, data quality index, other image quality metric(s), etc. The DDLD 1532 learns from the content of the machine-processable image data (e.g., identified features, resolution, noise, etc.) and compares to prior image data and/or reconstructed images (e.g., for the same patient 1406, of the same type, etc.). At block 3118, the processed image data is sent to the diagnosis engine 1450. The image data can be further processed by the diagnosis engine 1450 and its DDLD 1542 to facilitate diagnosis of the patient 1406, for example. For example, machine-readable image data can be provided to the diagnosis engine 1450 along with other patient information (e.g., history, lab results, 2D/3D scout images, etc.) which can be processed together to generate an output to support the user 1404 in diagnosing the patient 1406 (e.g., generating support documentation to assist the radiologist in reading the images, etc.).

Figure 31B:
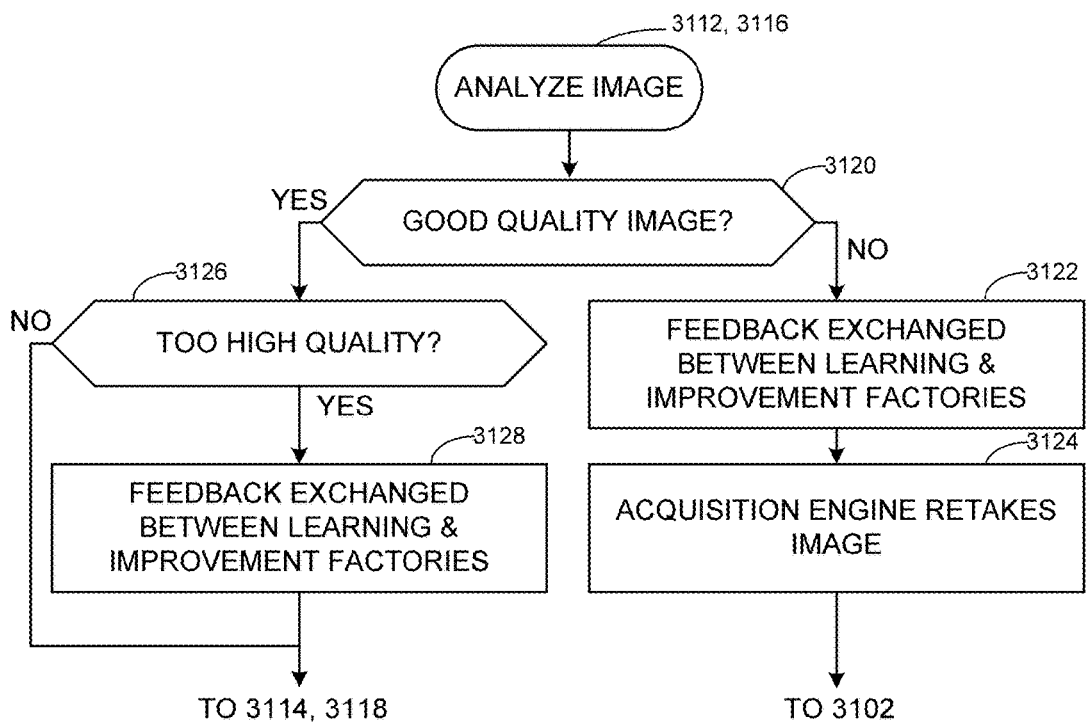
FIG. 31B provides further detail regarding a particular implementation of the example method of FIG. 31A for image reconstruction.

FIG. 31B provides further detail regarding blocks 3112 and 3116 in a particular implementation of the example method 3100 of FIG. 31A for image reconstruction. The example method of FIG. 31B can be triggered by one or both of blocks 3112 and 3116 in the example method 3100.

At block 3120, the image/image data is analyzed to determine whether the acquired image is a good quality image. To determine whether the acquired image data represents a "good quality" image, the data can be compared to one or more thresholds, values, settings, etc. As described above, an IQI, other data quality index, detectability index, diagnostic index, etc., can be generated to represent a reliability and/or usefulness of the data for diagnosis of the patient 1406. While the IQI captures a scale (e.g., a Likert scale, etc.) of acceptability of an image to a radiologist for diagnosis. Other indices, such as resolution image quality, noise image quality, biopsy data quality, and/or other data quality metric can be incorporated to represent suitability of image data for diagnosis, for example. For example, a task-specific data quality index can represent a quality of acquired image data for machine-oriented analysis.

At block 3122, if the acquired and processed image and/or image data is not of sufficient quality, then the reconstruction DDLD 1532 sends feedback to the acquisition learning and improvement factory 1520 indicating that the image data obtained is not of sufficient quality for analysis and diagnosis. That way the factory 1520 continues to learn and improve image acquisition settings for different circumstances and can generate a network model to redeploy the DDLD 1522. At block 3124, the acquisition engine 1430 triggers a re-acquisition of image data from the patient 1406 via the imaging device 1410 (e.g., at block 3102). Thus, the reconstruction DDLD 1532 and acquisition DDLD 1522 can work together to modify imaging parameters and reacquire image data while the patient 1406 may still be on the table or at least in close proximity to the imaging device 1410, for example, thereby reducing hardship on the patient 1406 and staff as well as equipment scheduling.

At block 3126, if the image/image data quality satisfies the threshold, the image quality can be evaluated to determine whether the quality is too high. An image quality that is too high (e.g., an IQI of 5 indicating a "perfect" image, etc.) can indicate that the patient 1406 was exposed to too much radiation when obtaining the image data. If an image quality of 3 or 4 is sufficient for diagnostic reading by the user 1404 and/or diagnosis engine 1450, for example, then an image quality of 5 is not necessary. If the image quality is too high, then, at block 3128, feedback is provided from the reconstruction DDLD 1532 to the acquisition learning and improvement factory 1520 to adjust dosage/intensity settings of the imaging device 1410 for future image acquisition (e.g., of a particular type, for that patient, etc.). The process then continues at block 3114 and/or 3118 to provide the reconstructed image (block 3114) and/or processed image data (block 3118) to the diagnosis engine 1450 for processing and review.

While example implementations are illustrated in conjunction with FIGS. 1-31B, elements, processes and/or devices illustrated in conjunction with FIGS. 1-31B may be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components disclosed and described herein are shown in conjunction with at least FIGS. 8C, 8D, 12, 13, 16, 17, 19, 21, 31A, and 31B. In the examples, the machine readable instructions include a program for execution by a processor such as the processor 3212 shown in the example processor platform 3200 discussed below in connection with FIG. 32. The program may be embodied in machine readable instructions stored on a tangible computer readable storage medium such as a CD-ROM, a floppy disk, a hard drive, a digital versatile disk (DVD), a Blu-ray disk, or a memory associated with the processor 3212, but the entire program and/or parts thereof could alternatively be executed by a device other than the processor 3212 and/or embodied in firmware or dedicated hardware. Further, although the example program is described with reference to the flowcharts illustrated in conjunction with at least FIGS. 8C, 8D, 12, 13, 16, 17, 19, 21, 31A, and 31B, many other methods of implementing the components disclosed and described herein may alternatively be used. For example, the order of execution of the blocks may be changed, and/or some of the blocks described may be changed, eliminated, or combined. Although the flowcharts of at least FIGS. 8C, 8D, 12, 13, 16, 17, 19, 21, 31A, and 31B depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of at least FIGS. 8C, 8D, 12, 13, 16, 17, 19, 21, 31A, and 31B may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of at least FIGS. 8C, 8D, 12, 13, 16, 17, 19, 21, 31A, and 31B may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 32:
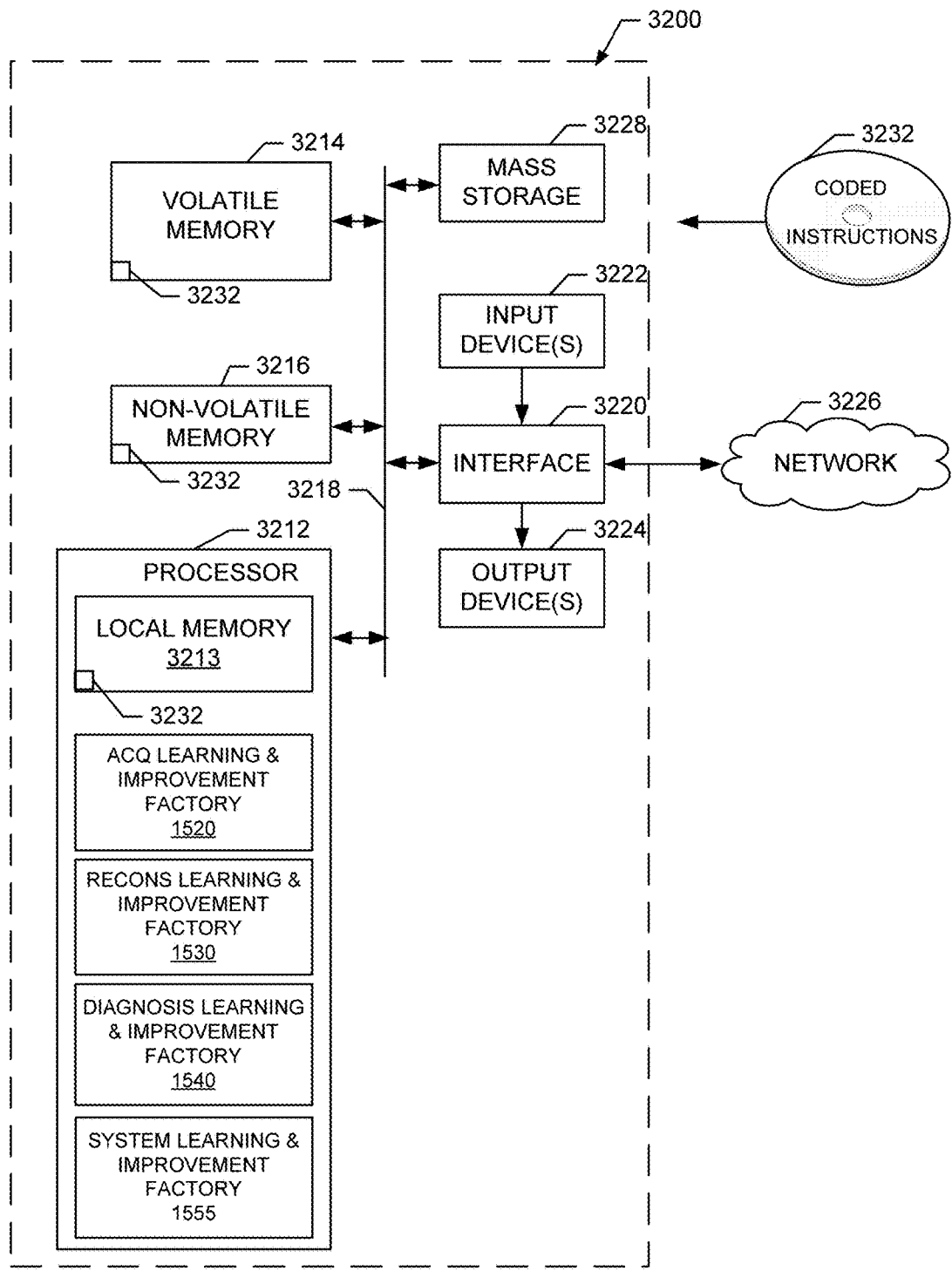
FIG. 32 is a block diagram of a processor platform structured to execute the example machine readable instructions to implement components disclosed and described herein.

FIG. 32 is a block diagram of an example processor platform 3200 structured to executing the instructions of at least FIGS. 8C, 8D, 12, 13, 16, 17, 19, 21, 31A, and 31B to implement the example components disclosed and described herein. The processor platform 3200 can be, for example, a server, a personal computer, a mobile device (e.g., a cell phone, a smart phone, a tablet such as an iPad™), a personal digital assistant (PDA), an Internet appliance, or any other type of computing device.

The processor platform 3200 of the illustrated example includes a processor 3212. The processor 3212 of the illustrated example is hardware. For example, the processor 3212 can be implemented by integrated circuits, logic circuits, microprocessors or controllers from any desired family or manufacturer.

The processor 3212 of the illustrated example includes a local memory 3213 (e.g., a cache). The example processor 3212 of FIG. 32 executes the instructions of at least FIGS.

8C, 8D, 12, 13, 16, 17, 19, 21, 31A, and 31B to implement the learning and improvement factories 1520, 1530, 1540, 1555 and/or other components such as information subsystem 1420, acquisition engine 1430, reconstruction engine 1440, diagnosis engine 1450, etc. The processor 3212 of the illustrated example is in communication with a main memory including a volatile memory 3214 and a non-volatile memory 3216 via a bus 3218. The volatile memory 3214 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 3216 may be implemented by flash memory and/or any other desired type of memory device. Access to the main memory 3214, 3216 is controlled by a clock controller.

The processor platform 3200 of the illustrated example also includes an interface circuit 3220. The interface circuit 3220 may be implemented by any type of interface standard, such as an Ethernet interface, a universal serial bus (USB), and/or a PCI express interface.

In the illustrated example, one or more input devices 3222 are connected to the interface circuit 3220. The input device(s) 3222 permit(s) a user to enter data and commands into the processor 3212. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 3224 are also connected to the interface circuit 3220 of the illustrated example. The output devices 3224 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 3220 of the illustrated example, thus, typically includes a graphics driver card, a graphics driver chip or a graphics driver processor.

The interface circuit 3220 of the illustrated example also includes a communication device such as a transmitter, a receiver, a transceiver, a modem and/or network interface card to facilitate exchange of data with external machines (e.g., computing devices of any kind) via a network 3226 (e.g., an Ethernet connection, a digital subscriber line (DSL), a telephone line, coaxial cable, a cellular telephone system, etc.).

The processor platform 3200 of the illustrated example also includes one or more mass storage devices 3228 for storing software and/or data. Examples of such mass storage devices 3228 include floppy disk drives, hard drive disks, compact disk drives, Blu-ray disk drives, RAID systems, and digital versatile disk (DVD) drives.

The coded instructions 3232 of FIG. 32 may be stored in the mass storage device 3228, in the volatile memory 3214, in the non-volatile memory 3216, and/or on a removable tangible computer readable storage medium such as a CD or DVD.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Figure 33:
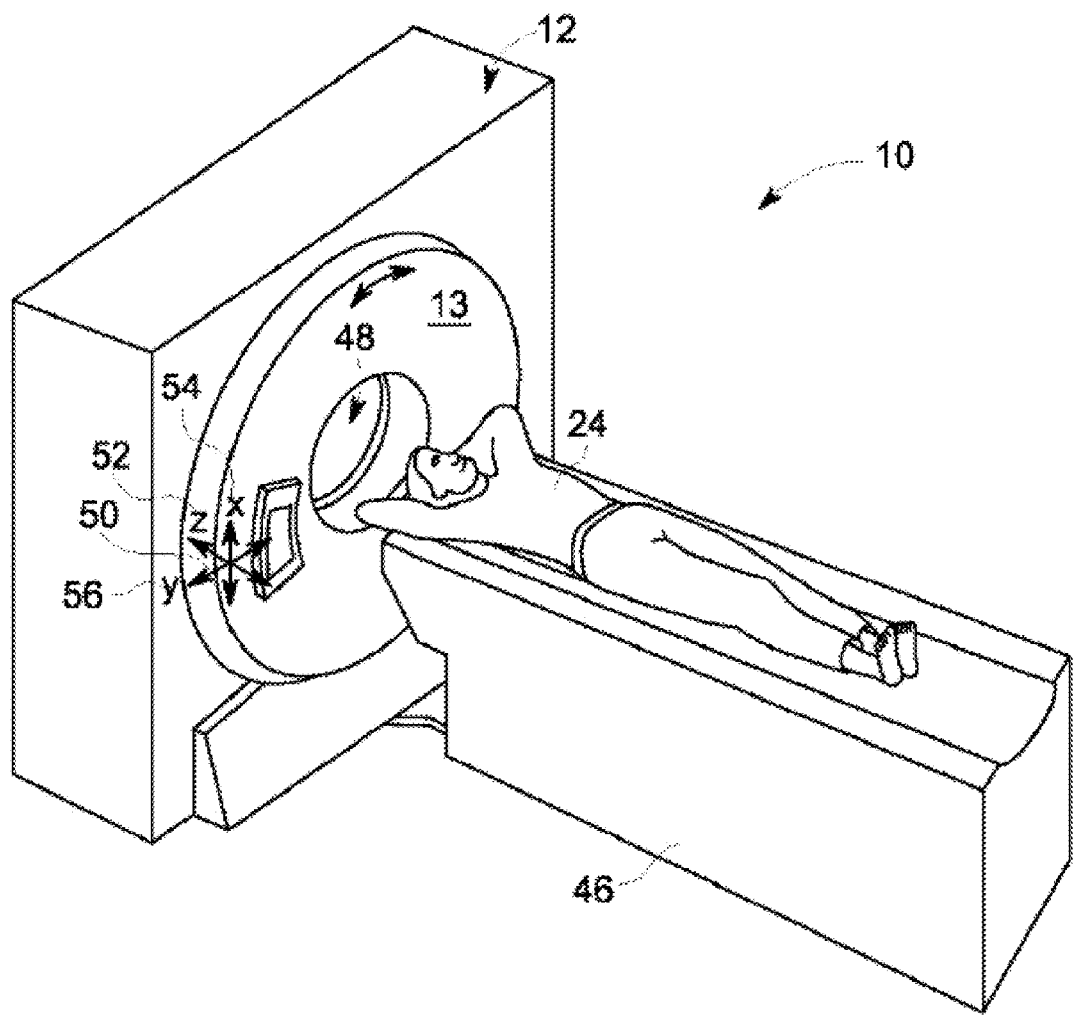
FIGS. 33-34 illustrate an example imaging system to which the methods, apparatus, and articles of manufacture disclosed herein can be applied.
Figure 34:
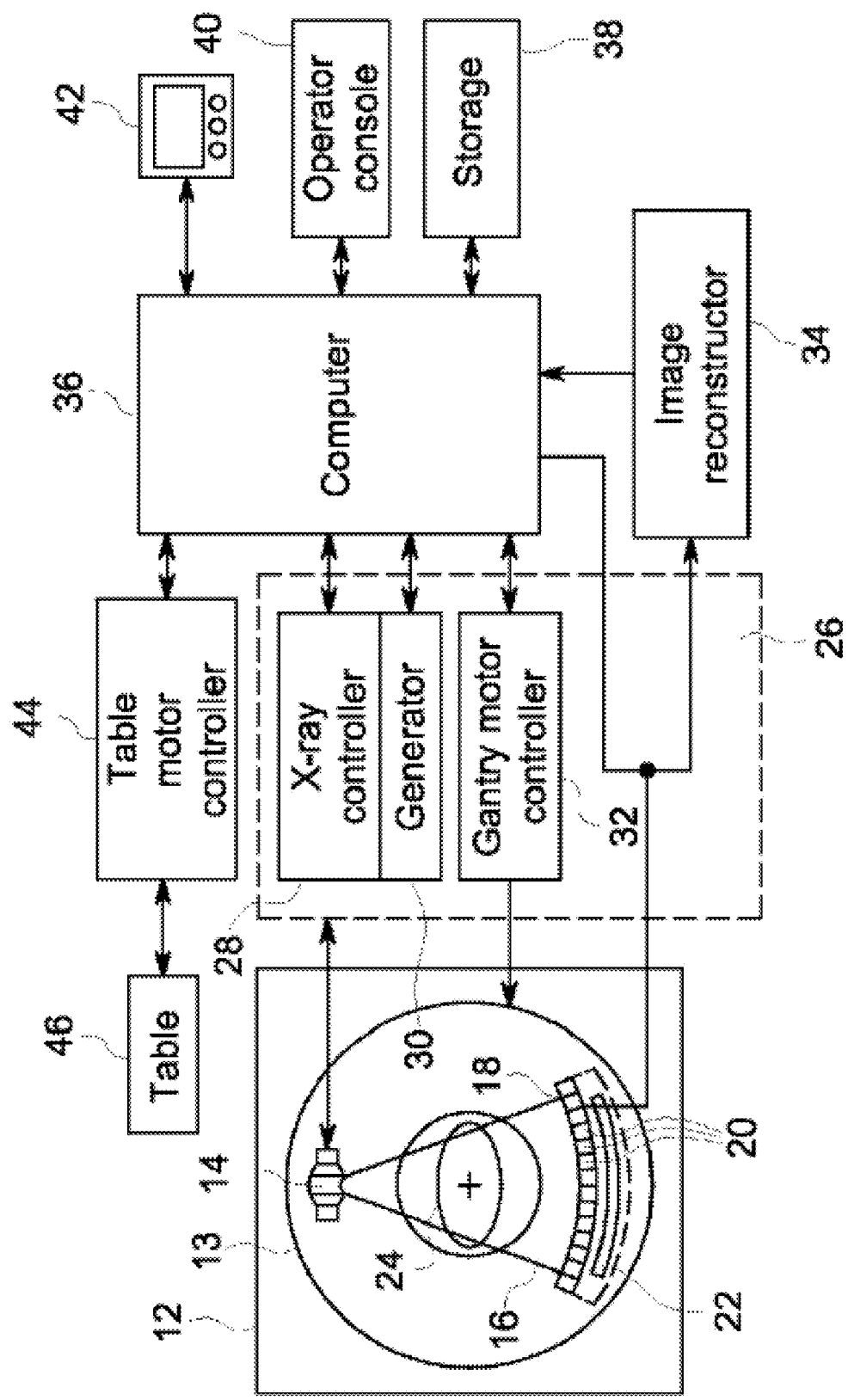

The methods, apparatus, and articles of manufacture described above can be applied to a variety of healthcare and non-healthcare systems. In one particular example, the methods, apparatus, and articles of manufacture described above can be applied to the components, configuration, and operation of a CT imaging system. FIGS. 33-34 illustrate an example implementation of the imaging device 1410 as a CT imaging scanner to which the methods, apparatus, and articles of manufacture disclosed herein can be applied. FIGS. 33 and 34 show a computed tomography (CT) imaging system 10 including a gantry 12. Gantry 12 has a rotary member 13 with an x-ray source 14 that projects a beam of x-rays 16 toward a detector assembly 18 on the opposite side of the rotary member 13. A main bearing may be utilized to attach the rotary member 13 to the stationary structure of the gantry 12. X-ray source 14 includes either a stationary target or a rotating target. Detector assembly 18 is formed by a plurality of detectors 20 and data acquisition systems (DAS) 22, and can include a collimator. The plurality of detectors 20 sense the projected x-rays that pass through a subject 24, and DAS 22 converts the data to digital signals for subsequent processing. Each detector 20 produces an analog or digital electrical signal that represents the intensity of an impinging x-ray beam and hence the attenuated beam as it passes through subject 24. During a scan to acquire x-ray projection data, rotary member 13 and the components mounted thereon can rotate about a center of rotation.

Rotation of rotary member 13 and the operation of x-ray source 14 are governed by a control mechanism 26 of CT system 10. Control mechanism 26 can include an x-ray controller 28 and generator 30 that provides power and timing signals to x-ray source 14 and a gantry motor controller 32 that controls the rotational speed and position of rotary member 13. An image reconstructor 34 receives sampled and digitized x-ray data from DAS 22 and performs high speed image reconstruction. The reconstructed image is output to a computer 36 which stores the image in a computer storage device 38.

Computer 36 also receives commands and scanning parameters from an operator via operator console 40 that has some form of operator interface, such as a keyboard, mouse, touch sensitive controller, voice activated controller, or any other suitable input apparatus. Display 42 allows the operator to observe the reconstructed image and other data from computer 36. The operator supplied commands and parameters are used by computer 36 to provide control signals and information to DAS 22, x-ray controller 28, and gantry motor controller 32. In addition, computer 36 operates a table motor controller 44 which controls a motorized table 46 to position subject 24 and gantry 12. Particularly, table 46 moves a subject 24 through a gantry opening 48, or bore, in whole or in part. A coordinate system 50 defines a patient or Z-axis 52 along which subject 24 is moved in and out of opening 48, a gantry circumferential or X-axis 54 along which detector assembly 18 passes, and a Y-axis 56 that passes along a direction from a focal spot of x-ray tube 14 to detector assembly 18.

Thus, certain examples can apply deep learning and/or other machine learning techniques to configuration, design, and/or operation of the CT scanner 10 and its gantry 12, rotary member 13, x-ray source 14, detector assembly 18, control mechanism 26, image reconstructor 34, computer 36, operator console 40, display 42, table controller 44, table 46, and/or gantry opening 48, etc. Component configuration, operation, structure can be monitored based on input, desired output, actual output, etc., to learn and suggest change(s) to configuration, operation, and/or structure of the scanner 10 and/or its components, for example.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. An imaging system configuration apparatus comprising:
   a training learning device including a first processor to implement a first deep learning network to learn a first set of imaging system configuration parameters based on a first set of inputs from a plurality of prior image acquisitions to configure at least one imaging system for image acquisition, the training learning device to receive and process feedback including operational data from the plurality of image acquisitions by the at least one imaging system; and
   a deployed learning device including a second processor to implement a second deep learning network, the second deep learning network generated from the first deep learning network of the training learning device, the deployed learning device configured to provide a second imaging system configuration parameter to the imaging system in response to receiving a second input for image acquisition.

2. The apparatus of claim 1, further including an interface to connect to the imaging system, the interface, once connected, enabling automated exchange of data between the imaging system and at least one of the training learning device and the deployed learning device.

3. The apparatus of claim 1, wherein the second input includes patient information for a subject of the image acquisition.

4. The apparatus of claim 1, wherein the feedback includes image reconstruction quality information.

5. The apparatus of claim 4, wherein the deployed learning device is to generate a recommendation for next action when the image reconstruction quality information fails to satisfy a threshold.

6. The apparatus of claim 4, wherein the processor is to set the first set of imaging system configuration parameters as a default set of parameters for the imaging system when the image reconstruction quality information satisfies a threshold.

7. The apparatus of claim 1, wherein the second input includes a purpose of a medical exam associated with the image acquisition.

8. A non-transitory computer readable medium comprising instructions which, when executed, configure a machine to implement an imaging system configuration apparatus, the apparatus including:
   a training learning device including a first processor to implement a first deep learning network to learn a first set of imaging system configuration parameters based on a first set of inputs from a plurality of prior image acquisitions to configure at least one imaging system for image acquisition, the training learning device to receive and process feedback including operational data from the plurality of image acquisitions by the at least one imaging system; and
   a deployed learning device including a second processor to implement a second deep learning network, the second deep learning network generated from the first deep learning network of the training learning device, the deployed learning device configured to provide a second imaging system configuration parameter to the imaging system in response to receiving a second input for image acquisition.

9. The computer readable medium of claim 8, wherein the instructions, when executed, further configure the machine to include an interface to connect to the imaging system, the interface, once connected, enabling automated exchange of data between the imaging system and at least one of the training learning device and the deployed learning device.

10. The computer readable medium of claim 8, wherein the second input includes patient information for a subject of the image acquisition.

11. The computer readable medium of claim 8, wherein the feedback includes image reconstruction quality information.

12. The computer readable medium of claim 11, wherein the first deep learning network is to generate a recommendation for next action when the image reconstruction quality information fails to satisfy a threshold.

13. The computer readable medium of claim 11, wherein the first set of imaging system configuration parameters is set as a default set of parameters for the imaging system when the image reconstruction quality information satisfies a threshold.

14. The computer readable medium of claim 8, wherein the second input includes a purpose of a medical exam associated with the image acquisition.

15. A method comprising:
   training a first deep learning network at a training learning device to learn a first set of imaging system configuration parameters based on a first set of inputs from a plurality of prior image acquisitions to configure at least one imaging system for image acquisition, the training learning device to receive and process feedback including operational data from the plurality of image acquisitions by the at least one imaging system;
   generating a second deep learning network at a deployed learning device using the first deep learning network;
   deploying the deployed learning device with the second deep learning network to provide a second imaging system configuration parameter to the imaging system in response to receiving a second input for image acquisition;
   receiving feedback from the imaging system, the feedback including operational data from the image acquisition by the imaging system; and
   updating the first deep learning network of the training learning device based on the received feedback.

16. The method of claim 15, further including connecting the image acquisition configuration device to the imaging system via an interface, wherein the interface, once connected, enables automated exchange of data between the imaging system and at least one of the training learning device and the deployed learning device.

17. The method of claim 15, wherein the second input includes patient information for a subject of the image acquisition.

18. The method of claim 15, wherein the feedback includes image reconstruction quality information.

19. The method of claim 18, wherein the second deep learning network is to generate a recommendation for next action when the image reconstruction quality information fails to satisfy a threshold.

20. The method of claim 18, further including wherein the image acquisition configuration device is to set the first set of imaging system configuration parameters as a default set of parameters when the image reconstruction quality information satisfies a threshold.

21. The system of claim 1, wherein the first set of inputs includes data pertaining to at least one patient who has been imaged.

22. The system of claim 21, wherein the data includes imaging data and non-imaging data.

\* \* \* \* \*

UNITED STATES PATENT AND TRADEMARK OFFICE
CERTIFICATE OF CORRECTION

PATENT NO.         : 10,127,659 B2
APPLICATION NO.    : 15/360626
DATED              : November 13, 2018
INVENTOR(S)        : Jiang Hsieh, Gopal Avinash and Saad Sirohey Page 1 of 1

It is certified that error appears in the above-identified patent and that said Letters Patent is hereby corrected as shown below:

In the Claims

Column 53, Line 1 Claim 21 delete "The system of claim 1" and add -- The apparatus of claim 1 --.

Column 53, Line 4 Claim 22 delete "The system of claim 21" and add -- The apparatus of claim 21 --.

Signed and Sealed this
Sixteenth Day of April, 2019

Andrei Iancu
*Director of the United States Patent and Trademark Office*